United States Patent
Weigele et al.

(10) Patent No.: US 7,115,589 B2
(45) Date of Patent: Oct. 3, 2006

(54) PURINE DERIVATIVES

(75) Inventors: Manfred Weigele, Cambridge, MA (US); Tomi K. Sawyer, Southborough, MA (US); Regine Bohacek, Boston, MA (US); William C. Shakespeare, Framingham, MA (US); Rajeswari Sundaramoorthi, Watertown, MA (US); Yihan Wang, Newton, MA (US); David C. Dalgarno, Brookline, MA (US); Chester A. Metcalf, III, Boston, MA (US)

(73) Assignee: ARIAD Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/740,393

(22) Filed: Dec. 18, 2000

(65) Prior Publication Data

US 2002/0068721 A1    Jun. 6, 2002

Related U.S. Application Data

(63) Continuation-in-part of application No. 09/740,653, filed on Dec. 18, 2000, now abandoned, and a continuation-in-part of application No. 09/740,267, filed on Dec. 18, 2000, now abandoned.

(60) Provisional application No. 60/240,788, filed on Oct. 16, 2000, provisional application No. 60/172,510, filed on Dec. 17, 1999, provisional application No. 60/172,161, filed on Dec. 17, 1999.

(51) Int. Cl.
```
C07F 9/6561    (2006.01)
A61K 31/675   (2006.01)
A61P 19/10    (2006.01)
A61P 19/08    (2006.01)
A61P 35/00    (2006.01)
```
(52) U.S. Cl. .......................... 514/81; 544/244
(58) Field of Classification Search ................ 544/244; 514/81
See application file for complete search history.

(56) References Cited

U.S. PATENT DOCUMENTS

| | | | |
|---|---|---|---|
| 4,008,363 A | 2/1977 | Re et al. | |
| 4,473,560 A | 9/1984 | Biere et al. | |
| 4,503,049 A | 3/1985 | Biere et al. | |
| 4,687,767 A | 8/1987 | Bosies et al. | |
| 4,687,768 A | 8/1987 | Benedict et al. | |
| 5,583,122 A | 12/1996 | Benedict et al. | |
| 5,635,495 A | 6/1997 | White et al. | |
| 5,663,159 A | 9/1997 | Starrett, Jr. et al. | |
| 5,837,871 A | 11/1998 | Kim et al. | |
| 5,849,905 A | 12/1998 | Gosselin et al. | |
| 5,866,556 A | 2/1999 | Heikkila-Hoikka et al. | |
| 5,986,086 A * | 11/1999 | Brush et al. ............. | 435/6 |
| 6,107,300 A | 8/2000 | Bakthavatchalam et al. | |
| 6,197,775 B1 | 3/2001 | Ubasawa et al. | |
| 6,255,485 B1 | 7/2001 | Gray et al. | |
| 6,281,201 B1 | 8/2001 | Suhadolnik et al. | |
| 6,284,748 B1 | 9/2001 | Dang et al. | |
| 6,573,044 B1 | 6/2003 | Gray et al. | |
| 6,767,906 B1 | 7/2004 | Imbach et al. | |
| 6,838,559 B1 | 1/2005 | Vaccaro et al. | |
| 2003/0187261 A1 | 10/2003 | Havlicek et al. | |
| 2004/0157864 A1 | 8/2004 | Wu et al. | |

FOREIGN PATENT DOCUMENTS

| | | |
|---|---|---|
| EP | 0084822 | 8/1983 |
| EP | 0085321 | 8/1983 |
| EP | 0170228 | 2/1986 |
| EP | 0186405 | 7/1986 |
| EP | 0304962 | 3/1989 |
| EP | 0398231 | 11/1990 |
| EP | 0478292 | 4/1992 |
| EP | 0531597 | 3/1993 |
| EP | 0832896 | 4/1998 |
| WO | WO 94/09017 | 4/1994 |
| WO | WO 94/17090 | 8/1994 |
| WO | WO 98/11121 | 3/1998 |
| WO | WO 98/15563 | 4/1998 |
| WO | WO 98/39344 | 9/1998 |
| WO | WO 00/44750 | 8/2000 |

OTHER PUBLICATIONS

Wada, JACS 116, 9901 (1994).*
Tate, Nature 280, 697 (1979).*
Kondo, Makromol. Chem. Rapid Commun. 1, 303 (1980).*
"Organic Chemistry", 3rd Edition, Morrison & Boyd, 1973, p. 40.*
Morrison and Boyd, "Organic Chemistry, 3rd edition" p. 658.*
Webster's Medical Desk Dictionary.*
Morrison and Boyd, "Organic Chemistry" (3d ed), p. 658.*
Hawley's Condensed Chemical Dictionary (14th Ed Richard Lewis Sr.) pp. 21 and 213.*

(Continued)

Primary Examiner—Mark L. Berch
(74) Attorney, Agent, or Firm—David L. Berstein

(57) ABSTRACT

This invention relates to compounds of the general formula:

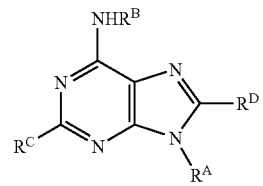

in which $R^A$, $R^B$, $R^C$ and $R^D$ are as defined herein, and to their preparation and use. In these compounds, $R^B$ is an aliphatic, heteroaliphatic, aryl, or heteroaryl moiety which comprises one or more phosphorus-containing moieties.

20 Claims, No Drawings

OTHER PUBLICATIONS

Webster's Medical Desk Dictionary (1986). p. 689.*
The American Heritage® Dictionary of the English Language: Fourth Edition. 2000 entry for bisulfate <http://www.bartleby.com/61/43/B0284300.html> downloaded from the Internet Sep. 22, 2004.*
"Sulfo Group" <http://www.biochem.ucl.ac.uk/bsm/pdbsum/hetgroups/indSFO.html> downloaded from the Internet Sep. 22, 2004.*
Belstein Registry No. 3585142.
Belstein Registry No. 1194999.
Filippov et al., (1997) Nucleosides & Nucleotides, 16(7-9); 1403-1406.
Belstein Registry No. 7844842.
Belstein Registry No. 7845906.
Belstein Registry No. 7846892.
Belstein Registry No. 5124036.
Belstein Registry No. 5181946.
Charubala et al., (1981) Hetreocycles, vol. 15; 761-776.
Database WPI Abstract: Cherkasov et al., (1977) Section Ch, Week 197826, Derwent Pub. Ltd. Abstract fir, SU 412765.
Database Chemabs: Filippov et al., (1997) Chem. Abst. Service, Columbus Ohio, Access No. 128:13393.
Parkin, (1991) J. Chem. Soc., Perkin Trans 12: 2983-2990.
Shadid et al. (1990) Tetrahedron, vol. 46, No. 3; 901-912.
Shadid et al. (1990) Tetrahedron, vol. 46, No. 6; 2179-2186.
Alexander, et al. (2000) Collect. Czech. Chem. Commun., vol. 65; 1713-1725.
Beilstein Registry No. 8375175.

* cited by examiner

PURINE DERIVATIVES

PRIORITY INFORMATION

This document claims priority as a continuation in part under 35 U.S.C. § 119(e) to each of U.S. Provisional Patent Application No. 60/172,510, filed Dec. 17, 1999, entitled "Bone Targeting Agents", U.S. Provisional Patent Application No. 60/172,161, filed Dec. 17, 1999, entitled "Proton Pump Inhibitors", and U.S. Provisional Patent Application No. 60/240,788, filed Oct. 16, 2000 entitled "Bone Targeting Agents", the entire contents of each of which are hereby incorporated herein by reference. This document also claims the priority as a continuation in part of U.S. National patent application Ser. No. 09/740,267, entitled "Novel Heterocycles" and U.S. National patent application Ser. No. 09/740,653, entitled "Novel Purines", each of which is filed on Dec. 18, 2000 even date herewith now abandoned and is hereby incorporated herein by reference.

BACKGROUND OF THE INVENTION

The need to treat debilitating bone disorders, such as osteoporosis, has led to extensive research on the mechanism and regulation of continuous bone formation and resorption. In particular, an appropriate balance of osteoblasts, which function to form bone tissue, and osteoclasts, which function to resorb bone tissue, is required to maintain the structural integrity and proper functioning of the skeleton in spite of continuous metabolism. Any changes in this balance of metabolism, such as an increased bone resorption (either absolute, or an increase via decreased bone formation relative to bone resorption) can lead bone diseases or disorders. One of the most common diseases resulting from this imbalance is osteoporosis, which is characterized by a decrease in bone mass and deterioration in skeletal microarchitecture leading to an increased fragility and susceptibility to fractures. Other diseases which result from, or otherwise involve, alterations in bone resorption include, but are not limited to, Paget's Disease, primary and secondary hyperparathyroidism, humoral hypercalcemia of malignancy, various cancers where resorption is increased, and rheumatoid arthritis.

Because of the serious disorders that may result from a metabolic imbalance, researchers have been interested in studying bone metabolism and the mechanism by which bone resorption and formation occurs, to ultimately develop a strategy for inhibiting resorption, and/or to improve bone mass and/or bone micro-architecture by stimulating osteoblast activity. However, the action of both osteoclasts and osteoblasts is controlled by a number of complex factors, and thus developing selective therapeutics has proven to be a difficult task.

One approach that has been taken for the development of novel therapeutics for bone disorders is inhibition of the osteoclast proton pump. Baron and coworkers have previously demonstrated that this proton pump is a vacuolar $H^+$-ATPase (see, Blair et al., *Science* 1989, 245, 855–857; Finbow et al., *Biochem. J.* 1997, 324, 697–712; Forgac, M. *Soc. Gen. Physiol. Ser.* 1996, 51, 121–132). It has been shown that osteoclasts, to effect bone resorption, ultimately lower the pH in the sealed microcompartment which underlies their site of attachment to the bone surface (see, Baron et al., *J. Cell. Biol.* 1985, 101, 2210–2222), thus resulting in the acidic enviomnent required to dissolve the bone mineral and to allow degradation of the bone matrix by proteases. The osteoclast ultimately uses a proton pump (an ATP-dependent transport of protons) to achieve this acidification and thus any therapeutic inhibition of the osteoclast proton pump should lead to a decrease in bone loss or turnover. As a result, many novel therapeutics developed to reduce bone resorption have focused on the inhibition of the proton pump to prevent osteoclast activity and excessive bone resorption. For a discussion of the vacuolar $H^+$-ATPase and inhibitors of vacuolar $H^+$-ATPase see Farina et al., *Exp. Opin. Ther. Patents* 1999, 9, 157–168 and David, P. and Baron, R. "The Vacuolar $H^+$-ATPase: A Potential Target for Drug Development in Bone Diseases" *Exp. Opin. Invest. Drugs* 1995, 4, 725–740.

In addition to the inhibition of the proton pump, studies have also been directed towards the control of signal transduction to ultimately affect osteoclast or osteoblast function. For example, studies have provided evidence that Src protein kinases play a cruical role in osteoclastic function, and it has been shown in different cell types that phosphorylation by Src, and related kinases, of proteins proposed to participate or regulate the cytoskeletal architecture is one important requirement for their proper function (see, for example, "A Novel Inhibitor of the Tyrosine Kinase Src Suppresses Phosphorylation of Its Major Cellular Substrates and Reduces Bone Resorption In Vitro and in Rodent Models In Vivo" Missbach et al., *Bone* 1999, 24, 437–449). Because the cytoskeleton plays an important role in osteoclast motility, attachment, and formation of the sealing zone, it is likely that these cytoskeletal proteins may influence osteoclast function. Thus, agents which inhibit or promote interactions with Src or related kinases, are likely to affect cytoskeletal proteins and ultimately affect osteoclast function. Several compounds have been reported as inhibitors of tyrosine Src kinase and thus may be of some use in the inhibition of osteoclast-mediated bone resorption (see, for example, Missbach et al., *Bone* 1999, 24, 437–449; Connolly et al., *Bioorg. & Med. Chem. Lett.* 1997, 7, 2415–2420; Trump-Kallmeyer et al., *J. Med. Chem.* 1998, 41, 1752–1763; Klutchko et al., *J. Med. Chem.* 1998, 41, 3276–3292; Legraverend et al., *Bioorg. & Med. Chem.* 1999, 7, 1281–1293; Chang et al., *Chem. & Biol.* 1999, 6, 361–375; Lev et al. *Nature* 1995, 376, 737–784; Palmer et al., *J. Med. Chem.* 1997, 40, 1519–1529.

As described above, many of the existing therapeutics that have been developed for the treatment of bone disorders such as osteoporosis, involve the inhibition of osteoclast activity. For example, estrogens, bisphosphonates, calcitonin, flavonoids, selective estrogen receptor modulators are believed to act by the inhibition of osteoclast activity. Additionally, more recently, novel therapeutics have been developed to promote a fast increase in bone mineral content by promoting osteoblast activity. Such examples include peptides from the parathyroid hormone family, strontium ranelate, and growth hormone and insulin-like growth response (see, for example, "Promising New Agents in Osteoporosis", Reginster et al. *Drugs R & D* 1999, 3, 195–201). Unfortunately, a significant problem of many of these therapetic agents, however, is that they are not specific enough for bone tissue and thus may lead to unwanted adverse side effects. Significant problems with bisphosphonates, for example, are well known. See e.g. Ezra and Golomb, *Advanced Drug Delivery Reviews* 2000, 42, 175–195.

Clearly, as evidenced by the number of different approaches to the available therapeutic agents, bone metabolism is controlled by a variety of factors. A common theme, however, is the desire to develop selective inhibitors or promoters of osteoclast or osteoblast activity, respectively.

3

Although progress has been made towards developing therapeutic agents for osteoporosis and other bone disorders, there remains a need to develop potent and selective agents having minimal side effects. More generally, there remains a need to develop compounds that can regulate cellular signal transduction pathways to inhibit or promote complex biological processes in order to treat and/or prevent diseases mediated by such signaling.

DESCRIPTION OF THE INVENTION

1. General Description of Compounds of the Invention

This invention concerns a new family of compounds which have a broad range of useful biological and pharmacological activities. These include compounds of general formula (I), as further defined below:

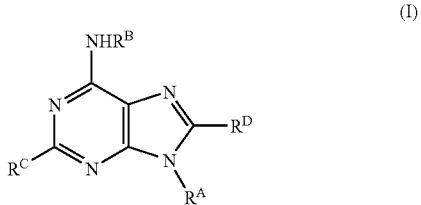

(I)

wherein
$R^A$ is hydrogen, or an aliphatic, heteroaliphatic, aryl, or heteroaryl moiety;
$R^B$ is an aliphatic, heteroaliphatic, aryl, or heteroaryl moiety which comprises one or more phosphorus-containing moieties;
$R^C$ is hydrogen, halogen, an aliphatic, heteroaliphatic, aryl, or heteroaryl moiety, or —ZR, wherein Z is —O—, —S—, or NR, wherein each occurrence of R (or R') without a further alphanumeric superscript is independently hydrogen, or a substituted or unsubstituted aliphatic, heteroaliphatic, aryl, or heteroaryl moiety;
$R^D$ is hydrogen, halogen, an aliphatic, heteroaliphatic, aryl, or heteroaryl moiety, or —ZR;
wherein in each of the foregoing groups each aliphatic or heteroaliphatic moiety may be branched or unbranched, cyclic or acyclic, substituted or unsubstituted, and may contain one or more electronically unsaturated bonds, and each aryl and heteroaryl moiety may be substituted or unsubstituted;
with the three limitations discussed immediately below.
First, either (1) $R^D$ is a moiety other than one comprising a substituted or unsubstituted arylene moiety (in which up to two methine carbons may be replaced by nitrogen atoms), a C3–7 cycloalkylene moiety (which may contain nitrogen atoms in place of up to two ring carbons), an indanylene moiety, or a 1,2,3,4-tetrahydronaphthylene moiety; or (2) $R^D$ is a moiety other than one terminating in a cyano group or in an N-substituted or unsubstituted amino, amidino, guanidino or guanidinoalkyl group.
Second, in compounds in which $R^C$ is H, OH, halogen, alkoxy or cycloalkoxy groups of 1 to 6 carbon atoms (which alkoxy and cycloalkoxy groups can be substituted with phenyl) or amine, which can be substituted with phenyl or with alkyl or cycloalkyl groups of 1 to 6 carbon atoms, and $R^A$ is benzyl, phenyl or C1–4 alkyl, optionally substituted with oxygen (e.g. in the form of an ether or alcohol), $R^B$ is a moiety other than a heteroatom- and/or halogen-substi-

4 tuted derivative of a 3 to 8 carbon cycloalkyl, a 1 to 10 carbon alkyl, a 6 to 13 carbon aryl, or a 7 to 14 carbon aralkyl moiety in which the heteroatom is selected from N, P, S and O.
Third, (1) at least one of $R^A$, $R^C$ or $R^D$ comprises a phosphorus-containing moiety; (2) $R^C$ is covalently attached through a C—C bond to the carbon atom at ring position 2 of the purine ring system; or (3) $R^B$ comprises a phosphorus-containing moiety other than —P(O)$R^J R^{J'}$ where $R^J$ and $R^{J'}$ are independently OH, alkoxy, arylalkoxy, aryloxy, alkylcarbonyloxy-alkoxy, arylalkylcarbonyloxyalkoxy, $NR^k R^{k'}$, mono- or di-alkylaminocarbonylmethyloxy, (di-aryl-alkylaminocarbonylmethyloxy, arylamino, a D- or L-amino acid, N-alkyl)piperidine-4yloxy, 2-methylsulfonylethoxy, 1,3 thiazole-2-ylmethyloxy, 3-pyridylmethyloxy, or 2-((di-alkyl)amino)ethoxy, where $R^k$ is H, alkyl, cycloalkyl, cycloalkylalkyl, or aryl or arylalkyl (1–5 carbon atoms of the aryl ring may be replaced with N, O or S), or $R^k$ and $R^{k'}$ together with the atoms that connect them form a ring system (which can also contain additional N, O or S atoms and which can be saturated or unsaturated).

2. Featured Classes of Compounds of the Invention

One class of compounds which is of special interest consists of compounds as are described just above in Part 1, in which the phosphorus-containing moiety in $R^B$ comprises an aliphatic, heteroaliphatic, aryl, or heteroaryl group which contains at least one of the substituents set forth in Series II:

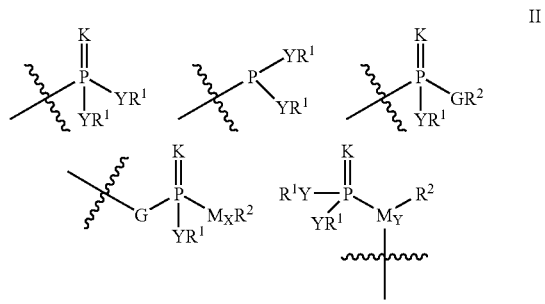

II wherein each occurrence of K is independently —O— or —S—;
each occurrence of Y is independently —O—, —S—, —NR— or a chemical bond linking $R^1$ to P;
each occurrence of $R^1$ is independently a substituted or unsubstituted aliphatic, heteroaliphatic, aryl, or heteroaryl moiety, or, except in $YR^1$ moieties in which Y is a covalent bond, $R^1$ may also be H;
each occurrence of $R^2$ is independently $R^1$, —PK($YR^1$)($YR^1$), —SO$_2$($YR^1$) or —C(O)($YR^1$)
each occurrence of G is independently —O—, —S—, —NR— or $M_x$;
each occurrence of M is independently a substituted or unsubstituted methylene moiety, and any M–M' moiety may be electronically saturated or unsaturated;
each occurrence of x is independently an integer from 1–6; and,
each occurrence of $M_Y$ is independently a methine group or a lower alkyl moiety which contains a methine group and optionally may be further substituted.

When RB is aryl or heteroaryl, the phosphorus-containing moiety may be present at any available ring position. By way of example, attachment at the para position of an aryl ring is illustrated in the structures depicted in Series IIa(i) below.

The foregoing class of compounds is illustrated by the subclass thereof in which $R^B$ comprises an aliphatic, heteroaliphatic, aryl, or heteroaryl group containing at least one of the substituents set forth in Series IIa:

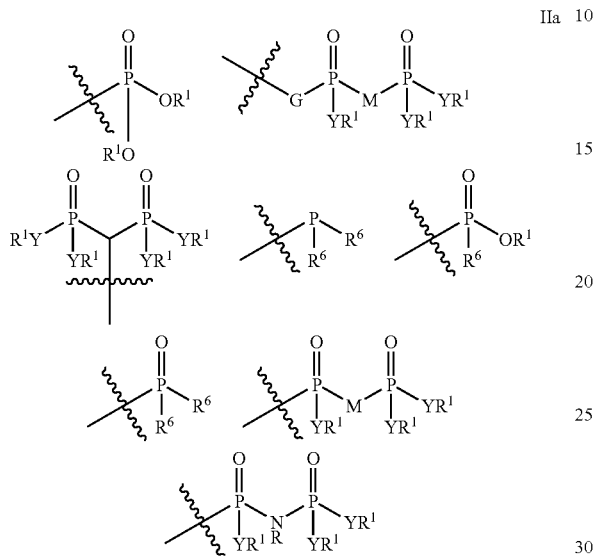

IIa in which each occurrence of $R^6$ is an independently selected aliphatic, heteroaliphatic, aryl, or heteroaryl moiety. This class and subclass are further exemplified by those compounds in which $R^1$ is H or lower alkyl; M is —$CH_2$—, —CH(OH)—, —CH(halo)—, or —C(halo)$_2$—; $R^6$ is lower alkyl and R is H. Halo and halogen represent fluorine, chlorine, bromine and iodine. The following structures illustrate several exemplary types of compounds of this subclass. Others will be readily apparent to the reader.

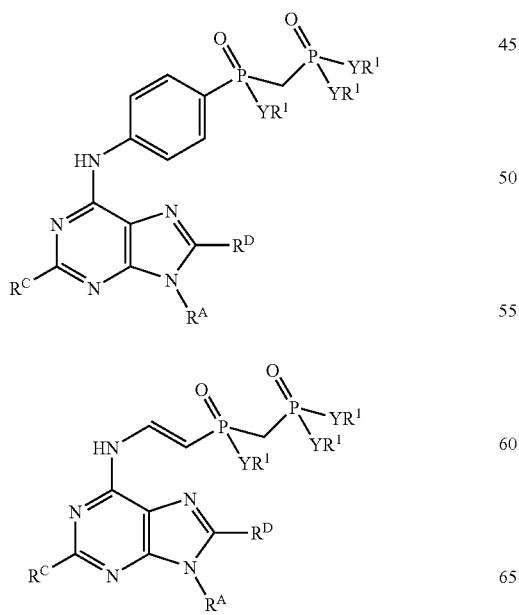

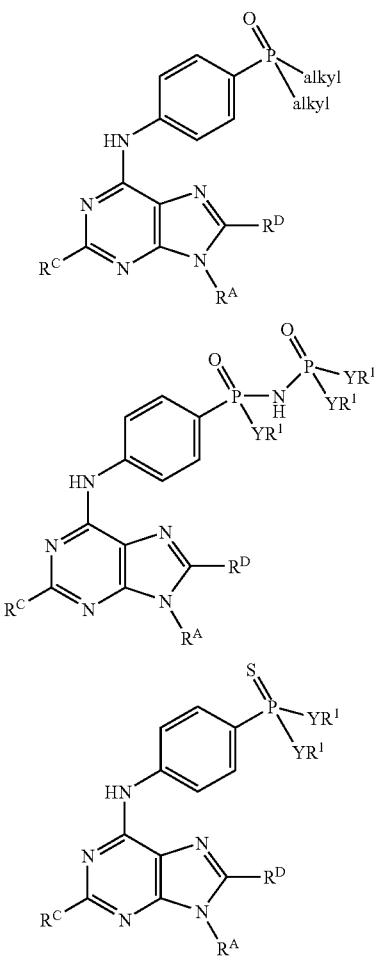

Another class of compounds of special interest consists of compounds as described in Part 1, in which the substituent, $R^B$, is any of the aryl or heteroaryl moieties of Series III:

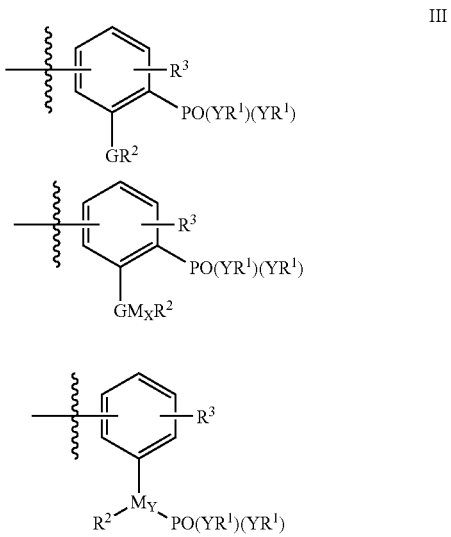

III

-continued

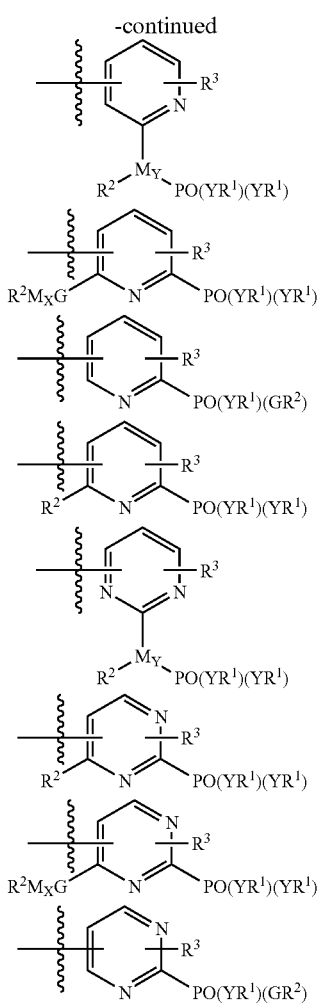

wherein each occurrence of Y is independently a covalent bond, —O—, —S— or —NR—; and each occurrence of R, $R^1$, $R^2$, G, M, x and $M_Y$ is as previously defined above; and each occurrence of $R^3$ independently represents from 0–3 substituents independently selected from the group consisting of halogen; R, —GR, —CO(YR), acylamino, amido, amidino, cyano, nitro, azido, sulfonyl, sulfoxido, sulfate, sulfonate, sulfamoyl, sulfonamido, and substituents of Series II.

Another class of compounds of special interest consists of compounds having the structure of Formula I in which $R^A$ is hydrogen, or an aliphatic, heteroaliphatic, aryl, or heteroaryl moiety;

$R^B$ comprises an aliphatic, heteroaliphatic, aryl, or heteroaryl moiety bearing at least one phosphorus-containing moiety;

$R^C$ is an aliphatic, heteroaliphatic, aryl, or heteroaryl moiety which is covalently attached through a C—C bond to the carbon atom at ring position 2 of the purine ring system of formula I;

$R^D$ is hydrogen or halogen, or is an aliphatic, heteroaliphatic, aryl, or heteroaryl moiety, or —ZR, so long as $R^D$ does not comprise (1) a substituted or unsubstituted arylene moiety (in which up to two methine carbons may be replaced by nitrogen atoms), a C3–7 cycloalkylene moiety (which may contain nitrogen atoms in place of up to two ring carbons), an indanylene moiety, or a 1,2,3,4-tetrahydronaphthylene moiety; and does not terminate in a cyano group or in an N-substituted or unsubstituted amino, amidino, guanidino or guanidinoalkyl group;

wherein in each of the foregoing groups each aliphatic or heteroaliphatic moiety may be branched or unbranched, cyclic or acyclic and substituted or unsubstituted, and each aryl and heteroaryl moiety may be substituted or unsubstituted.

Another class of compounds of special interest consists of compounds having the structure of Formula I in which $R^A$ is hydrogen, or an aliphatic, heteroaliphatic, aryl, or heteroaryl moiety;

$R^B$ comprises an aliphatic, heteroaliphatic, aryl, or heteroaryl moiety bearing at least one a substituent of Series IIb:

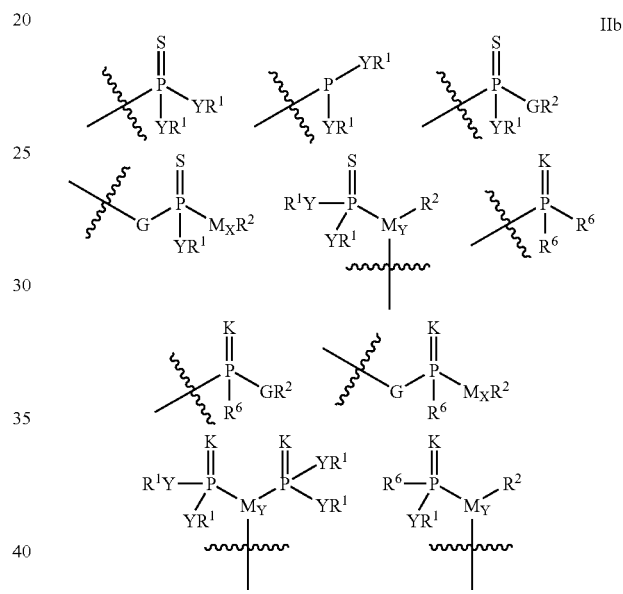

IIb $R^C$ is hydrogen, halogen, an aliphatic, heteroaliphatic, aryl, or heteroaryl moiety, or —ZR, wherein Z is —O—, —S—, or NR, wherein each occurrence of R without a further alphanumeric superscript is independently hydrogen, or a substituted or unsubstituted aliphatic, heteroaliphatic, aryl, or heteroaryl moiety;

$R^D$ is hydrogen or halogen, or is an aliphatic, heteroaliphatic, aryl, or heteroaryl moiety, or —ZR, so long as $R^D$ does not comprise (1) a substituted or unsubstituted arylene moiety (in which up to two methine carbons may be replaced by nitrogen atoms), a C3–7 cycloalkylene moiety (which may contain nitrogen atoms in place of up to two ring carbons), an indanylene moiety, or a 1,2,3,4-tetrahydronaphthylene moiety; and does not terminate in a cyano group or in an N-substituted or unsubstituted amino, amidino, guanidino or guanidinoalkyl group;

wherein in each of the foregoing groups each aliphatic or heteroaliphatic moiety may be branched or unbranched, cyclic or acyclic and substituted or unsubstituted, and each aryl and heteroaryl moiety may be substituted or unsubstituted.

Another class of compounds of special interest consists of compounds as described in the previous class, except that $R^D$ is hydrogen, halogen, or —YR, wherein Y is O, S, NR or a chemical bond, and R is a moiety which does not terminate in a cyano group or in an N-substituted or unsubstituted amino, amidino, guanidino or guanidinoalkyl group; and, wherein in each of the foregoing groups each aliphatic or heteroaliphatic moiety may be branched or unbranched, cyclic or acyclic and substituted or unsubstituted, and each aryl and heteroaryl moiety may be substituted or unsubstituted except as provided to the contrary.

Another class of compounds of special interest consists of compounds having the structure of Formula I in which
$R^A$ is hydrogen, or an aliphatic, heteroaliphatic, aryl, or heteroaryl moiety;
$R^B$ is an aliphatic, heteroaliphatic, aryl, or heteroaryl moiety which comprises one or more of the moieties of Series II or is one of the moieties of Series III;
$R^C$ is hydrogen, halogen, an aliphatic, heteroaliphatic, aryl, or heteroaryl moiety, or —ZR, wherein Z is —O—, —S—, or NR, wherein each occurrence of R without a further alphanumeric superscript is independently hydrogen, or a substituted or unsubstituted aliphatic, heteroaliphatic, aryl, or heteroaryl moiety;
$R^D$ is hydrogen, halogen, or —YR, wherein R is a moiety which does not terminate in a cyano group or in an N-substituted or unsubstituted amino, amidino, guanidino or guanidinoalkyl group;
wherein in each of the foregoing groups each aliphatic or heteroaliphatic moiety may be branched or unbranched, cyclic or acyclic and substituted or unsubstituted, and each aryl and heteroaryl moiety may be substituted or unsubstituted;
with the proviso that (1) at least one of $R^A$, $R^C$ or $R^D$ comprises a phosphorus-containing moiety; $R^C$ is covalently attached through a C—C bond to the carbon atom at ring position 2 of the purine ring system; or (3) $R^B$ comprises a phosphorus-containing moiety other than —P(O)$R^J R^{J'}$ where $R^J$ and $R^{J'}$ are independently OH, alkoxy, arylalkoxy, aryloxy, alkylcarbonyloxyalkoxy, arylalkylcarbonyloxyalkoxy, $NR^k R^{k'}$, mono- or di-alkylaminocarbonylmethyloxy, (di-aryl-alkylaminocarbonylmethyloxy, arylamino, a D- or L-amino acid, N-alkyl)piperidine-4yloxy, 2-methylsulfonylethoxy, 1,3 thiazole-2-ylmethyloxy, 3-pyridylmethyloxy, or 2-((di-alkyl)amino)ethoxy, where $R^k$ is H, alkyl, cycloalkyl, cycloalkylalkyl, or aryl or arylalkyl (1–5 carbon atoms of the aryl ring may be replaced with N, O or S), or $R^k$ and $R^{k'}$ together with the atoms that connect them form a ring system (which can also contain additional N, O or S atoms and which can be saturated or unsaturated).

Another class of compounds of special interest consists of compounds having the structure of Formula I in which
$R^D$ is hydrogen, halogen, or —YR, wherein R is a moiety which does not terminate in a cyano group or in an N-substituted or unsubstituted amino, amidino, guanidino or guanidinoalkyl group;
wherein in each of the foregoing groups each aliphatic or heteroaliphatic moiety may be branched or unbranched, cyclic or acyclic and substituted or unsubstituted, and each aryl and heteroaryl moiety may be substituted or unsubstituted;
with the proviso that (1) at least one of $R^A$, $R^C$ or $R^D$ comprises a phosphorus-containing moiety; $R^C$ is covalently attached through a C—C bond to the carbon atom at ring position 2 of the purine ring system; or (3) $R^B$ comprises a phosphorus-containing moiety other than —P(O)$R^J R^{J'}$ where $R^J$ and $R^{J'}$ are independently OH, alkoxy, arylalkoxy, aryloxy, alkylcarbonyloxyalkoxy, arylalkylcarbonyloxyalkoxy, $NR^k R^{k'}$, mono- or di-alkylaminocarbonylmethyloxy, (di-aryl-alkylaminocarbonylmethyloxy, arylamino, a D- or L-amino acid, N-alkyl)piperidine-4yloxy, 2-methylsulfonylethoxy, 1,3 thiazole-2-ylmethyloxy, 3-pyridylmethyloxy, or 2-((di-alkyl)amino)ethoxy, where $R^k$ is H, alkyl, cycloalkyl, cycloalkylalkyl, or aryl or arylalkyl (1–5 carbon atoms of the aryl ring may be replaced with N, O or S), or $R^k$ and $R^{k'}$ together with the atoms that connect them form a ring system (which can also contain additional N, O or S atoms and which can be saturated or unsaturated).

Another class of compounds of special interest consists of compounds having the structure of Formula I in which
$R^A$ is hydrogen, or an aliphatic, heteroaliphatic, aryl, or heteroaryl moiety;
$R^B$ is an aliphatic, heteroaliphatic, aryl, or heteroaryl moiety which comprises one or more phosphorus-containing moieties;
$R^C$ is a branched, unbranched or cyclic alkyl group bearing one or more substitutents; a branched, unbranched or cyclic alkoxy moiety substituted with one or more OR, NRR', or substituted aryl moieties; a branched, unbranched or cyclic alkene or alkenoxy moiety which may be optionally substituted with one or more substituents; or NRR' where R and R' are independently selected from substituted or unsubstituted aliphatic and substituted aryl moieties;

Another class of compounds of special interest consists of compounds having the structure of Formula I in which
$R^A$ is hydrogen; alkenyl; alkynyl; alkyl-; —$M_x$aryl where the aryl group contains at least one $R^3$ substituent (e.g., m-hydroxyphenethyl); —$M_x$heteroaryl which may be optionally substituted; or a substituted aryl or optionally substituted heteroaryl moiety;
$R^B$ is an aliphatic, heteroaliphatic, aryl, or heteroaryl moiety which comprises one or more phosphorus-containing moieties;
$R^C$ is hydrogen; halogen; an aliphatic, heteroaliphatic, aryl, or heteroaryl moiety; or —ZR, wherein Z is —O—, —S—, or NR, wherein each occurrence of R without a further alphanumeric superscript is independently hydrogen, or a substituted or unsubstituted aliphatic, heteroaliphatic, aryl, or heteroaryl moiety;
$R^D$ is hydrogen, halogen, or —YR, wherein R is a moiety which does not terminate in a cyano group or in an N-substituted or unsubstituted amino, amidino, guanidino or guanidinoalkyl group;
wherein in each of the foregoing groups each aliphatic or heteroaliphatic moiety may be branched or unbranched, cyclic or acyclic and substituted or unsubstituted, and each aryl and heteroaryl moiety may be substituted or unsubstituted;
with the proviso that (1) at least one of $R^A$, $R^C$ or $R^D$ comprises a phosphorus-containing moiety; $R^C$ is covalently attached through a C—C bond to the carbon atom at ring position 2 of the purine ring system; or (3) $R^B$ comprises a phosphorus-containing moiety other than —P(O)$R^J R^{J'}$ where $R^J$ and $R^{J'}$ are independently OH, alkoxy, arylalkoxy, aryloxy, alkylcarbonyloxyalkoxy, arylalkylcarbonyloxyalkoxy, $NR^k R^{k'}$, mono- or di-alkylaminocarbonylmethyloxy, (di-aryl-alkylaminocarbonylmethyloxy, arylamino, a D- or L-amino acid, N-alkyl)piperidine-4yloxy, 2-methylsulfonylethoxy, 1,3 thiazole-2-ylmethyloxy, 3-pyridylmethyloxy, or 2-((di-alkyl)amino)ethoxy, where $R^k$ is H, alkyl, cycloalkyl, cycloalkylalkyl, or aryl or arylalkyl (1–5 carbon atoms of the aryl ring may be replaced with N, O or S), or $R^k$ and $R^{k'}$ together with the atoms that connect them form a ring system (which can also contain additional N, O or S atoms and which can be saturated or unsaturated).

Another class of compounds of special interest consists of compounds having the structure of Formula I in which $R^A$ is hydrogen, or an aliphatic, heteroaliphatic, aryl, or heteroaryl moiety;

$R^B$ is an aliphatic, heteroaliphatic, aryl, or heteroaryl moiety which comprises one or more phosphorus-containing moieties;

$R^C$ is hydrogen, halogen, an aliphatic, heteroaliphatic, aryl, or heteroaryl moiety, or —ZR, wherein Z is —O—, —S—, or NR, wherein each occurrence of R without a further alphanumeric superscript is independently hydrogen, or a substituted or unsubstituted aliphatic, heteroaliphatic, aryl, or heteroaryl moiety;

$R^D$ is hydrogen, halogen, or —YR, wherein R is a moiety which does not terminate in a cyano group or in an N-substituted or unsubstituted amino, amidino, guanidino or guanidinoalkyl group;

at least one of $R^A$, $R^B$ and $R^C$ also contains an independently selected phosphorus-containing moiety;

wherein in each of the foregoing groups each aliphatic or heteroaliphatic moiety may be branched or unbranched, cyclic or acyclic and substituted or unsubstituted, and each aryl and heteroaryl moiety may be substituted or unsubstituted;

with the proviso that in compounds in which $R^C$ is H, OH, halogen, alkoxy or cycloalkoxy groups of 1 to 6 carbon atoms (which alkoxy and cycloalkoxy groups can be substituted with phenyl) or amine, which can be substituted with phenyl or with alkyl or cycloalkyl groups of 1 to 6 carbon atoms, and $R^A$ is benzyl, phenyl or C1–4 alkyl, optionally substituted with oxygen (e.g. in the form of an ether or alcohol), $R^B$ is a moiety other than a heteroatom- and halogen-substituted derivative of a 3 to 8 carbon cycloalkyl, a 1 to 10 carbon alkyl, a 6 to 13 carbon aryl, or a 7 to 14 carbon aralkyl moiety in which the heteroatom is selected from N, P, S and O.

Another class of compounds of special interest consists of compounds having the structure of Formula I in which $R^A$ is hydrogen, or an aliphatic, heteroaliphatic, aryl, or heteroaryl moiety;

$R^B$ is an aliphatic, heteroaliphatic, aryl, or heteroaryl moiety which comprises one or more of the moieties of Series II:

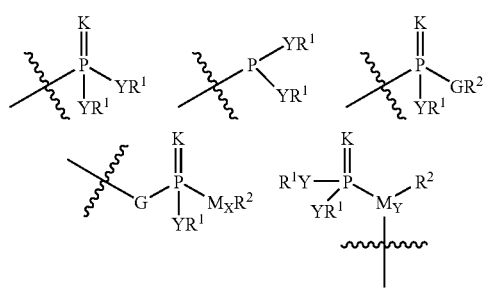

or is one of the moieties of Series III:

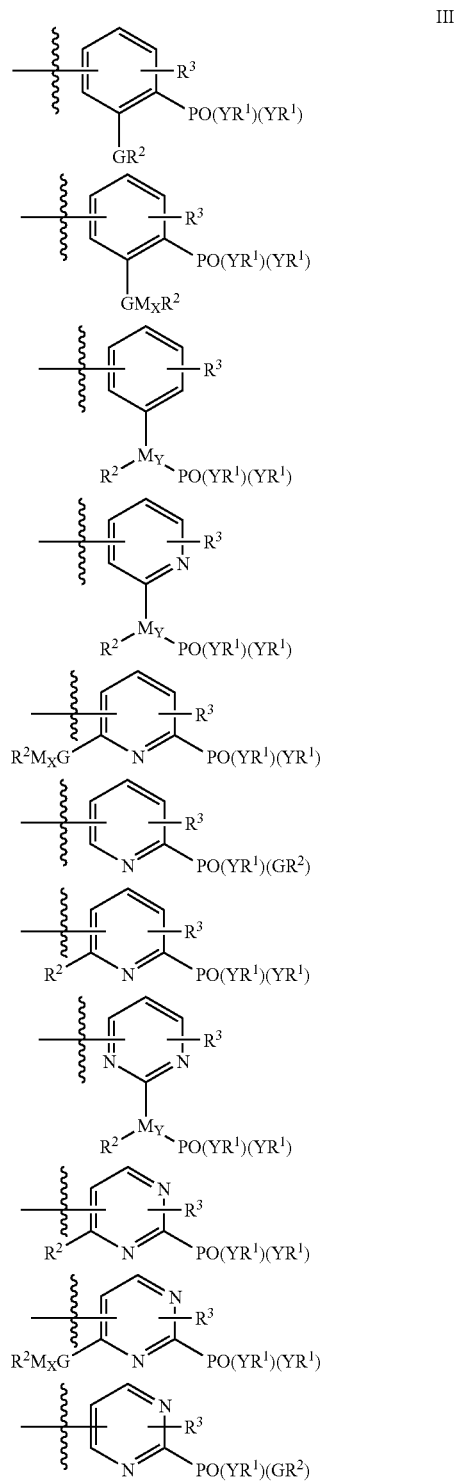

$R^C$ is hydrogen, halogen, an aliphatic, heteroaliphatic, aryl, or heteroaryl moiety, or —ZR, wherein Z is —O—, —S—, or NR, wherein each occurrence of R without a further alphanumeric superscript is independently hydrogen, or a substituted or unsubstituted aliphatic, heteroaliphatic, aryl, or heteroaryl moiety;

$R^D$ is hydrogen, halogen, or —YR, wherein R is a moiety which does not terminate in a cyano group or in an N-substituted or unsubstituted amino, amidino, guanidino or guanidinoalkyl group;

at least one of $R^A$, $R^B$ and $R^C$ also contains an independently selected phosphorus-containing moiety;

wherein in each of the foregoing groups each aliphatic or heteroaliphatic moiety may be branched or unbranched, cyclic or acyclic and substituted or unsubstituted, and each aryl and heteroaryl moiety may be substituted or unsubstituted.

Another class of compounds of special interest consists of compounds having the structure of Formula I in which $R^A$ is hydrogen, or an aliphatic, heteroaliphatic, aryl, or heteroaryl moiety;

$R^B$ is an aliphatic, heteroaliphatic, aryl, or heteroaryl moiety which comprises one or more phosphorus-containing moieties;

$R^C$ is a branched, unbranched or cyclic alkyl group bearing one or more substitutents; a branched, unbranched or cyclic alkoxy moiety substituted with one or more OR, NRR', or substituted aryl moieties; a branched, unbranched or cyclic alkene or alkenoxy moiety which may be optionally substituted with one or more substituents; or NRR' where R and R' are independently selected from substituted or unsubstituted aliphatic and substituted aryl moieties;

$R^D$ is hydrogen, halogen, or —YR, wherein R is a moiety which does not terminate in a cyano group or in an N-substituted or unsubstituted amino, amidino, guanidino or guanidinoalkyl group;

at least one of $R^A$, $R^B$ and $R^C$ also contains an independently selected phosphorus-containing moiety;

wherein in each of the foregoing groups each aliphatic or heteroaliphatic moiety may be branched or unbranched, cyclic or acyclic and substituted or unsubstituted, and each aryl and heteroaryl moiety may be substituted or unsubstituted.

Another class of compounds of special interest consists of compounds having the structure of Formula I in which $R^A$ is hydrogen; alkenyl; alkynyl; alkyl- or alkenyl-aryl where the aryl group contains at least one substituent, $R^3$; or a substituted aryl or heteroaryl moiety;

$R^B$ is an aliphatic, heteroaliphatic, aryl, or heteroaryl moiety which comprises one or more phosphorus-containing moieties;

$R^C$ is hydrogen, halogen, an aliphatic, heteroaliphatic, aryl, or heteroaryl moiety, or —ZR, wherein Z is —O—, —S—, or NR, wherein each occurrence of R without a further alphanumeric superscript is independently hydrogen, or a substituted or unsubstituted aliphatic, heteroaliphatic, aryl, or heteroaryl moiety;

$R^D$ is hydrogen, halogen, or —YR, wherein R is a moiety which does not terminate in a cyano group or in an N-substituted or unsubstituted amino, amidino, guanidino or guanidinoalkyl group;

at least one of $R^A$, $R^B$ and $R^C$ also contains an independently selected phosphorus-containing moiety;

wherein in each of the foregoing groups each aliphatic or heteroaliphatic moiety may be branched or unbranched, cyclic or acyclic and substituted or unsubstituted, and each aryl and heteroaryl moiety may be substituted or unsubstituted;

A number of important subclasses of the foregoing classes of compounds deserve separate mention. Those subclasses include subclasses of the foregoing classes in which:

(a) $R^D$ is H or halo;

(b) $R^C$ is covalently attached through a C—C bond to the carbon atom at ring position 2 of the purine ring system;

(c) the phosphorus-containing moiety of $R^B$ is present on an aryl or heteroaryl ring system;

(d) $R^A$ is lower aliphatic, and may be branched or unbranched, cyclic or acyclic, and optionally substituted with one or more substituents selected from a lower aliphatic group (which may be substituted or unsubstituted), —OR, —SR, —NRR', —C(O)YR, and —Y—C(O)Y'R, where Y is O, S, NR, or a bond and R is H or a substituted or unsubstituted aliphatic, heteroaliphatic, aryl, or heteroaryl moiety (For example, $R^A$ can be a lower aliphatic which may be substituted with one or more hydroxy, alkoxy, aralkoxy, carbamyl, amino, substituted amino, acyl, cyano, halogen, nitro or sulfo groups, and/or with one or more alkyl, alkenyl, alkynyl, cycloalkyl, aryl, heterocyclic, aryloxy or aralkyl moieties which may themselves be substituted with one or more hydroxy, alkoxy, aralkoxy, carbamyl, amino, substituted amino, acyl, cyano, halogen, nitro or sulfo groups. This includes the set of compounds in which $R^A$ is Mx-aryl or Mx-heterocycle where M is a substituted or unsubstituted methylene, x is an integer from 1 to 6, the aryl moiety may bear one or more substituents, and the heterocycle is a substituted or unsubstituted, aromatic or nonaromatic heterocyclic moiety comprising a 5- to 7-membered ring bearing one or more heteroatoms, including among others, embodiments in which $M_x$ is methyl, ethyl or propyl, and the aryl moiety is o-, m-, or p-hydroxy-, 2,3-dihydroxy-, 2,4-dihydroxy-, 2,5-dihydroxy-, 3,4-dihydroxy-, or 3,5-dihydroxyphenyl.);

(e) $R^C$ is —OR, where R is H, aliphatic, heteroaliphatic, aryl, or heteroaryl;

(f) $R^C$ is —R, —NR or —OR in which R is C1–C8 aliphatic, which may be branched or unbranched, cyclic or noncyclic, and which may be substituted with one or more hydroxy, alkoxy, aralkoxy, carbamyl, amino, substituted amino, acyl, cyano, halogen, nitro or sulfo groups, and/or with one or more alkyl, alkenyl, alkynyl, cycloalkyl, aryl, heterocyclic, aryloxy or aralkyl moieties which may themselves be substituted with one or more hydroxy, alkoxy, aralkoxy, carbamyl, amino, substituted amino, acyl, cyano, halogen, nitro or sulfo groups;

(g) $R^C$ is —R, —NR or —OR in which R comprises a C1–C8 aliphatic moiety substituted with one or more groups selected from the following: a substituted or unsubstituted amine or 5- to 7-membered heterocyclic moiety, which may itself be optinally substituted;

(h) $R^B$ comprises

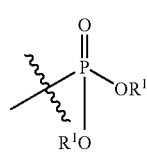

wherein each $R^1$ is independently H, alkyl, arylalkyl, aryl or a prodrug moiety;
(i) $R^B$ comprises

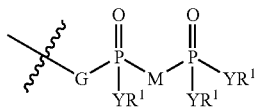

wherein each $R^1$ is independently H, alkyl, arylalkyl, aryl or a prodrug moiety;
(j) $R^B$ comprises

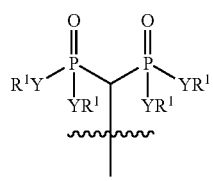

wherein each $R^1$ is independently H, alkyl, arylalkyl, aryl or a prodrug moiety;
(k) $R^B$ comprises

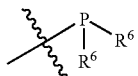

wherein each $R^6$ is independently alkyl, arylalkyl, aryl or a prodrug moiety;
(l) $R^B$ comprises

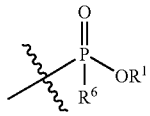

wherein $R^1$ is H, alkyl, arylalkyl or a prodrug moiety and $R^6$ is alkyl, arylalkyl, aryl or a prodrug moiety;
(m) $R^B$ comprises

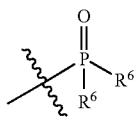

wherein each $R^6$ is independently alkyl, arylalkyl, aryl or a prodrug moiety;
(n) $R^B$ comprises

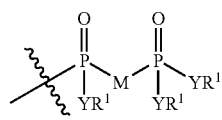

wherein each $R^1$ is H, alkyl, arylalkyl or a prodrug moiety, and Y and M are as defined previously;
(o) $R^B$ comprises

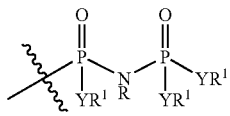

wherein each $R^1$ is independently H, alkyl, arylalkyl, aryl or a prodrug moiety and R is aliphatic, heteroaliphatic, aryl, or heteroaryl;
(p) the compounds are of Formula I and:
  $R^A$ is hydrogen, or an aliphatic, heteroaliphatic, aryl, or heteroaryl moiety;
  $R^C$ is hydrogen, halogen, an aliphatic, heteroaliphatic, aryl, or heteroaryl moiety, or —ZR, wherein Z is —O—, —S—, or NR, wherein each occurrence of R without a further alphanumeric superscript is independently hydrogen, or a substituted or unsubstituted aliphatic, heteroaliphatic, aryl, or heteroaryl moiety;
  $R^D$ is hydrogen, halogen, an aliphatic, heteroaliphatic, aryl, or heteroaryl moiety, or —ZR;
  $R^8$ is selected from the moieties of Series III or Series IIc:

IIc

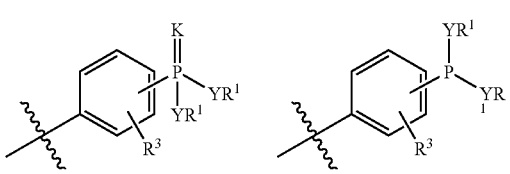

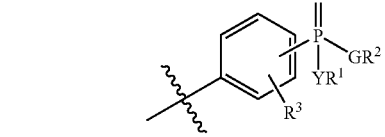

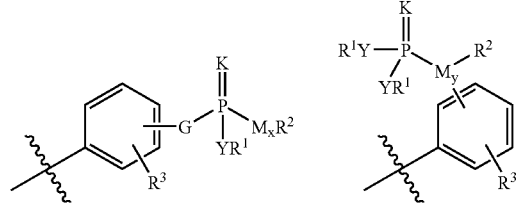

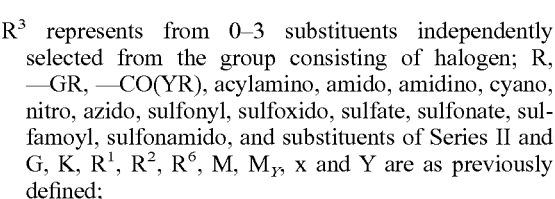

$R^3$ represents from 0–3 substituents independently selected from the group consisting of halogen; R, —GR, —CO(YR), acylamino, amido, amidino, cyano, nitro, azido, sulfonyl, sulfoxido, sulfate, sulfonate, sulfamoyl, sulfonamido, and substituents of Series II and G, K, $R^1$, $R^2$, $R^6$, M, $M_y$, x and Y are as previously defined;
wherein in each of the foregoing groups each aliphatic or heteroaliphatic moiety may be branched or unbranched, cyclic or acyclic and substituted or unsubstituted, and each aryl and heteroaryl moiety may be substituted or unsubstituted;
with the following provisos:
(A) (1) $R^D$ is a moiety other than one comprising a substituted or unsubstituted arylene moiety (in which up to two methine carbons may be replaced by nitrogen atoms), a C3–7 cycloalkylene moiety (which may contain nitrogen atoms in place of up to two ring carbons), an indanylene moiety, or a 1,2,3,4-tetrahydronaphthylene moiety; or (2) $R^D$ is a moiety other than one terminating in a cyano group or in an N-substituted or unsubstituted amino, amidino, guanidino or guanidinoalkyl group;

(B) (1) at least one of $R^A$, $R^C$ or $R^D$ comprises a phosphorus-containing moiety; $R^C$ is covalently attached through a C—C bond to the carbon atom at ring position 2 of the purine ring system; or (3) $R^B$ comprises a phosphorus-containing moiety other than —P(O)$R^J R^{J'}$ where $R^J$ and $R^{J'}$ are independently OH, alkoxy, arylalkoxy, aryloxy, alkylcarbonyloxy-alkoxy, arylalkylcarbonyloxyalkoxy, $NR^k R^{k'}$, mono- or di-alkylaminocarbonylmethyloxy, (di-aryl-alkylaminocarbonylmethyloxy, arylamino, a D- or L-amino acid, N-alkyl)piperidine-4yloxy, 2-methylsulfo-nylethoxy, 1,3 thiazole-2-ylmethyloxy, 3-pyridylmethyloxy, or 2-((di-alkyl)amino)ethoxy, where $R^k$ is H, alkyl, cycloalkyl, cycloalkylalkyl, or aryl or arylalkyl (1–5 carbon atoms of the aryl ring may be replaced with N, O or S), or $R^k$ and $R^{k'}$ together with the atoms that connect them form a ring system (which can also contain additional N, O or S atoms and which can be saturated or unsaturated).

As the reader will appreciate, compounds of particular interest include, among others, those which share the attributes of one or more of the foregoing subclasses.

Some of those subclasses are illustrated by the following sorts of compounds:

I. Compounds of the Formula:

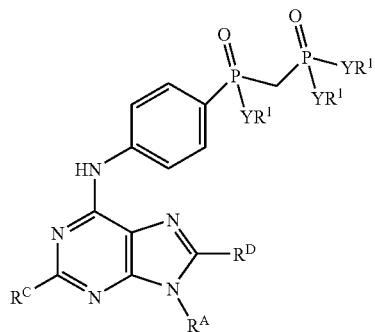

wherein $R^A$ is hydrogen, or an aliphatic, heteroaliphatic, aryl, or heteroaryl moiety;

$R^C$ is hydrogen, halogen, an aliphatic, heteroaliphatic, aryl, or heteroaryl moiety, or —ZR, wherein Z is —O—, —S—, or NR, wherein each occurrence of R without a further alphanumeric superscript is independently hydrogen, or a substituted or unsubstituted aliphatic, heteroaliphatic, aryl, or heteroaryl moiety;

$R^D$ is hydrogen, halogen, an aliphatic, heteroaliphatic, aryl, or heteroaryl moiety, or —ZR, with the proviso that $R^D$ does not terminate in a cyano group or in an N-substituted or unsubstituted amino, amidino, guanidino or guanidinoalkyl group; and, wherein in each of the foregoing groups each aliphatic or heteroaliphatic moiety may be branched or unbranched, cyclic or acyclic and substituted or unsubstituted, and each aryl and heteroaryl moiety may be substituted or unsubstituted.

II. Compounds of the Formula:

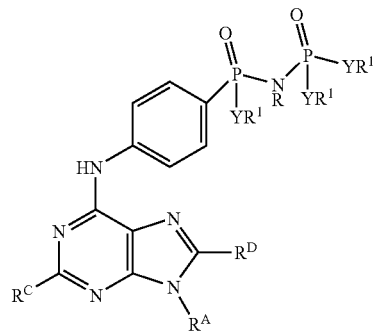

wherein $R^A$ is hydrogen, or an aliphatic, heteroaliphatic, aryl, or heteroaryl moiety;

$R^C$ is hydrogen, halogen, an aliphatic, heteroaliphatic, aryl, or heteroaryl moiety, or —ZR, wherein Z is —O—, —S—, or NR, wherein each occurrence of R without a further alphanumeric superscript is independently hydrogen, or a substituted or unsubstituted aliphatic, heteroaliphatic, aryl, or heteroaryl moiety;

$R^D$ is hydrogen, halogen, an aliphatic, heteroaliphatic, aryl, or heteroaryl moiety, or —ZR, with the proviso that $R^D$ does not terminate in a cyano group or in an N-substituted or unsubstituted amino, amidino, guanidino or guanidinoalkyl group and wherein in each of the foregoing groups each aliphatic or heteroaliphatic moiety may be branched or unbranched, cyclic or acyclic and substituted or unsubstituted, and each aryl and heteroaryl moiety may be substituted or unsubstituted.

III. Compounds of the Formula:

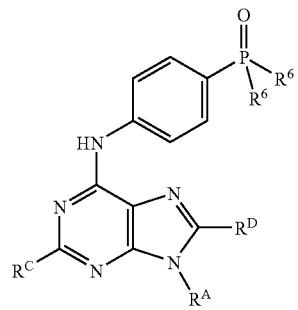

wherein $R^A$ is hydrogen, or an aliphatic, heteroaliphatic, aryl, or heteroaryl moiety;

$R^C$ is hydrogen, halogen, an aliphatic, heteroaliphatic, aryl, or heteroaryl moiety, or —ZR, wherein Z is —O—, —S—, or NR, wherein each occurrence of R without a further alphanumeric superscript is independently hydrogen, or a substituted or unsubstituted aliphatic, heteroaliphatic, aryl, or heteroaryl moiety;

$R^D$ is hydrogen, halogen, an aliphatic, heteroaliphatic, aryl, or heteroaryl moiety, or —ZR, with the proviso that $R^D$ does not terminate in a cyano group or in an N-substituted or unsubstituted amino, amidino, guanidino or guanidinoalkyl group; and wherein in each of the foregoing groups each aliphatic or heteroaliphatic moiety may be branched or unbranched, cyclic or acyclic and substituted or unsubstituted, and each aryl and heteroaryl moiety may be substituted or unsubstituted.

IV. Compounds of the Formula:

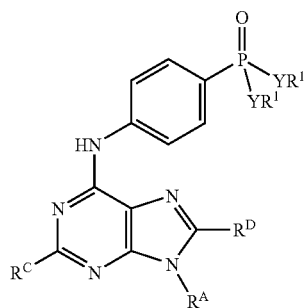

wherein $R^A$ is hydrogen, or an aliphatic, heteroaliphatic, aryl, or heteroaryl moiety;

$R^C$ is an aliphatic, heteroaliphatic, aryl, or heteroaryl moiety which is covalently attached through a carbon-carbon bond to the carbon atom at ring position 2 of the purine ring system;

$R^D$ is hydrogen, halogen, an aliphatic, heteroaliphatic, aryl, or heteroaryl moiety, or —ZR, with the proviso that $R^D$ does not terminate in a cyano group or in an N-substituted or unsubstituted amino, amidino, guanidino or guanidinoalkyl group; and wherein in each of the foregoing groups each aliphatic or heteroaliphatic moiety may be branched or unbranched, cyclic or acyclic and substituted or unsubstituted, and each aryl and heteroaryl moiety may be substituted or unsubstituted. In one subset of these compounds, $R^D$ is H. In another it is F. In another $R^C$ is aliphatic and contains an amino or hydroxy substituent.

Some of the foregoing compounds can exist in various isomeric forms. The invention encompasses the compounds as individual isomers substantially free of other isomers and, alternatively, as mixtures of various isomers, e.g. racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of this invention which are of particular interest include those which inhibit Src kinase or another kinase of interest with an IC50 value of 100 nM or less (as determined using any scientifically acceptable kinase inhibition assay), inhibit a given kinase with an IC50 value at least 100-fold lower than their IC50 values for other kinases of interest, measurably bind to bone preferentially over other tissues, detectably improve the balance of bone growth relative to bone resorption (in favor of bone growth) in any scientifically acceptable animal model, inhibit PTH-induced bone resorption in a scientifically acceptable animal model by at least 50% (relative to PTH-treated animals that did not receive the compound) when administered at doses of 25 mg compound/kg of animal weight once or twice daily, preferably at doses of 10 mg/kg, and more preferably at doses of 1 mg/kg or exibit a cytotoxic or growth inhibitory effect on cancer cell lines maintained in vitro or in animal studies using a scientifically acceptable cancer cell xenograft model.

This invention also provides a pharmaceutical preparation comprising at least one of the foregoing compounds or a pharmaceutically acceptable derivative thereof, as inhibitors of bone resorption by osteoclasts, as inhibitors of tumor growth and tumor metastasis, for the treatment and prophylaxis of diseases or undesirable conditions which are mediated by a kinase inhibited by said compound, and at least one pharmaceutically acceptable excipient or additive. Preferably the excipient or additive is pharmaceutically innocuous.

The invention further provides a method for inhibiting bone resorption, inhibiting tumor growth and/or tumor metastasis, or for the treatment and prevention of diseases or undesirable conditions which are mediated by a kinase inhibited by one of the foregoing compounds. The method involves administering a therapeutically effective amount of the compound or a pharmaceutically acceptable derivative thereof to a human or animal in need of it. Such administration constitutes a method for inhibiting bone resorption by osteoclasts, or for inhibiting tumor growth and/or tumor metastasis or other proliferative disease. Generally speaking, such administration comprises a method for the treatment and prophylaxis of diseases which are mediated by a kinase inhibited by one of the foregoing compounds or a pharmaceutically acceptable derivative thereof.

The compounds provided by this invention are also useful as standards and reagents in characterization of various kinases, especially but not limited to Src family kinases; the study of the role of such kinases in biological and pathological phenomena; the study of intracellular signal transduction pathways mediated by such kinases; the comparative evaluation of new kinase inhibitors; the study of various cancers in cell lines and animal models; and the study of bone biology, including the competing forces of resorption and generation of bone.

3. Compounds and Definitions

As discussed above, this invention provides a new family of compounds with a range of biological properties. Compounds of this invention have biological activities relevant for the treatment of diseases including bone related disorders and proliferative disease, including cancer. More generally the compounds are useful in the regulation of signal transduction pathways. For example, certain compounds of the invention are useful for inhibiting protein kinases, including in particular, the tyrosine kinase, Src.

Compounds of this invention comprise those set forth above, described herein, and illustrated in part by the various classes, subclasses and species disclosed elsewhere herein.

It will be appreciated by the reader of ordinary skill in the art that asymmetric centers may exist in the compounds of the present invention. Thus, compounds of the invention and pharmaceutical compositions thereof may be in the form of an individual enantiomer, diastereomer or geometric isomer, or may be in the form of a mixture of stereoisomers. In certain embodiments, the compounds of the invention are enantiopure compounds, substantially free from other enantiomers. In certain other embodiments, a mixture of stereoisomers or diastereomers are obtained.

Additionally, the present invention provides pharmaceutically acceptable derivatives of the foregoing compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

Certain compounds of the present invention, and definitions of specific functional groups are also described in more detail below. For purposes of this invention, the chemical elements are identified in accordance with the Periodic Table of the Elements, CAS version, Handbook of Chemistry and Physics, 75$^{th}$ Ed., inside cover, and specific functional groups are defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, can utilize a variety of protecting groups. By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other funcational groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties, as is noted in connection with particular classes, subclasses or species of the invention. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. Generally speaking, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment of bone related disorders and cancer or for the inhibition of one or more protein kinases. The term "stable", as used herein, preferably refers to compounds which possess stability sufficient to allow manufacture and which maintain the integrity of the compound for a sufficient period of time to be detected, and preferably for a sufficient time to be useful for one or more of the purposes detailed herein.

The term "aliphatic", as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes both straight, branched and cyclic alkyl groups. An analogous convention applies to other generic terms such as "alkenyl", "alkynyl" and the like. The reader should note that while the terms "alkyl", "alkenyl", "alkynyl" and the like are often used to describe otherwise unsubstituted hydrocarbons, this document uses those terms, with reference to the compounds of this invention, to encompass both substituted and unsubstituted groups.

Unless otherwise specified, alkyl and other aliphatic groups preferably contain 1–8, and often 1–3, contiguous aliphatic carbon atoms. Illustrative aliphatic groups thus include, but are not limited to, for example, methyl, ethyl, allyl, n-propyl, isopropyl, cyclopropyl, —CH$_2$-cyclopropyl, methallyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Benzyl, phenethyl, heteroaromatic analogs, and substituted derivatives of such moieties are thus considered substituted aliphatic moieties. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alkoxy", or "thioalkyl" as used herein refers to an alkyl group, as previously defined, attached to the parent molecular moiety through an oxygen atom or through a sulfur atom. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to methylthio, ethylthio, propylthio, isopropylthio, n-butylthio, and the like.

The term "alkylamino" refers to a group having the structure —NHR' wherein R' is alkyl, as defined herein. Examples of alkylamino include, but are not limited to, methylamino, ethylamino, iso-propylamino and the like. In certain embodiments, $C_1$–$C_3$ alkylamino groups are utilized in the present invention.

Some examples of substituents of the above-described aliphatic (and other) moieties of compounds of the invention include, but are not limited to: F, Cl, Br, I, OH, $NO_2$, CN, C(O)-alkyl, C(O)-aryl, C(O)-heteroaryl, $CO_2$-alkyl, $CO_2$-aryl, $CO_2$-heteroaryl, $CONH_2$, CONH-alkyl, CONH-aryl, CONH-heteroaryl, OC(O)-alkyl, OC(O)-aryl, OC(O)-heteroaryl, $OCO_2$-alkyl, $OCO_2$-aryl, $OCO_2$-heteroaryl, $OCONH_2$, OCONH-alkyl, OCONH-aryl, OCONH-heteroaryl, NHC(O)-alkyl, NHC(O)-aryl, NHC(O)-heteroaryl, $NHCO_2$-alkyl, $NHCO_2$-aryl, NHCONH-heteroaryl, $SO_2$-alkyl, $SO_2$-aryl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, alkoxy, methoxymethoxy, methoxyethoxy, amino, benzylamino, arylamino, heteroarylamino, -alkyl-amino, thio, aryl-thio, heteroarylthio, benzyl-thio, alkyl-thio, or methylthiomethyl. Additional examples of generally applicable substitutents are illustrated by the specific embodiments shown in the Examples which are described herein.

In general, the terms "aryl" and "heteroaryl", as used herein, refer to stable mono- or polycyclic, heterocyclic, polycyclic, and polyheterocyclic unsaturated moieties having preferably 3–14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one, two or three of the hydrogen atoms thereon independently with any one or more of the following moieties including, but not limited to: F, Cl, Br, I, OH, $NO_2$, CN, C(O)-alkyl, C(O)-aryl, C(O)-heteroaryl, $CO_2$-alkyl, $CO_2$-aryl, $CO_2$-heteroaryl, $CONH_2$, CONH-alkyl, CONH-aryl, CONH-heteroaryl, OC(O)-alkyl, OC(O)-aryl, OC(O)-heteroaryl, $OCO_2$-alkyl, $OCO_2$-aryl, $OCO_2$-heteroaryl, $OCONH_2$, OCONH-alkyl, OCONH-aryl, OCONH-heteroaryl, NHC(O)-alkyl, NHC(O)-aryl, NHC(O)-heteroaryl, $NHCO_2$-alkyl, $NHCO_2$-aryl, NHCONH-heteroaryl, $SO_2$-alkyl, $SO_2$-aryl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, alkoxy, methoxymethoxy, methoxyethoxy, amino, benzylamino, arylamino, heteroarylamino, alkyl-amino, thio, aryl-thio, heteroarylthio, benzyl-thio, alkyl-thio, or methylthiomethyl. Additional examples of generally applicable substitutents are illustrated by the specific embodiments shown in the Examples which are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or hetercyclic moieties, may optionally be substituted. F, Cl, Br, I, OH, $NO_2$, CN, C(O)-alkyl, C(O)-aryl, C(O)-heteroaryl, $CO_2$-alkyl, $CO_2$-aryl, $CO_2$-heteroaryl, $CONH_2$, CONH-alkyl, CONH-aryl, CONH-heteroaryl, OC(O)-alkyl, OC(O)-aryl, OC(O)-heteroaryl, $OCO_2$-alkyl, $OCO_2$-aryl, $OCO_2$-heteroaryl, $OCONH_2$, OCONH-alkyl, OCONH-aryl, OCONH-heteroaryl, NHC(O)-alkyl, NHC(O)-aryl, NHC(O)-heteroaryl, $NHCO_2$-alkyl, $NHCO_2$-aryl, NHCONH-heteroaryl, $SO_2$-alkyl, $SO_2$-aryl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, alkoxy, methoxymethoxy, methoxyethoxy, amino, benzylamino, arylamino, heteroarylamino, alkyl-amino, thio, aryl-thio, heteroarylthio, benzyl-thio, alkyl-thio, or methylthiomethyl. Additional examples of generally applicable substitutents are illustrated by the specific embodiments shown in the Examples which are described herein.

The term "heteroaliphatic", as used herein, refers to aliphatic moieties which contain one or more oxygen, sulfur, nitrogen, phosphorous or silicon atoms, e.g., in place of carbon atoms. Heteroaliphatic moieties may be branched, unbranched or cyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to: F, Cl, Br, I, OH, $NO_2$, CN, C(O)-alkyl, C(O)-aryl, C(O)-heteroaryl, $CO_2$-alkyl, $CO_2$-aryl, $CO_2$-heteroaryl, $CONH_2$, CONH-alkyl, CONH-aryl, CONH-heteroaryl, OC(O)-alkyl, OC(O)-aryl, OC(O)-heteroaryl, OCO$_2$-alkyl, OCO$_2$-aryl, OCO$_2$-heteroaryl, OCONH$_2$, OCONH-alkyl, OCONH-aryl, OCONH-heteroaryl, NHC(O)-alkyl, NHC(O)-aryl, NHC(O)-heteroaryl, NHCO$_2$-alkyl, NHCO$_2$-aryl, NHCONH-heteroaryl, SO$_2$-alkyl, SO$_2$-aryl, C$_3$–C$_6$-cycloalkyl, CF$_3$, CH$_2$CF$_3$, CHCl$_2$, CH$_2$OH, CH$_2$CH$_2$OH, CH$_2$NH$_2$, CH$_2$SO$_2$CH$_3$, aryl, heteroaryl, benzyl, benzyloxy, aryloxy, heteroaryloxy, alkoxy, methoxymethoxy, methoxyethoxy, amino, benzylamino, arylamino, heteroarylamino, alkyl-amino, thio, aryl-thio, heteroarylthio, benzyl-thio, alkyl-thio, or methylthiomethyl. Additional examples of generally applicable substitutents are illustrated by the specific embodiments shown in the Examples which are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to: F, Cl, Br, I, OH, NO$_2$, CN, C(O)-alkyl, C(O)-aryl, C(O)-heteroaryl, CO$_2$-alkyl, CO$_2$-aryl, CO$_2$-heteroaryl, CONH$_2$, CONH-alkyl, CONH-aryl, CONH-heteroaryl, OC(O)-alkyl, OC(O)-aryl, OC(O)-heteroaryl, OCO$_2$-alkyl, OCO$_2$-aryl, OCO$_2$-heteroaryl, OCONH$_2$, OCONH-alkyl, OCONH-aryl, OCONH-heteroaryl, NHC(O)-alkyl, NHC(O)-aryl, NHC(O)-heteroaryl, NHCO$_2$-alkyl, NHCO$_2$-aryl, NHCONH-heteroaryl, SO$_2$-alkyl, SO$_2$-aryl, C$_3$–C$_6$-cycloalkyl, CF$_3$, CH$_2$CF$_3$, CHCl$_2$, CH$_2$OH, CH$_2$CH$_2$OH, CH$_2$NH$_2$, CH$_2$SO$_2$CH$_3$, aryl, heteroaryl, benzyl, benzyloxy, aryloxy, heteroaryloxy, alkoxy, methoxymethoxy, methoxyethoxy, amino, benzylamino, arylamino, heteroarylamino, alkylamino, thio, aryl-thio, heteroarylthio, benzyl-thio, alkyl-thio, or methylthiomethyl. Additional examples of generally applicable substitutents are illustrated by the specific embodiments shown in the Examples which are described herein.

"Phosphorus containing moiety" As used herein, the phrase, "phosphorus containing moiety" includes, but is not limited to, phosphites, phosphonites, phosphenites, phosphines, phosphates, phophonates, phosphenates, phosphine oxides bisphosphonates, thiophosphates, thiophosphonates, thiophosphenates, thiophosphine oxides, mono- or (where permited) di- or tri-amides and esters of any of the foregoing as well as the phosphorus-containing moieties disclosed in Series II, IIa, IIb, IIc and III and the accompanying text and in the various classes, subclasses and species of compounds disclosed herein.

4. Synthetic Overview

The practitioner has a a well-established literature of purine chemistry to draw upon, in combination with the information contained in the many examples which follow, for guidance on synthetic strategies, protecting groups, and other materials and methods useful for the synthesis of the compounds of this invention, including compounds containing R$^A$, R$^B$, R$^C$ and R$^D$ substituents. The following references, and the references cited therein, may be of particular interest: U.S. Pat. Nos. 5,365,886; 5,434,150; 5,565,566; 5,869,468; 6,057,305; 5,444,068; 5,635,525; 5,866,702; 5,962,479; 6,057,326; 5,994,361; 6,110,923; 6,028,076; 6,084,095; and 6,107,300; WO 00/43394, 90/09178, 00/44750, 97/49689, 95/35297, 95/19774, 97/35539, 97/16452, 00/49018, 97/20842, 98/16528, 99/07705, 99/62908 and 00/55161; and EP 155911, 478292, 531597, 853084, 454427, 778277, 773023, and 882727.

Various solution phase and solid phase syntheses are disclosed in detail in the examples which follow which provide interesting and helpful examples of many representative chemical transformations and total syntheses.

Solution phase transformations include, among others, schemes based on the following:

A. Attachment of an aliphatic moiety to ring atom #2 of a purine:

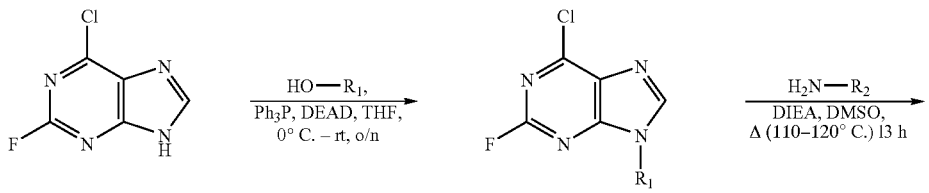

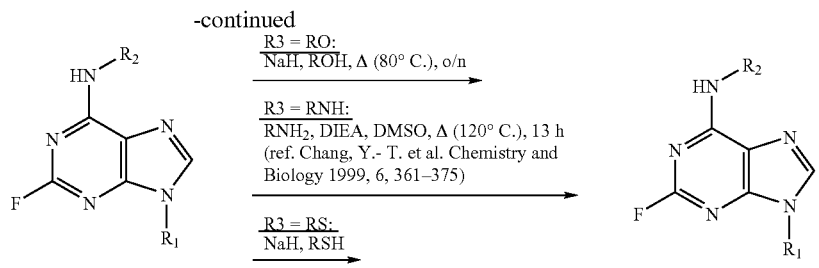
This approach provides a generic means for attaching an aliphatic moiety to purine position 2 through a carbon-carbon bond.
B. Preparation of thio analogs
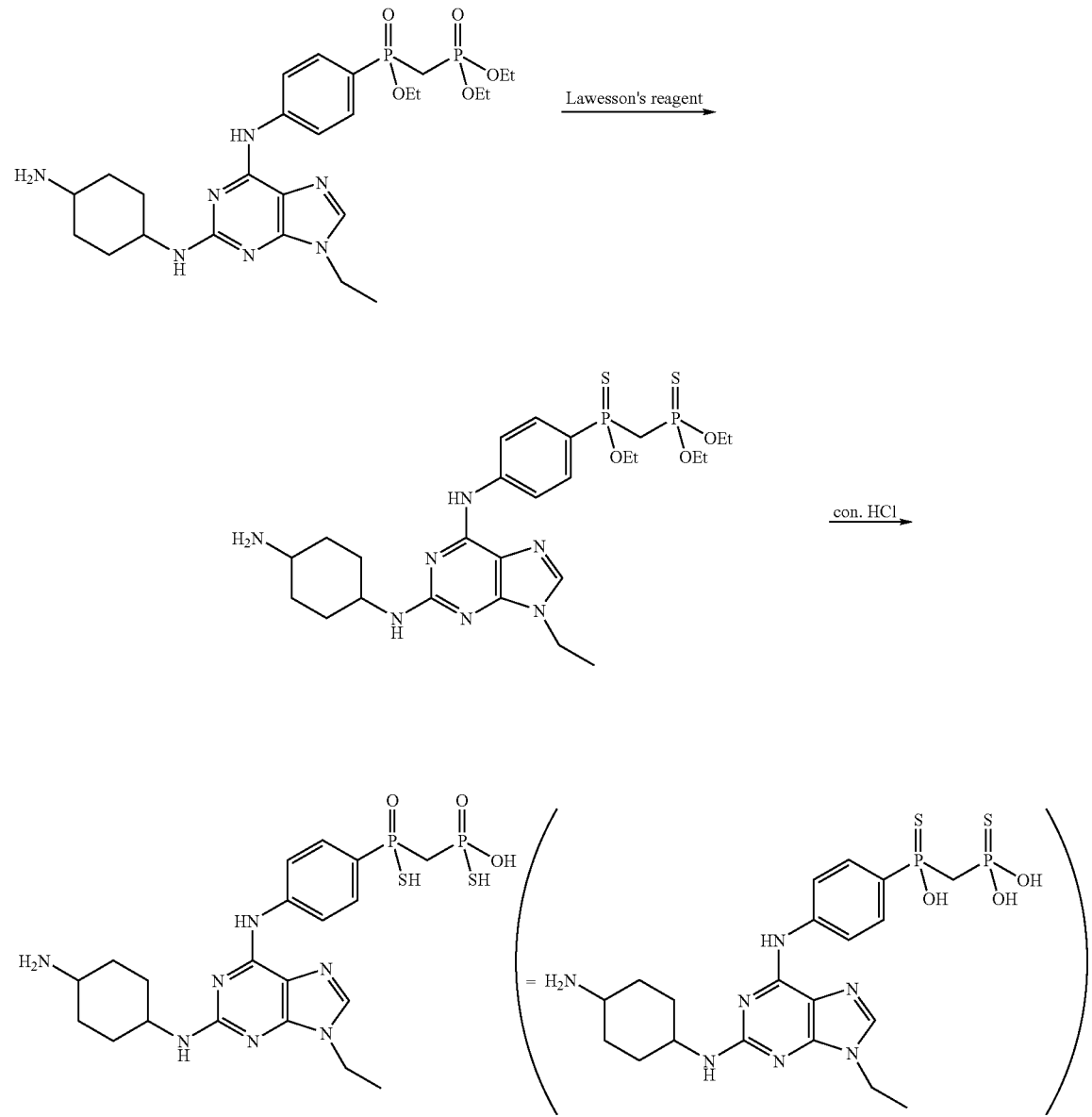
Ref. Can. J. Chem. 1999, 77(7), 1274–1280.

-continued
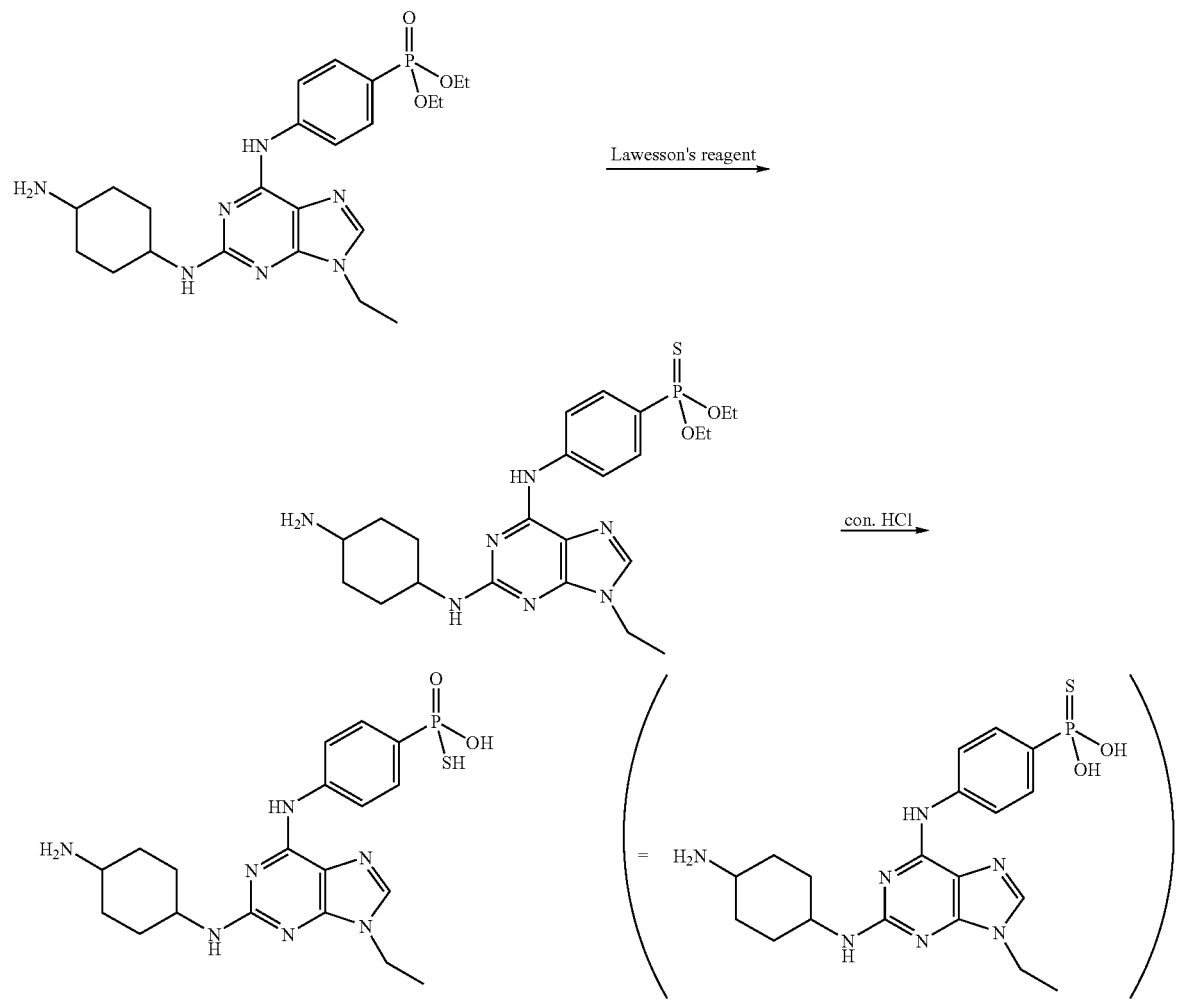
Ref. Can. J. Chem. 1999, 77(7), 1274–1280.
C. Elaboration of $R^C$ moieties
Synthetic scheme:
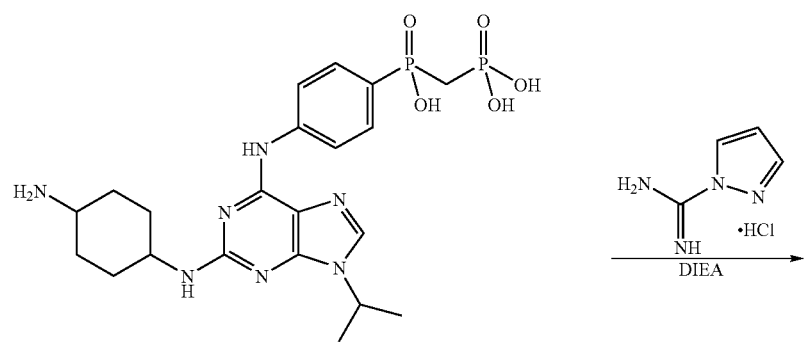

-continued

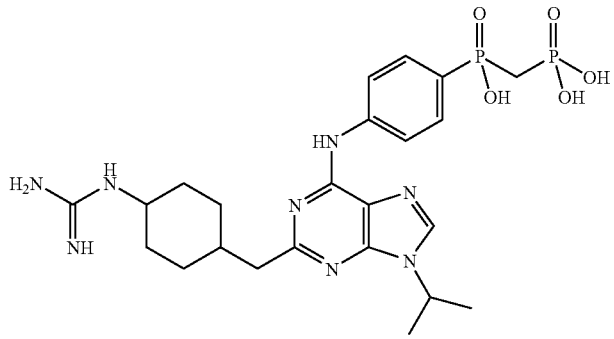

other examples:

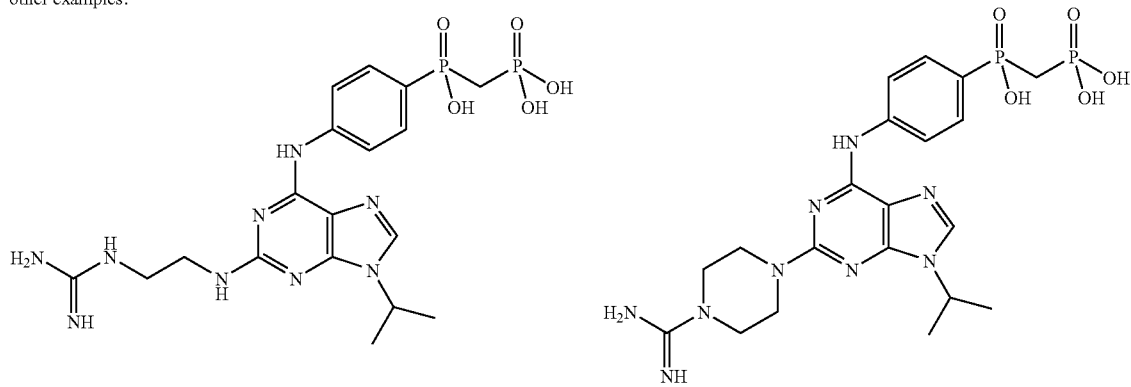

Other illustrative anionic groups:

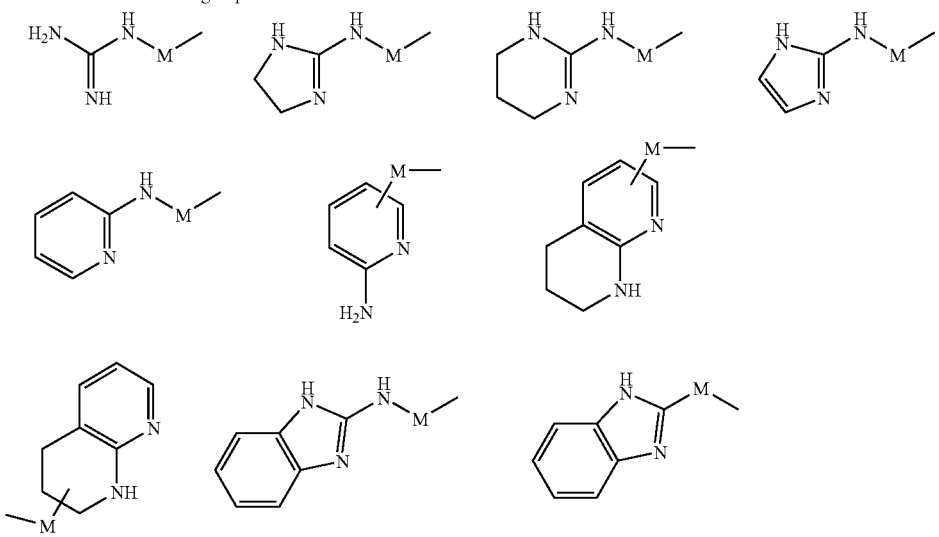

In the scheme above, M is a spacer between purine and the anionic group and can be a substituted or unsubstituted aliphatic, heteroaliphatic, aryl or heteroaryl, thus providing C—C, O—C, N—C and S—C linkages to the carbon atom at purine ring position 2. To illustrate further, a 1-amino-2-haloethane can be N-protected with a conventional Boc group, then converted to the Znhalo reagent, attached to a desired 2-iodopurine by the route shown in scheme A above, then deprotected. The same route may be used for aliphatic moieties bearing other substituents (proctected as appropriate).

D. Preparation of "P—N—P" Moieties $(R^1O)_2PO$—NR—$PO(OR^1)_2$-containing compounds may be prepared from the corresponding amines using $(RO)_2$ CIP as described in Phosphorus, Sulfur Silicon Relat. Elem. 91(1–4), 169–77 (1994).

Additional synthetic guidance is provided in the Examples which follow, just before the claims.

5. Prodrugs

Numerous suitable prodrug moieties, and information concerning their selection, synthesis and use are well known, beginning with lower alkyl esters of phosphonates and related moieties. Other prodrug moieties of interest include the following:

a compound of this invention may be an anticancer agent, or an approved agent for the treatment of a bone disorder, as discussed in more detail herein.

| R | |
|---|---|
| 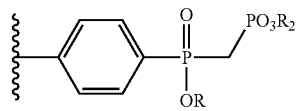 | |
| 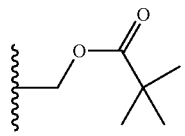 | Atack, J. R. et al. J. of Pharmacology and Experimental Therapeutics 1994, 270, 70. |
| 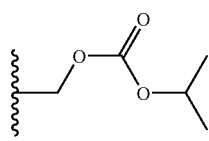 | Arimilli, M. N., et al. Antiviral Chemistry & Chemotherapy 1997, 8, 557. |
| 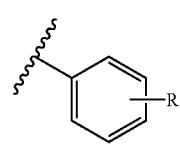 | Serafinowska, H. T., et al J. Med. Chem. 1995, 35, 1372. |
| 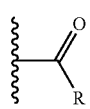 | Ahlmark, M., J. Med. Chem. 1999, 42, 1473. |
| 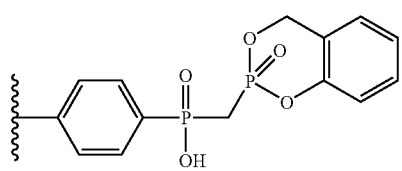 | Meier, C., et al. J. Med. Chem. 1998, 41, 1417. |

Review: Krise, J. P., Stella, V. J. Advanced Drug Delivery Reviews 1996, 19, 287. and references cited therein.

6. Uses, Formulations, Administration

Pharmaceutical Compositions

As discussed above this invention provides novel compounds which have biological properties which make them of interest for the treatment of bone disorders and cancer. Those biological properties include among others, anti-resorption activity in various bone resorption assays and activity against cancer cells. Accordingly, in another aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts of phosphonates and other phosphorus-containing compounds, amines, carboxylic acids, and other types of compounds, are well known in the art. For example, S. M. Berge, et al. describe pharmaceutically acceptable salts in detail in *J. Pharmaceutical Sciences*, 66:

1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-viral compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds of the Invention

As discussed herein, the compounds of the present invention have been shown to inhibit tyrosine kinase activity of Src, among other tyrosine kinases (see exemplification herein). Various compounds of the invention have been shown to inhibit osteoclast activity and to tilt the balance of bone resorption and bone growth positively, i.e., away from net bone loss. As such, the compounds of the invention may be useful in the treatment of bone disorders. It is currently preferred that the compounds used for such indications be compounds of this invention that have one or more free OH or SH groups on or adjacent to the phosphorus-containing moiety or moieties which characterize these compounds. Thus, such compounds will often contain one or more —YR$^1$ moieties in which R$^1$ is H. Alternatively, prodrugs of such compounds may also be chosen. In any event, a therapeutically effective amount of a compound of the invention is administered to a subject in need thereof as a method for treating the subject's bone disorder.

A number of compounds of the invention have also been found to possess potent in vitro activity against cancer cell lines, including among others K-562 leukemia cells, NCI-H249 Lung cancer cells, T-47D mammary tumor cells and many others. Observed potencies have been as low as roughly 0.1 μM in conventional in vitro assays. Such compounds may thus be useful for treating cancer and additionally provides methods for the inhibition of cellular (preferably tumor) growth and provides methods for the killing of tumor cells. The method of the invention comprises administering to a subject in need thereof a therapeutically effective amount of a compound of the invention. It is currently preferred that in one or more of any —YR$^1$ groups present in the compound for this indication, that R$^1$ be other than H.

In certain embodiments of the present invention a "therapeutically effective amount" of the inventive compound or pharmaceutical composition is that amount effective for detectable killing or inhibiting the growth of tumor cells, or is an amount that is effective for inhibiting osteoclast activity, which activity is believed to be involved in the effect of bone disorders, although the present invention is not intended to be bound by any particular theory.

The compounds and compositions, according to the method of the present invention, may be administered using any amount and any route of administration effective for killing or inhibiting the growth of tumor cells, or for treating bone disorders. Thus, the expression "effective amount" as used herein, refers to a sufficient amount of agent to kill or inhibit the growth of tumor cells or to treat and/or prevent bone disorders. The exact amount required will vary from subject to subject, depending on the species, age, and general condition of the subject, the severity of the infection, the particular anticancer agent, its mode of administration, and the like. The anticancer compounds of the invention are preferably formulated in dosage unit form for ease of administration and uniformity of dosage. The expression "dosage unit form" as used herein refers to a physically discrete unit of anticancer agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As discussed above, in one aspect, the compounds of the present invention are useful as anticancer agents, and thus may be useful in the treatment of cancer, by effecting tumor cell death or inhibiting the growth of tumor cells. In general, the inventive anticancer agents are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In still other embodiments, the inventive anticancer agents are active against solid tumors and also kill and/or inhibit the growth of multidrug resistant cells (MDR cells).

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or anticancer agents that may be used in combination with the inventive anticancer agents of the present invention include surgery, radiotherapy (in but a few examples, g-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

As discussed above, in another aspect, the compounds of the present invention are useful in the selective treatment or prevention of bone disorders, and may effect treatment via inhibition of osteoclast activity, promotion of osteoblast activity, or promotion or inhibition of other cellular events necessary for healthy bone metabolism. In certain preferred embodiments, these compounds are useful for the treatment or prevention of diseases and conditions associated with bone metabolic disorders such as osteoclast overactivity. In still other preferred embodiments, the compounds of the present invention are targeted Src kinase inhibitors and thus inhibit bone resorption by osteoclasts.

The present invention therefore provides a method for the treatment, prophylaxis, and/or prevention of bone and other related disorders which method comprises the administration of an effective non-toxic amount of an inventive compound, or a pharmaceutically composition thereof. As mentioned above, although the inventive compounds effect treatment via several mechanisms, (i.e. inhibition of osteoclast activity, promotion of osteoblast activity, or regulation of other cellular events necessary for healthy bone metabolism), in certain preferred embodiments, these compounds are selective inhibitors of osteoclast activity.

In a further aspect, the present invention provides an inhibitor of mammalian osteoclasts, for example any one of the compounds of the present invention or a pharmaceutical composition thereof. In still another aspect, the present invention provides compounds or pharmaceutical compositions that are selective Src kinase inhibitors. In particular, the method of present invention comprises providing any one of the compounds of the present invention or a pharmaceutically composition thereof, for use in the treatment of and/or prophylaxis of osteoporosis and related osteopenic diseases.

It will be appreciated that, in addition to the treatment or prevention of osteoporosis, particularly osteoporosis associated with the peri and post menopausal conditions, the present invention also contemplates the treatment and prophylaxis or prevention of Paget's disease, hypercalcemia associated with bone neoplasms and other types of osteoporotic diseases and related disorders, including but not limited to involutional osteoporosis, Type I or postmenopausal osteoporosis, Type II or senile osteoporosis, juvenile osteoporosis, idiopathic osteoporosis, endocrine abnormality, hyperthyroidism, hypogonadism, ovarian agensis or Turners syndrome, hyperadrenocorticism or Cushing's syndrome, hyperparathyroidism, bone marrow abnormalities, multiple myeloma and related disorders, systemic mastocytosis, disseminated carcinoma, Gaucher's disease, connective tissue abnormalities, osteogenesis imperfecta, homocystinuria, Ehlers-Danlos syndrome, Marfan's syndrome, Menke's syndrome, immobilization or weightlessness, Sudeck's atrophy, chronic obstructive pulmonary disease, chronic heparin administration, and chronic ingestion of anticonvulsant drugs Treatment Kits In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the substituted purine dosages, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance which can be adapted to the practice of this invention in its various embodiments and the equivalents thereof.

EXAMPLES

Example 1

[(3-Amino-propyl)-ethoxy-phosphinoylmethyl]-phosphonic Acid Diethyl Ester

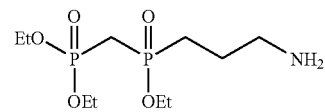

[(3-Benzyloxy-propyl)-ethoxy-phosphinoylmethyl]-phosphonic Acid Diethyl Ester:

To an oven-dried flask was added 10.25 g (44.7 mmol) of (3-Bromo-propoxymethyl)-benzene and 7.67 mL (44.7 mmol) of triethyl phosphite. The flask was fitted with a short-path distillation head, for removal of bromoethane, and the mixture heated at 150° C. for 4 h. The reaction was cooled to ambient temperature, and then diluted with 120 mL of absolute ethanol and 1.8 N KOH (120 mL, 216 mol). The distillation head was replaced with a reflux condenser and the solution heated at reflux for 5 h. The reaction was cooled then concentrated in vacuo. The basic aqueous layer was extracted with EtOAc (2x) and then acidified to pH 3 with conc. HCl. The aqueous layer was extracted with EtOAc (3x) and the combined extracts were dried over MgSO$_4$ and concentrated. The resulting crude product (8.24 g) was used as is in the next reaction. $^{31}$P NMR (300 MHz, DMSO-d$_6$) δ 34.113.

To a solution of the crude phosphonate (8.24 g, 32.5 mmol) in 100 mL CH$_2$Cl$_2$, under an atmosphere of N$_2$, was added 10.8 mL (113.8 mmol) of oxalyl chloride. DMF (several drops) was slowly added to initiate the reaction. After gas evolution had ceased, the reaction was stirred for 30 min at ambient temperature. Upon concentration in vacuo, the residue was titurated several times with hexane, then dissolved in 167 mL of anhydrous THF. In a separate flask, a cooled (−78° C., under N$_2$) solution of diethyl methylphosphonate (10.25 mL, 69.9 mmol) in 337 mL of anhydrous THF was added 2.5 M n-butyl lithium (27.95 mL, 69.9 mmol) dropwise. The reaction mixture was stirred for 30 min at −78° C., at which time the in situ generated acid chloride was added dropwise. The solution was stirred for an additional 2.5 h at −78° C., quenched with 5 mL glacial acetic acid, and then warmed to ambient temperature. Water was added to the reaction mixture and the THF was removed in vacuo. The aqueous layer was extracted with EtOAc (3×) and the combined organics washed with saturated NaHCO$_3$, brine, then dried over MgSO$_4$ and concentrated. The crude product was purified by silica gel chromatography (eluted with 50:1 CH$_2$Cl$_2$/MeOH) affording 6.15 g of a yellow oil. $^{31}$P NMR (300 MHz, DMSO-d$_6$) δ 51.479, 26.291.

[(3-Amino-propyl)-ethoxy-phosphinoylmethyl]-phosphonic Acid Diethyl Ester:

To a solution of [(3-Benzyloxy-propyl)-ethoxy-phosphinoylmethyl]-phosphonic acid diethyl ester (5.7 g, 14.5 mmol) in 100 mL of EtOH was added 1.2 g of palladium on carbon. The mixture was flushed with H$_2$ and stirred at ambient temperature (H$_2$ balloon) for 1 h. The reaction mixture was filtered through Celite and the solvent evaporated to provide 3.5 g of a pale yellow oil. $^{31}$P NMR (300 MHz, DMSO-d$_6$) d 52.219, 26.317.

To a cooled (0° C., under N$_2$) solution of the crude alcohol (3.5 g, 14.5 mmol) in 53 mL of CH$_2$Cl$_2$ was added 2.4 mL (17.4 mmol) of triethylamine followed by 1.25 mL (16 mmol) of methanesulfonyl chloride. The reaction mixture was warmed to ambient temperature and stirred for 1 h. The reaction mixture was then quenched with water and the layers separated. The organic layer was washed with water and brine, dried over Na$_2$SO$_4$, and concentrated. The crude orange-yellow oil (5.5 g) was used as is in the next reaction. $^{31}$P NMR (300 MHz, DMSO-d$_6$) δ 51.135, 26.614.

To a solution of the crude mesylate (5.5 g, 14.4 mmol) in 17 mL DMF was added 4.7 g (72.4 mmol) of sodium azide. The resulting slurry was heated at 55° C. and stirred overnight. The reaction mixture was diluted with EtOAc and washed with water (2×). The combined organics were then dried over Na$_2$SO$_4$ and concentrated. The crude azide (2.61 g) was used as is in the next reaction. $^{31}$P NMR (300 MHz, DMSO-d$_6$) d 51.230, 26.183.

To a solution of the crude azide (2.61 g, 8 mmol) in 100 mL of EtOH was added 0.8 g of palladium on carbon. The mixture was flushed with H$_2$ and stirred at ambient temperature (H$_2$ balloon) for 16 h. The reaction mixture was filtered through Celite and the solvent evaporated to provide 2.3 g of a yellow oil: $^1$H NMR (300 MHz, DMSO-d$_6$) δ 4.03 (m, 6H), 2.84–2.52 (m, 4H), 1.91–1.80 (m, 2H), 1.65–1.61 (m, 2H), 1.23 (m,9H). $^{31}$P NMR (300 MHz, DMSO-d$_6$) δ 51.757, 26.344.

Example 2

[(4-Amino-phenyl)-ethoxy-phosphinoylmethyl]-phosphonic Acid Diethyl Ester

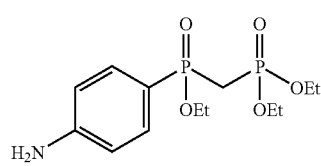

[(4-Nitro-phenyl)-ethoxy-phosphinoylmethyl]-phosphonic Acid Diethyl Ester:

A mixture of diethyl (ethoxyphosphinyl)methylphosphonate (2.35 g, 9.62 mmol), Et$_3$N (3.8 mL, 27.5 mmol), 1-iodo-4-nitrobenzene (2.28 g, 9.17 mmol) and Pd(PPh$_3$)$_4$ (265 mg, 0.229 mmol) in CH$_3$CN (14 mL) under N$_2$ was stirred at 80° C. for 2.5 h. After cooling to rt, the reaction mixture was poured into 50 mL of 1 N aq HCl and extracted with CH$_2$Cl$_2$. The extract was washed with H$_2$O (50 mL) and brine (50 mL). The aqueous washes were reextracted once with CH$_2$Cl$_2$, and the combined extracts were dried over Na$_2$SO$_4$ and concentrated. The crude material was purified by flash chromatography on silica gel. Elution with 30:1 CHCl$_3$-MeOH followed by 20:1 CHCl$_3$-MeOH and finally 15:1 CHCl$_3$-MeOH afforded 3.28 g of the desired (arylphosphinylmethyl)phosphonate.

[(4-Amino-phenyl)-ethoxy-phosphinoylmethyl]-phosphonic Acid Diethyl Ester:

A mixture of [(4-nitro-phenyl)-ethoxy-phosphinoylmethyl]-phosphonic acid diethyl ester (940 mg, 2.57 mmol) and SnCl$_2$.2H$_2$O (2.9 g, 12.9 mmol) in EtOH (~10 mL) was stirred at 70° C. for 44 min and then concentrated at ambient temperature. The residue was taken up in CH$_2$Cl$_2$ and washed with half saturated aq NaHCO$_3$ (40 mL), H$_2$O (40 mL) and brine (40 mL). The aqueous washes were reextracted once with CH$_2$Cl$_2$, and the combined extracts were dried over K$_2$CO$_3$ and concentrated. The crude material was purified by flash chromatography on silica gel. Elution with 20:1 CHCl$_3$-MeOH followed by 15:1 CHCl$_3$-MeOH afforded 657 mg of product.

Example 3

Synthesis of Phenyl Dialkyl Phosphine Oxides

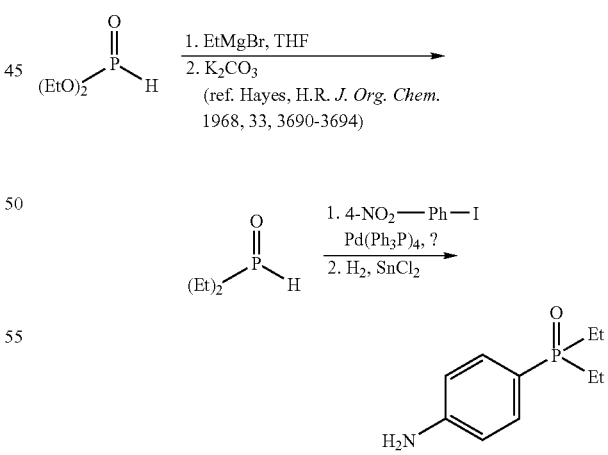

Example 4

In one embodiment, compounds as disclosed and described herein can be synthesized by solution-phase methods according to the scheme outlined below:

Solution-Phase Purine Synthetic Scheme

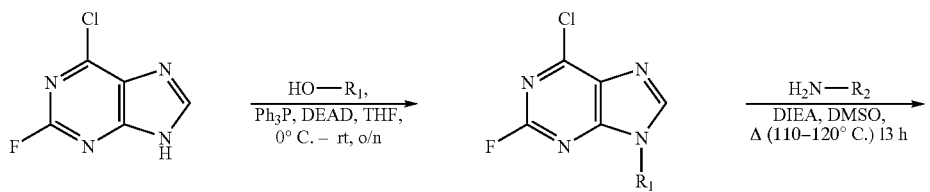

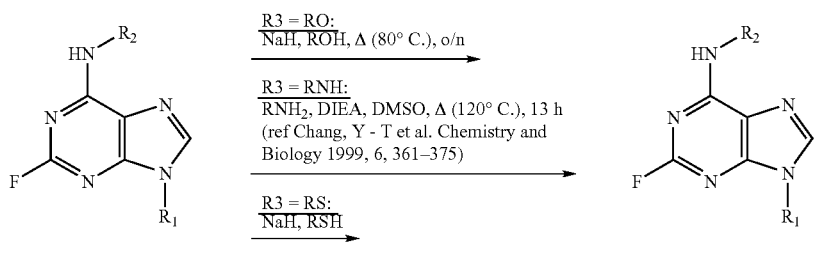

Example 5

({2-[6-(3-Chloro-phenylamino)-9-isopropyl-9H-purin-2-ylamino]-ethoxy}-hydroxy-phosphorylmethy)-phosphonic Acid

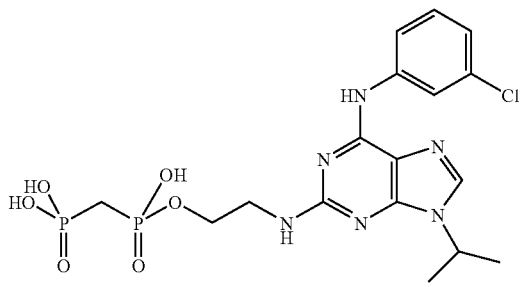

6-Chloro-2-fluoro-9H-purine:

A 0.3 M aqueous solution of $NaNO_2$ (200 mL, 60 mmol) was added dropwise to a cooled (−15° C.), vigorously stirred suspension of 2-amino-6-chloro-9H-purine (6.0 g, 35.4 mmol) in 120 mL $HBF_4$ (48 w % in $H_2O$, 0.92 mol) over 75 min. The pale yellow reaction was stirred at r. t. for 20 min and then recooled to −15° C. and neutralized to PH=6.0 with aqueous NaOH (50 w % in $H_2O$). The water was removed in vacuo and the resulting orange solid chromatographed on silica gel (90:10 $CH_2Cl_2$:MeOH, Rf 0.50). The final product was obtained as white solid (3.0 g, 49.1%).

6-Chloro-2-fluoro-9-isopropyl-9H-purine:

6-Chloro-2-fluoro-9H-purine (517.7 mg, 3 mmol), 2-propanol (198.3 mg, 3.3 mmol), $PPh_3$ (866 mg, 3.3 mmol) was mixed under $N_2$ in a 50 mL round-bottom flask at 0° C. DEAD (575 mg, 3.3 mmol) was added via syringe dropwise to the mixture. The temperature was raised to r. t. and the mixture was stirred overnight. Sovent was removed in vacuo and the resulting residue was chromatographed on silica gel ($CH_2Cl_2$/EtOAc, 4:1, Rf 0.62). The product was obtained as a white solid (411 mg, 64%).

(3-Chlorophenyl)-(2-fluoro-9-isopropyl-9H-purin-6-yl)amine:

6-Chloro-2-fluoro-9-isopropyl-9H-purine (214 mg, 1 mmol) was mixed with 3-chloroaniline (127.6 mg, 1 mmol) in 12 mL n-BuOH. DIEA (357.6 mg, 2.8 mmol) was added and the solution was heated at 90° C. overnight. Solvent was removed in vacuo and the residue was chromatographed on silica gel ($CH_2Cl_2$/EtOAc 2:2, Rf 0.44) to get the product as a white solid (148 mg, 48%).

2-(6-(3-chlorophenylamino-9-isopropyl-9H-purin-2-ylamino)ethanol:

(3-Chlorophenyl)-(2-fluoro-9-isopropyl-9H-purin-6-yl)amine (92 mg, 0.3 mmol) and ethanolamine (92 mg, 1.5 mmol) was mixed in 5 mL nBuOH/DMSO (4/1 v/v) and heated at 120° C. overnight. Solvent was removed in vacuo. The residue was chromatographed on silica gel (EtOAc, Rf 0.45) to get the product as a greenish solid (24 mg, 90%).

({2-[6-(3-Chloro-phenylamino)9-isopropyl-9H-purin-2-ylamino]-ethoxy}-hydroxy-phosphorylmethyl)-phosphonic Acid:

2-(6-(3-chlorophenylamino-9-isopropyl-9H-purin-2-ylamino)ethanol (180 mg, 0.52 mmol) was dissolved in 3 mL trimethyl phosphate at 0° C. Methylenebis(phosphonic dichloride) (514 mg, 2.1 mmol) was added in one portion and the reaction was stirred at 0° C. for 16 hrs. The solution was neutralized with 5 N ammonia to PH 6.0. The resulting mixture was purified by RP HPLC. Lyophilization left a white solid (147 mg, 56%).

Example 6

({2-[6-(3-Chloro-phenylamino)-9-isopropyl-9H-purin-2-ylamino]-3-methyl-butoxy}-hydroxy-phosphorylmethyl)-phosphonic Acid

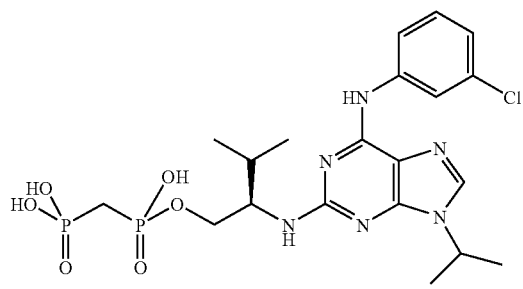

The title compound was synthesized in a manner similar to that described in Example 5. ES-MS: m/z 546 (M–H).

Example 7

({3-[6-(3-Chloro-phenylamino)-9-isopropyl-9H-purin-2-ylamino]-propoxy}-hydroxy-phosphorylmethyl)-phosphonic Acid

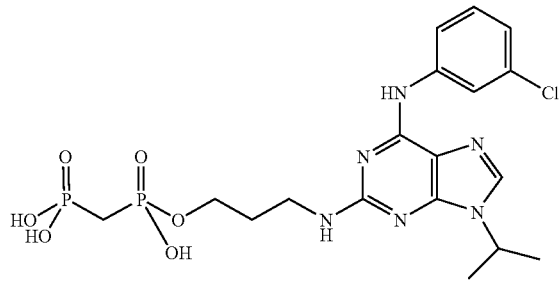

The title compound was synthesized in a manner similar to that described in Example 5. ES-MS: m/z 518 (M–H).

Example 8

({4-[6-(3-Chloro-phenylamino)-9-isopropyl-9H-purin-2-ylamino]-butoxy}-hydroxy-phosphorylmethyl)-phosphonic Acid

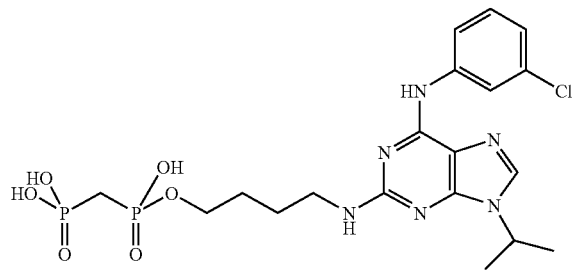

The title compound was synthesized in a manner similar to that described in Example 5. ES-MS: m/z 532 (M–H).

Example 9

({2-[6-(3-Chloro-phenylamino)-9-isopropyl-9H-purin-2-ylamino]-3-methyl-butoxy}-hydroxy-phosphorylmethyl)-phosphonic Acid

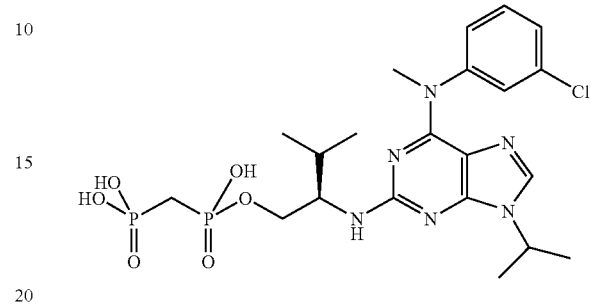

The title compound was synthesized in a manner similar to that described in Example 5. ES-MS: m/z 560 (M–H).

Example 10

({2-[6-(3-Chloro-phenylamino)-9-methyl-9H-purin-2-ylamino]-3-methyl-butoxy}-hydroxy-phosphorylmethyl)-phosphonic Acid

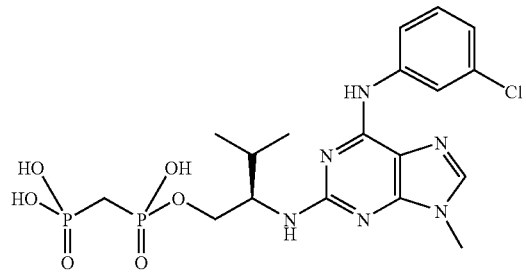

The title compound was synthesized in a manner similar to that described in Example 5. ES-MS: m/z 518 (M–H).

Example 11

[(4-{2-Ethoxy-9-[2-(3-hydroxy-phenyl)-ethyl]-9H-purin-6-ylamino}-phenyl)-hydroxy-phospinoylmethyl]-phosphonic Acid

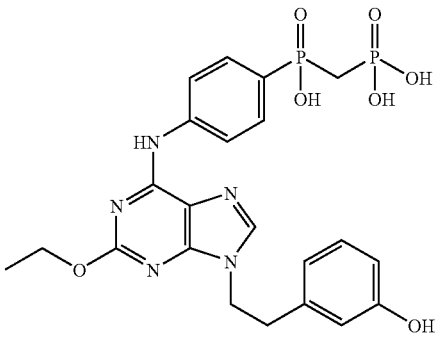

2-[3-(tert-Butyl-dimethyl-silanyloxy)-phenyl]-ethanol:

To a solution of 3-hydroxyphenethyl alcohol (6.0 g, 43.4 mmol) in 275 mL of $CH_2Cl_2$ was added 6.55 g (43.4 mmol) of TBDMS-Cl (tert-butyldimethylsilyl chloride), cooled to 0° C., then added 7.0 mL (86.8 mmol) of pyridine. The reaction mixture was stirred at ambient temperature overnight. Upon concentration, the crude mixture was purified by silica gel flash chromatography (eluted with hexane then 5% EtOAc/hexane) to provide 8.9 g of a clear oil: $^1$H NMR (300 MHz, DMSO-$d_6$) δ 9.17 (s, 1H), 7.04 (m, 1H), 6.60 (m, 3H), 3.73 (t, J=6.9 Hz, 2H), 2,65 (t, J=6.9 Hz, 2H), 0.83 (s, 9H), −0.03 (s, 6H).

9-{2-[3-(tert -Butyl-dimethyl-silanyloxy)-phenyl]-ethyl}-6-chloro-2-fluoro-9H-purine:

To a flask containing 1.26 g (7.3 mmol) of 6-chloro-2-fluoro-9H-purine and 3.82 g (14.6 mmol) of triphenylphosphine, under an atmosphere of $N_2$, was added a solution of 2-[3-(tert-Butyl-dimethyl-silanyloxy)-phenyl]- (3.7 g, 14.6 mmol) in 40 mL of THF. To the cooled (0° C.) reaction mixture was added a solution of diethyl azodicarboxylate (2.3 mL, 14.6 mmol) in 40.0 mL of THF and the resulting solution allowed to stir to ambient temperature overnight. Upon quenching with $H_2O$ (~1.0 mL), the solvent was removed and the crude mixture was purified by silica gel flash chromatography (eluted with 10% EtOAc/hexane then 15% EtOAc/hexane) to provide 1.71 g of a white solid: $^1$H NMR (300 MHz, DMSO-$d_6$) δ 8.52 (s, 1H), 7.11 (t, J=7.8 Hz, 1H), 6.76 (d, J=7.6 Hz, 1H), 6.65–6.62 (m, 1H), 6.49 (m, 1H), 4.48 (t, J=6.8 Hz, 2H), 3.12 (t, J=6.8 Hz, 2H), 0.88 (s, 9H), 0.06 (s, 6H); $^{19}$F NMR (DMSO-$d_6$) δ −48.23.

[(4-Amino-phenyl)-hydroxy-phosphinoylmethyl]-phosphonic Acid:

A solution of [(4-Amino-phenyl)-ethoxy-phosphinoylmethyl]-phosphonic acid diethyl ester (2.78 g, 8.29 mmol) in 250 mL of conc. HCl was heated at reflux (apparatus equipped with a NaOH trap) for 5 h. Concentrated solution via distillation to provide a sticky yellow-white solid, which was used without purification in the next step: m/z 252 (M+H).

[(4-{2-Fluoro-9-[2-(3-hydroxy-phenyl)-ethyl]-9H-purin-6-ylamino}-phenyl)-hydroxy-phosphinoylmethyl]-phosphonic Acid:

A sealed pressure flask, flushed with $N_2$, containing a mixture of crude [(4-Amino-phenyl)-hydroxy-phosphinoylmethyl]-phosphonic acid (8.29 mmol), 9-{2-[3-(tert-Butyl-dimethyl-silanyloxy)-phenyl]-ethyl}-6-chloro-2-fluoro-9H-purine (3.37 g, 8.29 mmol), and N,N-diisopropylethylamine (7.2 mL, 41.5 mmol) in 45.0 mL DMSO was heated at 110–120° C. for 13 h. Upon removing excess N,N-diisopropylethylamine ($N_2$ flow, slight heat) the slightly brown solution was cooled to ambient temperature and added ~500 mL of $H_2O$ to produce a milky, off-white solution. Further precipitation occurred upon addition of TFA (final pH=1–2), at which time the mixture was heated (100° C. hot plate) and stirred vigorously for ~20 min, filtered while hot, then washed with acidified $H_2O$ (TFA, pH=1–2; 4×20 mL), EtOH (2×20 mL), and $Et_2O$ (4×20 mL). Isolation of a second crop from the concentrated filtrate in the same manner as described above, followed by removal of excess solvent (in vacuo) provided 2.47 g of an off-white solid: m/z 506 (M−H).

[(4-{2-Ethoxy-9-[2-(3-hydroxy-phenyl)-ethyl]-9H-purin-6-ylamino}-phenyl)-hydroxy-phosphinoylmethyl]-phosphonic Acid:

To a cooled flask (0° C.) under an atmosphere of $N_2$ containing 0.096 g (4.02 mmol) of sodium hydride was added 2.0 mL of absolute ethanol. After the effervescence had ceased, the solution was transferred via pipette to a cooled (0° C.) pressure flask, under an atmosphere of $N_2$, containing a mixture of [(4-{2-Fluoro-9-[2-(3-hydroxy-phenyl)-ethyl]-9H -purin-6-ylamino}-phenyl)-hydroxy-phosphinoylmethyl]-phosphonic acid (0.199 g, 0.39 mmol) in 2.0 mL of absolute ethanol. Upon sealing the reaction vessel, the resulting mixture was stirred at ambient temperature for ~10 min, then heated at 80° C. overnight. Ethanol was removed via $N_2$ flow (slight heat) and the resulting thick suspension was dissolved in 25 mL of $H_2O$ (adjusted to pH ~8 with 10% NaOH), filtered (0.2 µm, PTFE filter), and purified by RP-HPLC ($CH_3CN/H_2O$). Lyophilization provided a white solid (0.105 g): m/z 532 (M−H).

Example 12

[Hydroxy-(4-{9-[2-(3-hydroxy-phenyl)-ethyl]-2-methoxy-9H -purin-6-ylamino}-phenyl)-phosphinoylmethyl]-phosphonic Acid

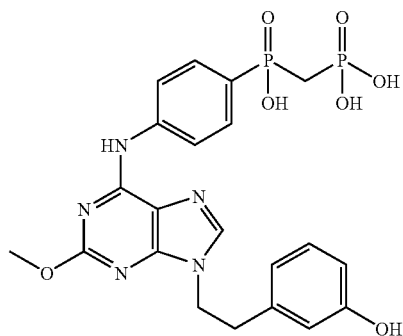

The title compound was synthesized in a manner similar to that described for Example 11. The product was obtained as a white solid: m/z 518 (M−H)

Example 13

[Hydroxy-(4-{9-[2-(3-hydroxy-phenyl)-ethyl]-2-isopropoxy-9H-purin-6-ylamino}-phenyl)-phosphinoylmethyl]-phosphonic Acid

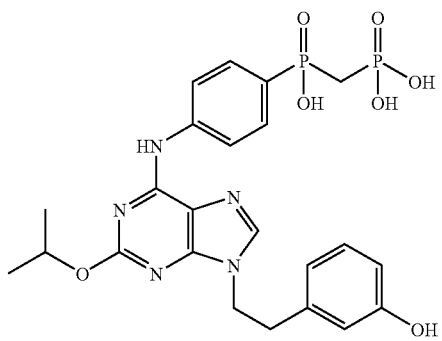

The title compound was synthesized in a manner similar to that described for Example 11. The product was obtained as a white solid: m/z 546 (M–H)

Example 14

(Hydroxy-{4-[9-methyl-2-(piperidin-4-ylmethoxy)-9H-purin-6-ylamino]-phenyl}-phosphinoylmethyl)-phosphonic Acid

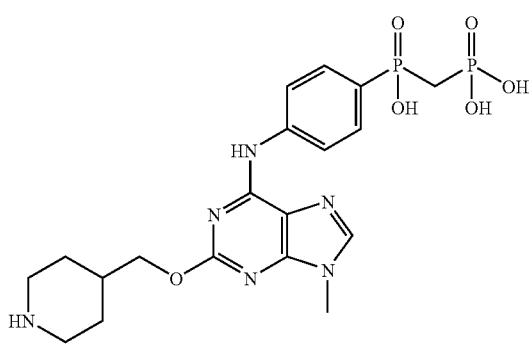

The title compound was synthesized in a manner similar to that described for Example 11. The product was obtained as a white solid: 495 m/z (M–H)

Example 15

{[4-(9-Ethyl-2-isopropoxy-9H-purin-6-ylamino)-phenyl]-hydroxy-phosphinoylmethyl}-phosphonic Acid

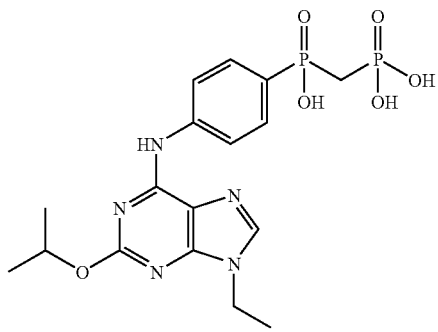

The title compound was synthesized in a manner similar to that described for Example 11. The product was obtained as a white solid: 454 m/z (M–H)

Example 16

({4-[9-Ethyl-2-(piperidin-4-ylmethoxy)-9H-purin-6-ylamino]-phenyl}-hydroxy-phosphinoylmethyl)-phosphonic Acid

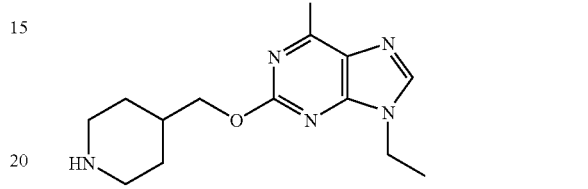

The title compound was synthesized in a manner similar to that described for Example 11. The product was obtained as a white solid: 509 m/z (M–H)

Example 17

[(4-{2-(2-Dimethylamino-propylamino)-9-[2-(3-hydroxy-phenyl)-ethyl]-9H-purin-6-ylamino}-phenyl)-hydroxy-phosphinoylmethyl]-phosphonic Acid

[(4-{2-(2-Dimethylamino-propylamino)-9-[2-(3-hydroxy-phenyl)-ethyl]-9H-purin-6-ylamino}-phenyl)-hydroxy-phosphinoylmethyl]-phosphonic Acid:

A reaction vessel, flushed with $N_2$, containing a biphasic solution of [(4-{2-Fluoro-9-[2-(3-hydroxy-phenyl)-ethyl]-9H-purin-6-ylamino}-phenyl)-hydroxy-phosphinoylmethyl]-phosphonic acid (0.2 g, 0.39 mmol), 3-(dimethylamino)propylamine (0.121 g, 1.18 mmol), and N,N-diisopropylethylamine (0.69 mL, 3.94 mmol) in 2.0 mL DMSO was heated at 120° C. for 13 h. Upon removing excess N,N-diisopropylethylamine, under reduced pressure, the slightly brown solution was added ~10 mL of $H_2O$ to produce a milky, off-white solution. Further precipitation occurred upon addition of TFA (final pH=1–2), at which time the mixture was stirred vigorously for ~20 min, filtered, then washed with acidified $H_2O$ (TFA, pH=1–2; 4×20 mL), EtOH (2×20 mL), and $Et_2O$ (4×20 mL). The resulting solid was dissolved in ~30 mL of $H_2O$ (adjusted to pH ~9 with 10% NaOH), filtered (0.2 μm, PTFE filter), and purified by RP-HPLC (CH₃CN/H₂O). Lyophilization provided an off-white solid, isolated as its TFA salt (0.082 g): m/z 588 (M–H).

Example 18

({4-[2-(trans-4-Amino-cyclohexylamino)-9-isopropyl-9H-purin-6-ylamino]-phenyl}-hydroxy-phosphinoylmethyl)-phosphonic Acid

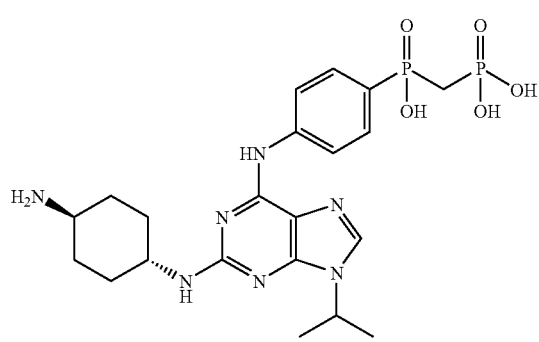

The title compound was synthesized in a manner similar to that described for Example 17. The product was obtained as a white solid: 522 m/z (M–H)

Example 19

[(4-{2-Ethylamino-9-[2-(3-hydroxy-phenyl)-ethyl]-9H-purin-6-ylamino}-phenyl)-hydroxy-phosphinoylmethyl]-phosphonic Acid

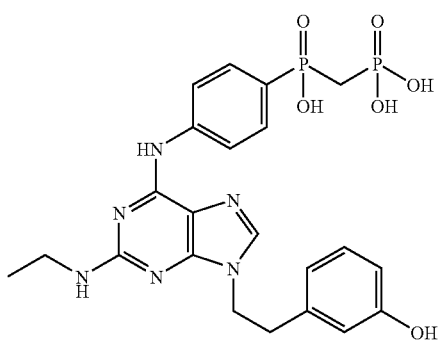

The title compound was synthesized in a manner similar to that described for Example 17. The product was obtained as a white solid: 531 m/z (M–H)

Example 20

[Hydroxy-(4-{9-[2-(3-hydroxy-phenyl)-ethyl]-2-[(tetrahydro-furan-S-2-ylmethyl)-amino]-9H-purin-6-ylamino}-phenyl)-phosphinoylmethyl]-phosphonic Acid

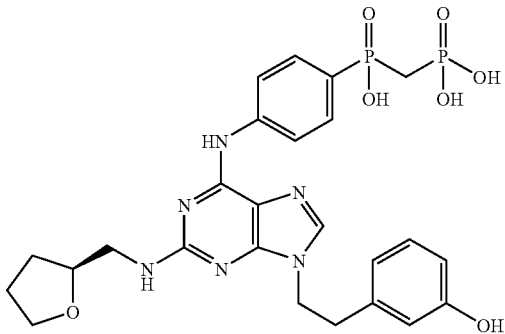

The title compound was synthesized in a manner similar to that described for Example 17. The product was obtained as a white solid: 587 m/z (M–H)

Example 21

[Hydroxy-(4-{9-[2-(3-hydroxy-phenyl)-ethyl]-2-[(tetrahydro-furan-R-2-ylmethyl)-amino]-9H-purin-6-ylamino}-phenyl)-phosphinoylmethyl]-phosphonic Acid

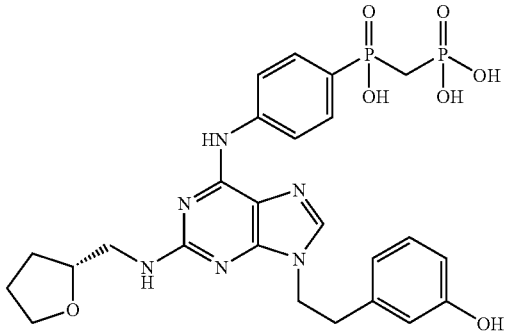

The title compound was synthesized in a manner similar to that described for Example 17. The product was obtained as a white solid: 587 m/z (M–H)

Example 22

({4-[2(4-Amino-cyclohexylamino)-9-ethyl-9H-purin-6-ylamino]-phenyl}-hydroxy-phosphinoylmethyl)-phosphonic Acid

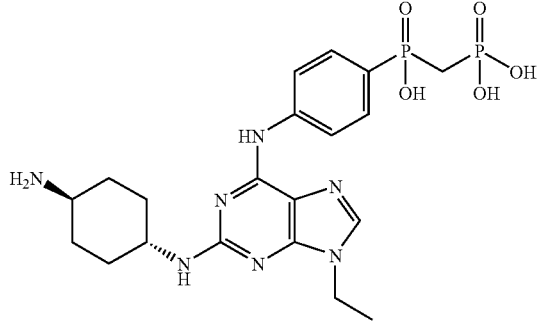

The title compound was synthesized in a manner similar to that described for Example 17. The product was obtained as a white solid: 508 m/z (M–H)

Example 23

[(4-{9-Ethyl-2-[2-(1H-imidazol-4-yl)-ethylamino]-9H-purin-6-ylamino}-phenyl)-hydroxy-phosphinoyl-methyl]-phosphonic Acid

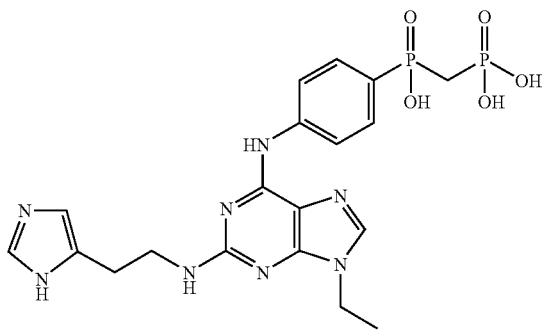

The title compound was synthesized in a manner similar to that described for Example 17. The product was obtained as a white solid: 505 m/z (M–H)

Example 24

[(4-{9-Ethyl-2-[(piperidin-4-ylmethyl)-amino]-9H-purin-6-ylamino}-phenyl)-hydroxy-phosphinoylmethyl]-phosphonic Acid

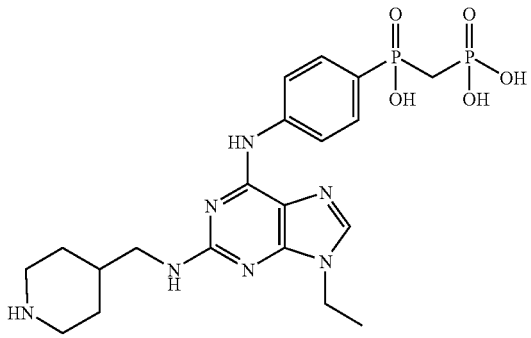

The title compound was synthesized in a manner similar to that described for Example 17. The product was obtained as a white solid: 508 m/z (M–H)

Example 25

In another embodiment, compounds as disclosed and described herein can be synthesized by solid-phase parallel synthesis, for example on a Quest 210 synthesizer (Argonaut Technologies); according to the Scheme outlined below:

Solid-Phase Purine Synthetic Scheme

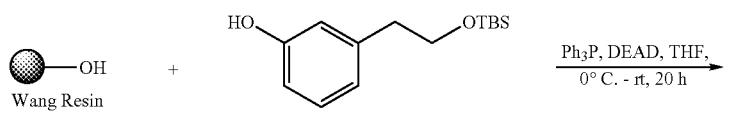

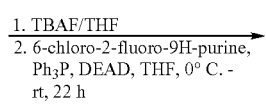

1a

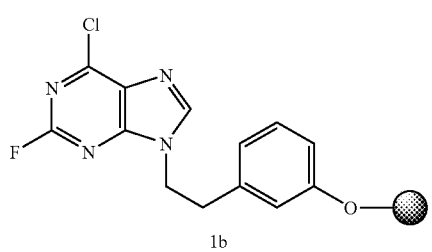

1b

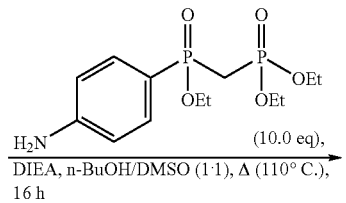

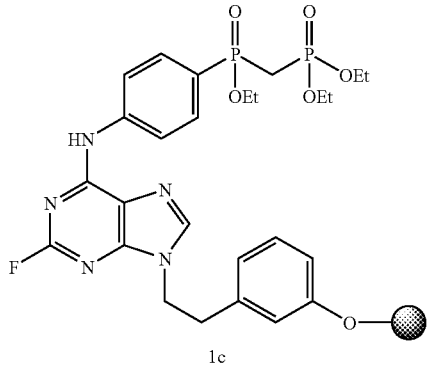

1c 1. (CH₃)₂NCH₂CH₂NH₂ (10 0 eq), DIEA, n-BuOH/DMSO (1 1), Δ (110° C.), 16 h
2. TFA/DCM (2% TIS)
3. TMSI, CH₃CN, -20 TO 0° C.
4. RP HPLC

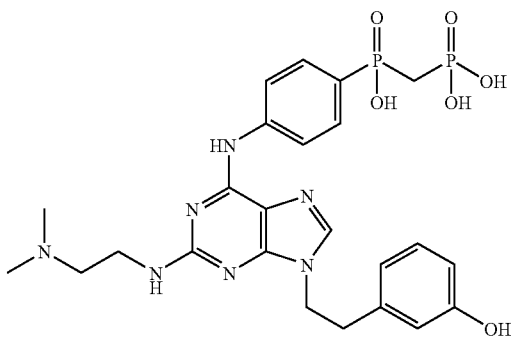

Example 26

[(4-{2-(2-Dimethylamino-ethylamino)-9-[2-(3-hydroxy-phenyl)-ethyl]-9H-purin-6-ylamino}-phenyl)-hydroxy-phosphinoylmethyl]-phosphonic Acid

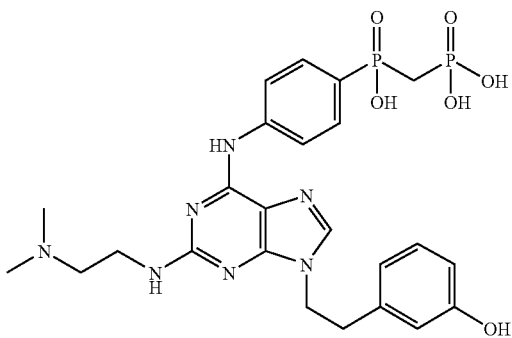

Preparation of Ether Resin (1a):

To a Teflon® RV (reaction vessel) containing 0.3 g (0.96 mmol/g, 0.29 mmol) of Wang resin was added a solution of 3-[2-(tert-Butyl-dimethyl-silanyloxy)-ethyl]-phenol (0.73 g, 2.9 mmol) and triphenylphosphine (0.38 g, 1.44 mmol) in 1.4 mL of THF. The RV was cooled to 0° C. (Julabo chiller) and then added, under an atmosphere of N₂, 2.0 mL (1.44 mmol) of a 0.72 M solution of DEAD (diethyl azodicarboxylate) in THF. The resin mixture was warmed, while agitating, to ambient temperature over 2 h and then agitated for an additional 20 h, upon which the RV was drained and the resin washed successively with THF (5×5.0 mL), DMA (5×5.0 mL), CH₂Cl₂ (5×5.0 mL), Et₂O (2×5.0 mL), CH₂Cl₂ (1×5.0 mL), Et₂O (1×5.0 mL), and CH₂Cl₂ (2×5.0 mL). Excess solvent was removed via N₂ flow overnight to provide the ether resin 1a. The following analytical data was obtained upon cleavage of 1a (3–5 mg) with 30% TFA/CH₂Cl₂ (~5 min): 83HPLC purity; HPLC RT (retention time, min) matches commercially available 3-hydroxyphenethyl alcohol (TBS group removed in TFA cleavage).

Preparation of Purine Resin (1b):

To the ether resin 1a (0.29 mmol) was added 6.6 mL (6.57 mmol) of a 1.0 M solution of TBAF (tetrabutylammonium fluoride) in THF. The resin mixture was agitated for 2 h, upon which the RV was drained and the resin washed successively with THF (5×5.0 mL), DMA (5×5.0 mL), CH₂Cl₂ (5×5.0 mL), Et₂O (2×5.0 mL), CH₂Cl₂ (1×5.0 mL), Et₂O (1×5.0 mL), and CH₂Cl₂ (2×5.0 mL). Excess solvent was removed via N₂ flow overnight to provide the deprotected resin. A resin aliquot (3–5 mg) was cleaved with 30% TFA/CH₂Cl₂ (~5 min) to verify resin bound compound integrity: 80% HPLC purity; HPLC RT (retention time, min) matches commercially available 3-hydroxyphenethyl alcohol.

To the dried resin (0.29 mmol) was added a homogeneous suspension of 6-chloro-2-fluoro-9H-purine (0.50 g, 2.9 mmol) and triphenylphosphine (0.38 g, 1.44 mmol) in 1.75 mL of THF. The RV was cooled to 0° C. (Julabo chiller) and then added, under an atmosphere of N₂, 2.0 mL (1.44 mmol) of a 0.72M solution of DEAD (diethyl azodicarboxylate) in THF. The resin mixture was warmed, while agitating, to ambient temperature over 1.5 h and then agitated for an additional 22 h, upon which the RV was drained and the resin washed successively with THF (5×5.0 mL), DMA (5×5.0 mL), CH₂Cl₂ (5×5.0 mL), Et₂O (2×5.0 mL), CH₂Cl₂ (1×5.0 mL), Et₂O (1×5.0 mL), and CH₂Cl₂ (2×5.0 mL). Excess solvent was removed via N₂ flow overnight to provide the purine resin 1b. The following analytical data was obtained upon cleavage of 1b (3–5 mg) with 30%

TFA/CH$_2$Cl$_2$ (~5 min): 65% HPLC purity, ~5:1 major/minor peaks (no apparent 3-hydroxyphenethyl alcohol HPLC peak).

Preparation of Purine Resin (1c):

To the purine resin 1b (0.29 mmol) was added a solution of [(4-Amino-phenyl)-ethoxy-phosphinoylmethyl]-phosphonic acid diethyl ester (0.97 g, 2.88 mmol) and N,N-diisopropylethylamine (0.25 mL, 1.44 mmol) in 3.0 mL of 1:1 n-butanol/DMSO. The sealed RV was heated at 110° C. for 16 h, upon which the RV was cooled to ambient temperature, drained, and the resin washed successively with DMA (5×5.0 mL), CH$_2$Cl$_2$ (5×5.0 mL), Et$_2$O (2×5.0 mL), CH$_2$Cl$_2$ (1×5.0 mL), Et$_2$O (1×5.0 mL), and CH$_2$Cl$_2$ (2×5.0 mL). Excess solvent was removed via N$_2$ flow overnight to provide the aminated purine resin 1c. The following analytical data was obtained upon cleavage of 1c (3–5 mg) with 30% TFA/CH$_2$Cl$_2$ (~5 min): m/z 592 (M+H).

[(4-{2-(2-Dimethylamino-ethylamino)-9-[2-(3-hydroxy-phenyl)-ethyl]-9H-purin-6-ylamino}-phenyl)-hydroxy-phosphinoylmethyl]-phosphonic Acid:

To the aminated purine resin 1c (0.29 mmol) was added a solution of N,N-dimethylethylenediamine (0.25 g, 2.88 mmol) and N,N-diisopropylethylamine (0.25 mL, 1.44 mmol) in 3.0 mL of 1:1 n-butanol/DMSO. The sealed RV was heated at 110° C. for 16 h, upon which the heat was turned off, the RV drained immediately, and the resin washed (while still hot) successively with DMA (5×5.0 mL), CH$_2$Cl$_2$ (5×5.0 mL, at ambient temperature), Et$_2$O (2×5.0 mL), CH$_2$Cl$_2$ (1×5.0 mL), Et$_2$O (1×5.0 mL), and CH$_2$Cl$_2$ (2×5.0 mL). Excess solvent was removed via N$_2$ flow overnight to provide the bis-aminated purine resin.

To the bis-aminated purine resin (0.29 mmol) was added 5.6 mL of 30% TFA/CH$_2$Cl$_2$ (2% triisopropyl silane). The resin mixture was agitated for 1 h, upon which the filtrate was collected and the resin washed with CH$_2$Cl$_2$ (3×5.0 mL). The combined filtrates were concentrated (Savant speed-vac), added 3–4 mL CH$_2$Cl$_2$, then reconcentrated to provide a dark yellow oil.

The oil was dissolved in 6.6 mL of CH$_3$CN, cooled to 0° C., then added 1.0 mL (7.2 mmol) of TMSI (iodotrimethylsilane). The resulting yellow solution (some precipitate) was stored at −20° C. for 2 h (periodic swirling), then 0° C. for 1 h, upon which 0.4 mL (2.81 mmol) of TMSI was added and reaction continued at 0° C. for 3 h. The excess TMSI was quenched at 0° C. with ~4 mL of 20% aqueous NaHSO$_3$, the pH adjusted to 11–12 with 10% NaOH, and the CH$_3$CN removed by rotary evaporation. The pH was re-adjusted to 10–11 with TFA, upon which the solution was filtered (0.2 μm, PTFE filter) and purified by RP-HPLC (CH$_3$CN/H$_2$O). Lyophilization provided a white solid, isolated as its TFA salt (0.035 g): $^1$H NMR (300 MHz, DMSO-d$_6$) δ 9.76 (s, 1H), 9.33 (br s, 1H), 8.07–7.65 (m, 5H), 7.08–6.59 (m, 5H), 4.27 (m, 2H), 3.66 (m, 2H), 3.04 (m, 2H), 2.85 (s, 6H), 2.37 (m, 2H); m/z 576 (M+H).

Example 27

[(4-{2-(trans-4-Amino-cyclohexylamino)-9-[2-(3-hydroxy-phenyl)-ethyl]-9H-purin-6-ylamino}-phenyl)-hydroxy-phosphinoylmethyl]-phosphonic Acid

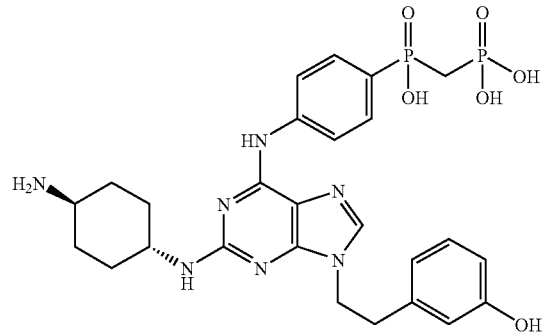

The title compound was synthesized in a manner similar to that described for Example 26. The white solid was isolated as its TFA salt: m/z 602 (M+H)

Example 28

[Hydroxy-(4-{9-[2-(3-hydroxy-phenyl)-ethyl]-2-[2-(3H-imidazol-4-yl)-ethylamino]-9H-purin-6-ylamino}-phenyl)-phosphinoylmethyl]-phosphonic Acid

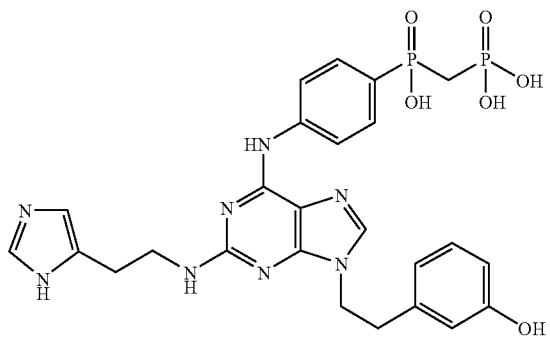

The title compound was synthesized in a manner similar to that described for Example 26. The white solid was isolated as its TFA salt: m/z 599 (M+H)

Example 29

[Hydroxy-(4-{2-(2-hydroxy-ethylamino)-9-[2-(3-hydroxy-phenyl)-ethyl]-9H-purin-6-ylamino}-phenyl)-phosphinoylmethyl]-phosphonic Acid

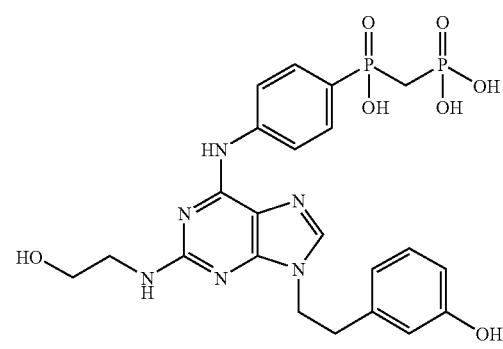

The title compound was synthesized in a manner similar to that described for Example 26. The product was obtained as a white solid: m/z 549 (M+H)

Example 30

(5-{2-(trans-4-Amino-cyclohexylamino)-9-[2-(3-hydroxy-phenyl)-ethyl]-9H-purin-6-ylamino}-2-phosphono-phenyl)-phosphonic Acid

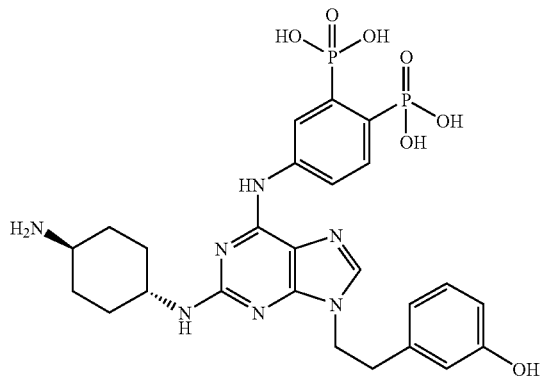

The title compound was synthesized in a manner similar to that described for Example 26. The white solid was isolated as its TFA salt: m/z 604 (M+H)

Example 31

(5-{9-[2-(3-Hydroxy-phenyl)-ethyl]-2-[2-(3H-imidazol-4-yl)-ethylamino]-9H-purin-6-ylamino}-2-phosphono-phenyl)-phosphonic Acid

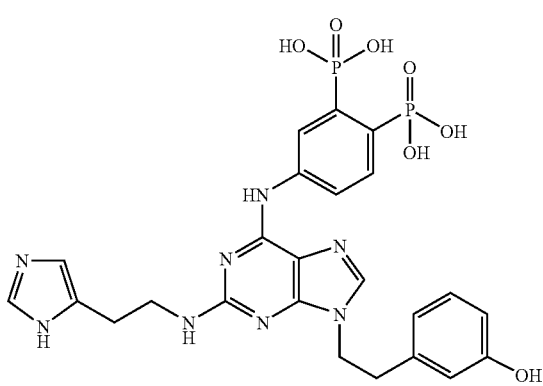

The title compound was synthesized in a manner similar to that described for Example 26. The white solid was isolated as its TFA salt: m/z 601 (M+H)

Example 32

(5-{2-(2-Dimethylamino-ethylamino)-9-[2-(3-hydroxy-phenyl)-ethyl]-9H-purin-6-ylamino}-2-phosphono-phenyl)-phosphonic Acid

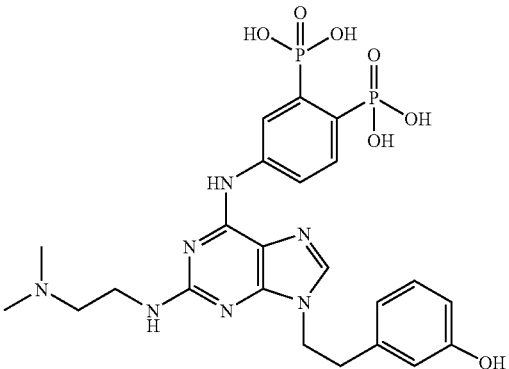

The title compound was synthesized in a manner similar to that described for Example 26. The white solid was isolated as its TFA salt: m/z 578 (M+H)

Example 33

[Hydroxy-(3-{9-[2-(4-hydroxy-phenyl)-ethyl]-6-phenylamino-9H-purin-2-ylamino}-propyl)-phosphinoylmethyl]-phosphonic Acid

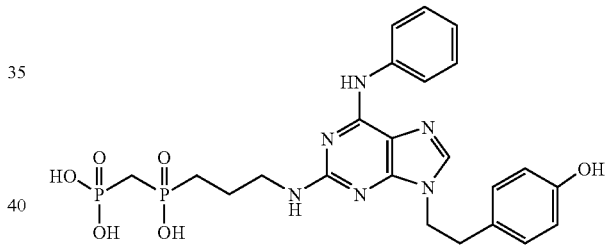

The title compound was synthesized in a manner similar to that described for Example 26. The product was obtained as a white solid: m/z 547 (M+H)

Example 34

[Hydroxy-(3-{9-[2-(3-hydroxy-phenyl)-ethyl]-6-phenylamino-9H-purin-2-ylamino}-propyl)-phosphinoylmethyl]-phosphonic Acid

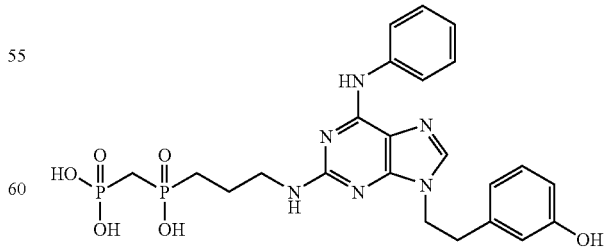

The title compound was synthesized in a manner similar to that described for Example 26. The product was obtained as a white solid: m/z 547 (M+H)

Example 35

(Hydroxy-{3-[9-(3-hydroxy-benzyl)-6-phenylamino-9H-purin-2-ylamino]-propyl}-phosphinoylmethyl)-phosphonic Acid

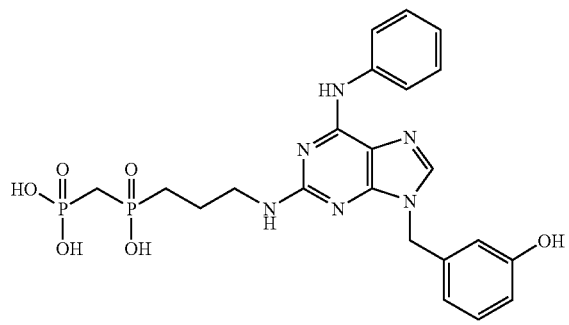

The title compound was synthesized in a manner similar to that described for Example 26. The product was obtained as a white solid: m/z 533 (M+H)

Example 36

({3-[6-(3-Chloro-phenylamino)-9-(3-hydroxy-benzyl)-9H-purin-2-ylamino]-propyl}-hydroxy-phosphinoylmethyl)-phosphonic Acid

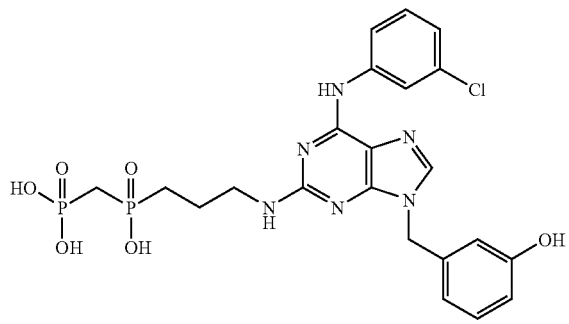

The title compound was synthesized in a manner similar to that described for Example 26. The product was obtained as a white solid: m/z 567 (M+H)

Example 37

[(3-{6-(3-Chloro-phenylamino)-9-[2-(4-hydroxy-phenyl)-ethyl]-9H-purin-2-ylamino}-propyl)-hydroxy-phosphinoylmethyl]-phosphonic Acid

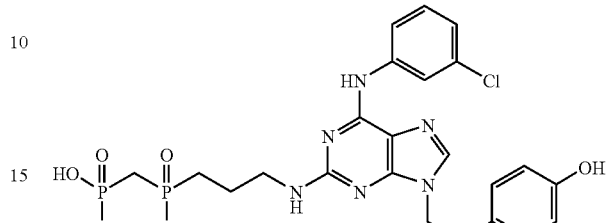

The title compound was synthesized in a manner similar to that described for Example 26. The product was obtained as a white solid: m/z 581 (M+H)

Example 38

[(3-{6-(3-Chloro-phenylamino)-9-[2-(3-hydroxy-phenyl)-ethyl]-9H-purin-2-ylamino}-propyl)-hydroxy-phosphinoylmethyl]-phosphonic Acid

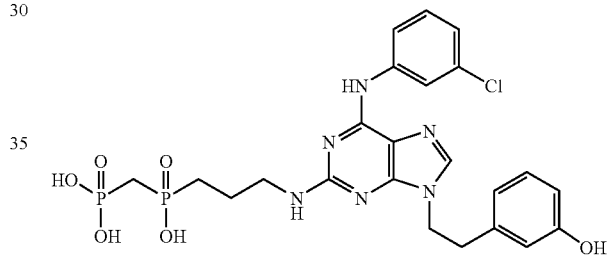

The title compound was synthesized in a manner similar to that described for Example 26. The product was obtained as a white solid: m/z 581 (M+H)

Example 39

In another embodiment, compounds as disclosed and herein described can be synthesized according to the Scheme outlined below:

Purine Synthetic Scheme

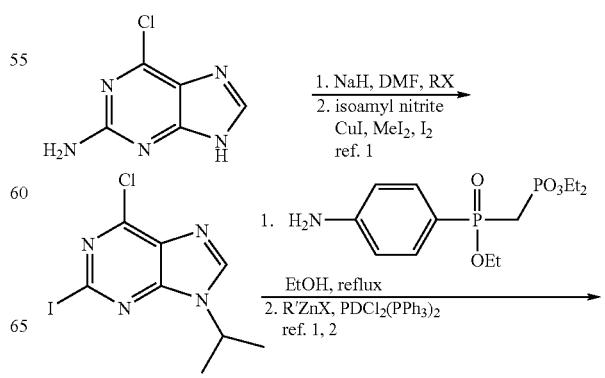

-continued

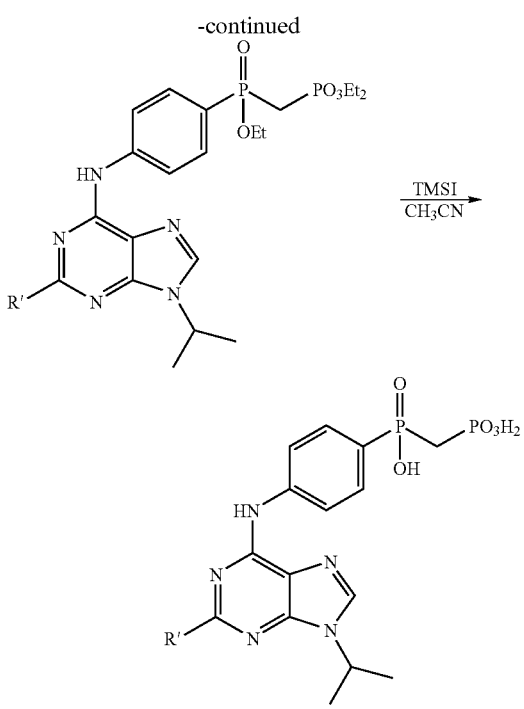

[1] Langli, G. et al. *Tetrahedron* 1996, 15, 5625.
[2] Rieke, R.D. et al. *J. Org. Chem.* 1991, 56, 1445.

Example 40

{[4-(2-Cyclopentyl-9-isopropyl-9H-purin-6-ylamino)-phenyl]-hydroxy-phosphinoylmethyl}-phosphonic Acid

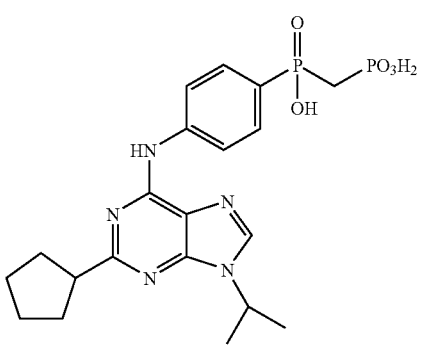

6-Chloro-9-isopropyl-9H-purin-2-ylamine:

To 6-chloro-9H-purin-2-ylamine (20 g, 0.12 moles) in DMF (200 mL) at −11° C. was added NaH (5.7 g, 0.14 moles, 60%) portionwise over 1 h. The mixture as stirred for 1 h, then 2-iodopropane (14.2 mL, 0.14 moles) was added dropwise. The solution was warmed to rt, stirred for 18 h, quenched with sat'd NH$_4$Cl, and extracted with EtOAc. The combined extracts, were washed with water, sat'd NaCl, then dried over MgSO$_4$ and filtered. Concentration yielded an oil which was purified by silica gel chromatography (60% EtOAc/Hexane) to a white solid (13.4 g, 54%): MS [M+H]$^+$ 212; m.p. 135–136° C.

6-Chloro-2-iodo-9-isopropyl-9H-purine:

6-Chloro-9-isopropyl-9H-purin-2-ylamine (2.7 g, 12.8 mmol), CuI (1.2 g, 13.4 mmol), I$_2$ (3.3 g, 12.8 mmol), isoamyl nitrite (10.6 mL), and CH$_2$I$_2$ (5.3 g, 39.3 mmol) in THF (60 mL) were heated at reflux for 75 min. The mixture was cooled to rt, filtered through Celite, and adsorbed onto silica gel. Purification by chromatography (60% EtOAc/hexane) yielded an off-white solid (13.4 g, 54%): MS [M+H]$^+$ 323; m.p.104° C.

{Ethoxy-[4-(2-iodo-9-isopropyl-9H-purin-6-ylamino)-phenyl]-phosphinoylmethyl}-phosphonic Acid Diethyl Ester:

6-Chloro-2-iodo-9-isopropyl-9H-purine (1.7 g, 5.2 mmol), [(4-amino-phenyl)-ethoxy-phosphinoylmethyl]-phosphonic acid diethyl ester (2.6 g, 7.7 mmol), and DIPEA (2.7 mL, 15.5 mmol) were dissolved in EtOH (27 mL) and heated in a sealed tube at 105° C. for 48 h. After cooling, the EtOH was evaporated. The residue was poured into water and extracted with EtOAc. The combined extracts, were washed with water, sat'd NaCl, then dried over MgSO$_4$ and filtered. Concentration yielded an oil which was purified by silica gel chromatography (11% MeOH/EtOAc) to a glassy solid (1.8 g, 53%): MS [M+H]$^+$ 621.

{[4-(2-Cyclopentyl-9-isopropyl-9H-purin-6-ylamino)-phenyl]-ethoxy-phosphinoylmethyl}-phosphonic Acid Diethyl Ester:

To {ethoxy-[4-(2-iodo-9-isopropyl-9H-purin-6-ylamino)-phenyl]-phosphinoylmethyl}-phosphonic acid diethyl ester (0.30 g, 0.48 mmol) in DMF (3.9 mL) was added PdCl$_2$(PPh$_3$)$_4$ (17 mg, 0.024 mmol) followed by cyclopentylzinc bromide (0.5M THF, 3.9 mL, 1.9 mmol). The mixture was stirred at rt for 1 h, poured into water and extracted with EtOAc. The combined extracts, were washed with water, sat'd NaCl, then dried over MgSO$_4$ and filtered. The material was used without purification in the next reaction.

{[4-(2-Cyclopentyl-9-isopropyl-9H-purin-6-ylamino)-phenyl]-hydroxy-phosphinoylmethyl}-phosphonic Acid:

To {[4-(2-cyclopentyl-9-isopropyl-9-purin-6-ylamino)-phenyl]-ethoxy-phosphinoylmethyl}-phosphonic acid diethyl ester (0.34 g, 0.6 mmol) in CH$_3$CN (3 mL) at 0° C. was added TMSI (0.98 mL, 7.2 mmol). The mixture was stirred for 1 h, quenched with water and Na$_2$S$_2$O$_5$. The pH of the solution was adjusted to 7.5 with the dropwise addition of 2N NaOH and purified by RP HPLC (CH$_3$CN/H$_2$O). Lyophylization yielded a white solid: (0.14 g, 59%, two steps): MS [M+H]$^+$ 480.

Example 41

In yet another embodiment, compounds as disclosed and described herein can be synthesized according to the scheme outlined below:

Purine Synthetic Scheme

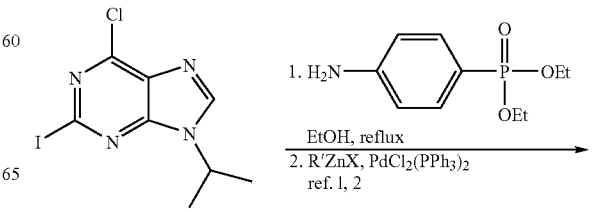

67

-continued

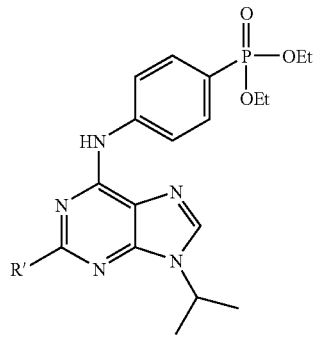

[1]Langli, G. et al. *Tetrahedron* 1996, 15, 5625.
[2]Rieke, R. D. et al. *J. Org. Chem.* 1991, 56, 1445.

Example 42

[4-(2-Cyclopentyl-9-isopropyl-9H-purin-6-ylamino)-phenyl]-phosphonic Acid Diethyl Ester

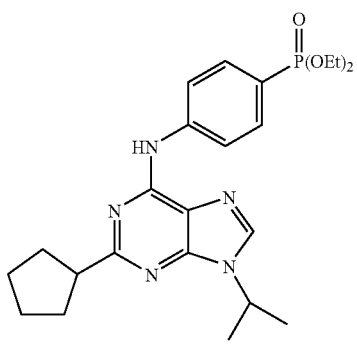

(4-Amino-phenyl)-phosphonic Acid Diethyl Ester:

(4-Nitro-phenyl)-phosphonic acid diethyl ester (7.6 g, 29.1 mmol) and SnCl₂ (29.6 g, 0.13 mmol) were heated at reflux for 1 h. The mixture was poured in CH₂Cl₂ (500 mL) and adjusted to pH 8 with sat'd Na₂CO₃. The resulting mixture was filtered through Celite (CH₂Cl₂ wash) and the layers separated. The aqueous layer was extracted with CH₂Cl₂ and the combined extracts, were washed with water, sat'd NaCl, then dried over MgSO₄ and filtered. Concentration yielded a light yellow solid (5.9 g, 88%): MS [M+H]⁺ 230; m.p. 117–118° C.

[4-(2-Iodo-9-isopropyl-9H-purin-6-ylamino)-phenyl]-phosphonic Acid Diethyl Ester:
Identical to that from Example 40 except for the substrate. Glassy solid: (0.95 g, 60%): MS [M+H]⁺ 516.

[4-(2-Cyclopentyl-9-isopropyl-9H-purin-6-ylamino)-phenyl]-phosphonic Acid Diethyl Ester:
Identical to that from Example 40 except for the substrate. Purified by RP HPLC (CH₃CN/H₂O). Lyophylization yielded a white solid: (45 mg, 63%): MS [M+H]⁺ 458.

The additional described phosphorus-containing moieties can be synthesized according to the schemes outlined below:

68

Example 43

[4-Aminomethyl-2-(diethoxy-phosphoryl)-phenyl]-phosphonic Acid Diethyl Ester

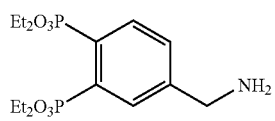

(3,4-Dihydroxy-benzyl)-carbamic Acid Tert-butyl Ester:
4-Aminomethyl-benzene-1,2-diol hydrobromide (5.6 g, 25.2 mmol) was dissolved in CH₃CN/H₂O 1:1 (100 mL). NaHCO₃ (4.3 g, 50.4 mmol) was added followed by Boc₂O (5.5 g, 25.2 mmol). The mixture was stirred for 18 h, concentrated, and extracted with EtOAc. The combined extracts were washed with water, dried over magnesium sulfate, and concentrated to a tan solid which was used without purification in the next reaction.

Trifluoro-methanesulfonic Acid 5-(tert-butoxycarbonylamino-methyl)-2-trifluoromethanesulfonyloxy-phenyl Ester:
(3,4-Dihydroxy-benzyl)-carbamic acid tert-butyl ester (5.5 g, 23.0 mmol), N-phenyltrifluoromethanesulfonimide (26.9 g, 75 mmol), and Et₃N (14.9 mL, 107 mmol) were dissolved in CH₂Cl₂ (80 mL) and stirred for 24 h. The mixture was dumped into water and the layers seperated. The aqueous layer was extracted with methylene chloride. The combined extracts were washed with water, dried over magnesium sulfate, concentrated, and purified by silica gel chromatography (hexane/EtOAc 3:1) to yield the product as a brown oil (9.0 g, 78%).

[4-(tert-Butoxycarbonylamino-methyl)-2-(diethoxy-phosphoryl)-phenyl]-phosphonic Acid Diethyl Ester:
Trifluoro-methanesulfonic acid 5-(tert-butoxycarbonylamino-methyl)-2-trifluoromethanesulfonyloxy-phenyl ester (5 g, 10.0 mmol), diethyl phosphite (2.8 mL, 20.3 mmol), N-methylmorpholine (2.7 mL, 25.1 mmol) and tetrakis (triphenylphosphine)-palladium(0) (1.2 g) were dissolved in anhydrous acetonitrile (100 mL) and heated in a sealed tube at 90° C. for 48 h. After cooling, the mixture was diluted with EtOAc (200 mL) and washed with water, 1 N HCl and brine. The organic layer was dried over magnesium sulfate, concentrated, and purified by silica gel chromatography (5% MeOH/CHCl₃) to yield the product as a colorless oil (2.0 g, 42%). ¹H NMR (300 Mhz, CDCl₃) δ 1.35 (m, 12 H), 3.79 (bs, 2 H), 3.96 (m, 8H), 7.45 (m, 1H), 7.91 (m, 2H).

[4-Aminomethyl-2-(diethoxy-phosphoryl)-phenyl]-phosphonic Acid Diethyl Ester:
[4-(tert-Butoxycarbonylamino-methyl)-2-(diethoxy-phosphoryl)-phenyl]-phosphonic acid diethyl ester (2.0 g, 4.2 mmol) was dissolved in TFA/CH₂Cl₂ (25%, 20 mL) and stirred for 3 h. The mixture was evaporated under a stream of N₂, dissolved in EtOAc and washed with sat'd NaHCO₃. The organic layer was dried over magnesium sulfate, and concentrated to a brown oil (0.9 g, 2.3 mmol) which was used without purification in the next reaction.

Example 44

1-(Bis-diethylphosphonomethylene)-4-aminobenzene

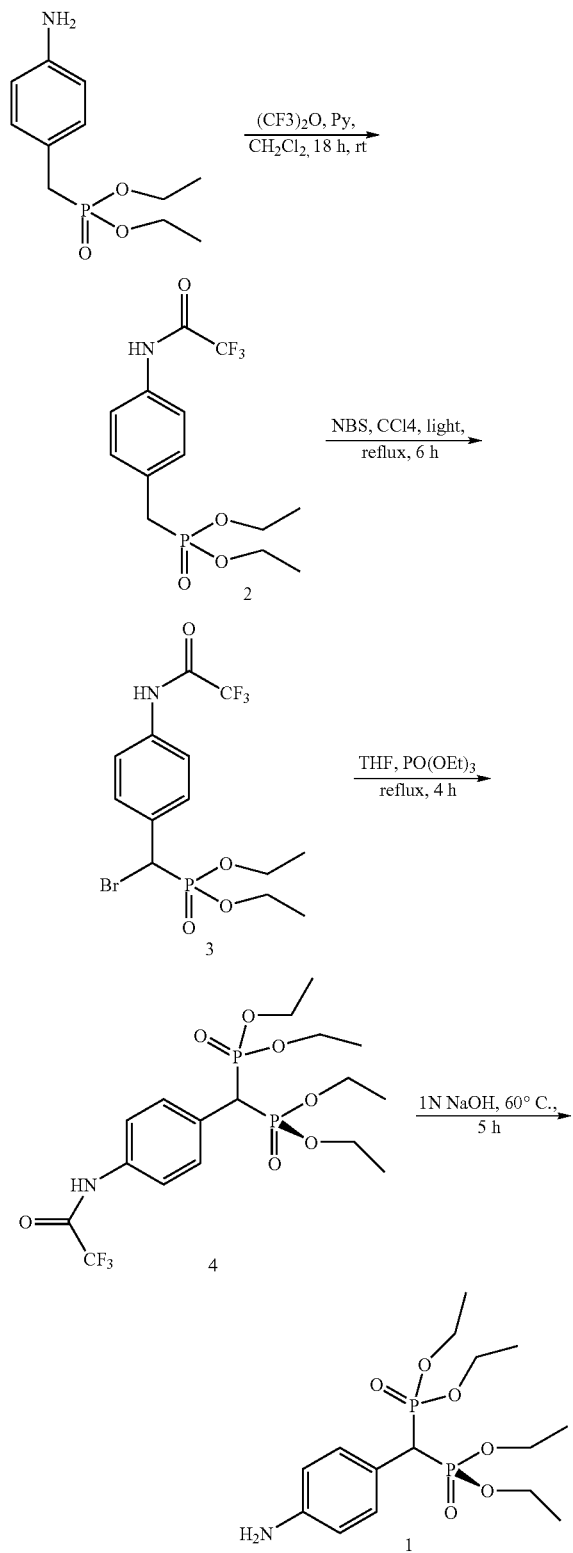

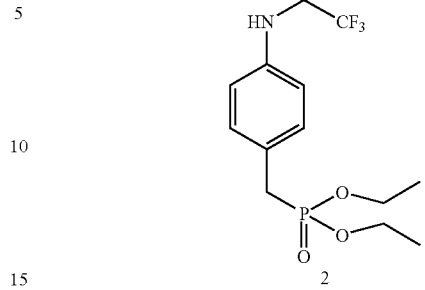

Diethyl (4-(N-trifluoroacetyl amino benzyl) Phosphonate

To diethyl (4-aminobenzyl)phosphonate (10 g) in anhydrous dichloromethane (100 mL) was added pyridine (4.0 mL) followed by trifluoroacetic anhydride (7.0 mL) and stirred at rt overnight (~18 hrs). Reaction mixture was washed carefully with a saturated solution of aqueous sodium bicarbonate (10 mL), brine (10 mL) and the dichloromethane was dried $Na_2SO_4$) to afford product (93%). MS: 338 (M−1).

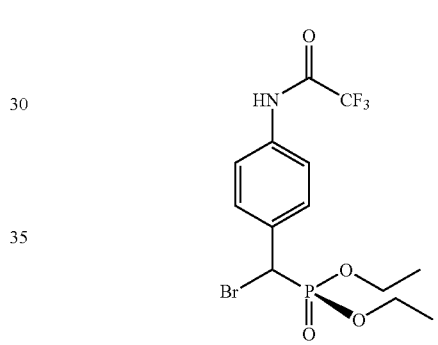

Diethyl (4-(N-trifuoroacetylamino)-α-bromobenzyl) Phosphonate

To the Diethyl (4-(N-trifluoroacetyl amino benzyl) phosphonate (9.75 g, 41.13 mmols) in anhydrous carbon tetrachloride (100 mL) was added NBS (1.6 g, 41.13 mmols) and heated to reflux under intense visible light with stirring under which time a white precipitate formed. The reaction was cooled to rt and then filtered. The filtrate was half concentrated then left in the freezer overnight to crystallize. The crystalline product was seperated by filtration (7.2 g, 60%). MS: 416, 418 (M−1 $Br^{79}Br^{80}$).

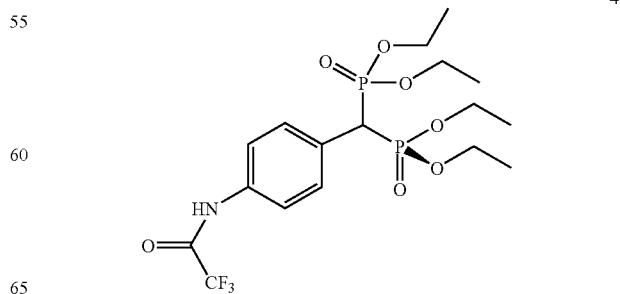

1-(Bis-diethylphosphonomethylene-4-(N-trifluoroacety-lamino)benzene

To Diethyl (4-(N-trifuoroacetylamino)-α-bromobenzyl) phosphonate (7.2 g, 17.22 mmols) in anhydrous THF (50 mL) was added triethylphosphite (0.82 mL, 17 mmol) and stirred under reflux for 4 h. Reaction mixture was cooled to rt and concentrated. Residue was taken up in boiling ethyl ether and cooled to rt. Solid was filtered off to afford 6.0 g product (73%). Pale pink solid. MS: 476 (M+H), 475 (M−H).

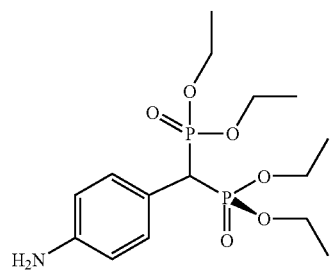

1-(Bis-diethylphosphonomethylene)-4-aminobenzene

The above 1-(Bis-diethylphosphonomethylene-4-(N-trifluoroacetylamino)benzene (1.2 g, 2.52 mmols) in NaOH solution (0.1 N, 10 mL) was heated to 60_C for 5 h. The reaction mixture was cooled to rt, and extracted with methylene chloride. Combined organic layers were dried over sodium sulfate and concentrated to afford the product (0.85 g, 97%). MS: 412 (M+23).

Example 45

G. Bis-3,4-(diethylphophonyl)-β-phenylethyl Amine 5

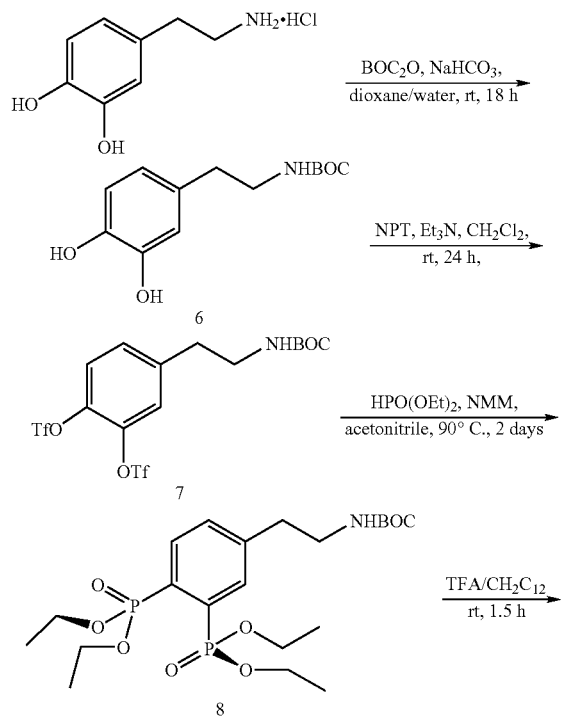

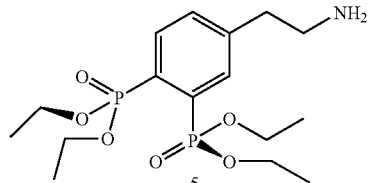

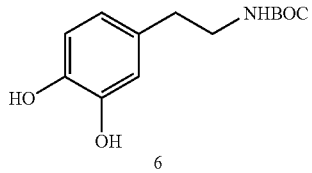

N-t-butoxycarbonyl-3-hydroxytyramine

To a solution of 3-hydroxytyramine hydrochloride (5.0 g, 26.36 mmol) in dixane/water (50/30 mL) at 0_C was added sodium bicarbonate (6.64 g, 79.08 mmol) and stirred for 10 min. To this was added Boc anhydride (7.48 g, 34.275 mmol) and stirred at rt for 18 h. After removing dioxane in vacuo, the slurry was taken up in water (~60 mL) and extracted in ethyl acetate (25 mL×3). The organics were washed with 1N HCl (10 mL×2) followed by brine (10 mL); dried (sodium sulfate) and concentrated which when cooled in the refregerator crystallized the next day (3.87 g, 57%). MS: 252 (M−H).

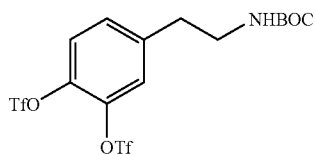

N-t-butoxycarbonyl-bis-3,4-O-triflyl-β-phenylethyl Amine

To a solution of N-Boc-3-hydroxytyramine (3.87 g, 15.28 mmol) in anhydrous dichloromethane (70 mL) was added triethyl amine (61.12 mmol) followed by N-phenyl triflamide (16.37 g, 45.84 mmol) and stirred at rt for 24 h. Reaction mixture was diluted with dichloromethane (100 mL) and washed successively with 1N HCl (3×10 mL) and brine (10 mL) and dried (sodium sulfate). After concentration of dichloromethane extract the brown oil was chromatographed on silicagel using hexane/ethyl acetate (10–100%) to give product as a viscous oil (6.32 g, 80%). MS: 516 (M−H).

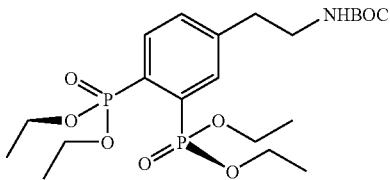

N-t-butoxycarbonyl-bis-3,4-(diethylphophonyl)-β-phenyl-ethyl Amine

To the N-t-butoxycarbonyl-bis-3,4-O-triflyl-β-phenyl-ethyl amine (6.32 g, 12.21 mmol) in acetonitrile in an atmosphere of argon was carefully added diethyl phosphite (3.46 mL, 26.87 mmol), N-methylmorpholine (3.09 mL, 30.54 mmol), tetrakistriphenylphosphine palladium(0) (1.41 g, 1.221 mmol) and after flushing the solution with argon for 10 min. it was stoppered and heated to 90_C for 2 days. Acetonitrile was concentrated, and the residue was diluted with ethyl acetate. The organic layer was washed with citric acid (10%, 10 mL×2), brine (10 mL) and dried (sodium sulfate). The yellow gum after concentration of ethyl acetate was purified by flash column chromatography on silica gel using ethyl acetate in hexane (33%–100%) followed by ethyl acetate/methanol (9/1) to give a pale yellow gum (992 mg, 16.5%). MS: 492(M–H).

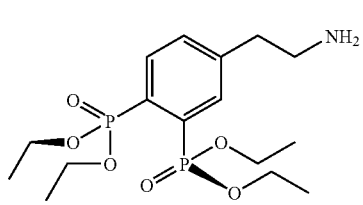

Bis-3,4-(diethylphophonyl)-β-phenylethyl Amine

To the N-t-butoxycarbonyl-bis-3,4-(diethylphophonyl)-β-phenylethyl amine (0.992 g, 2.01 mmol) in dichloromethane (10 mL) was added TFA (25% in dichloromethane, 2.5 mL). After 1.5 h the solvents were removed in vacuo and the residue was diluted with saturated sodium bicarbonate and dichloromethane (5 mL and 50 mL). The aqueous layer was re extracted with dichloromethane (25 mL×2). Combined organics were concentrated to give a pale brown gum (0.758 g, 96%) which was pure enough for the next step. MS:392 (M–H), 416 (M+23).

Example 46

Synthesis of Exemplary Alkylpurine Compounds

It will be appreciated that in certain exemplary embodiments, purine derivatives in which $R_C$ represents an alkyl moiety can be prepared according to the general methodology described in the Scheme depicted below.

Synthesis of $R_3$ Alkylpurines

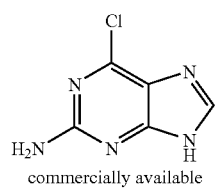

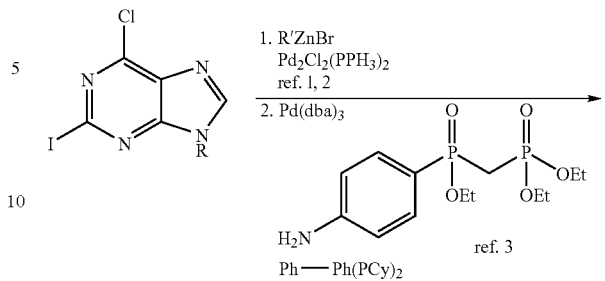

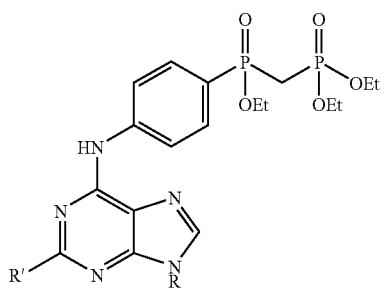

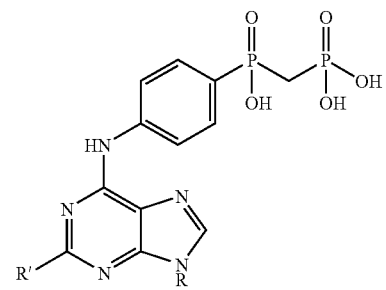

[1]Langli, G et al. *Tetrahedron* 1996, 15, 5625–5638.
[2]Rieke, R. D. et al *J. Org. Chem.* 1991, 56, 1445–1453.
[3]Buchwald, S. L. *J. Org. Chem.* 2000, 65, 1158–1174.

Example 47

Compounds

Certain inventive compounds as detailed herein as shown as follows, however, it will be appreciated that the present invention is not intended to be limited by those compounds depicted below. It will be appreciated that a variety of compounds can be synthesized using the techniques as described herein. Certain of those compounds are depicted below, however the present invention is not intended to be limited by these compounds.

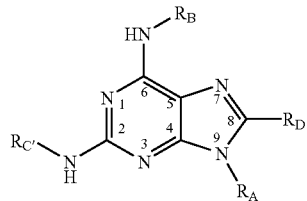

R_D is hydrogen

| RA | RB | RC' |
|---|---|---|
| iPr (isobutyl) | CH₂Ph | HOCH₂CH(iPr)- (2-methylpropyl with stereo) |
| iPr | 3-ClPh | HOCH₂CH(iPr)- |
| iPr | 3-ClPh | HOCH₂CH₂CH₂- |
| Me | CH₂Ph | HOCH₂CH₂CH₂- |
| Me | 3-ClPh | HOCH₂CH(iPr)- |
| iPr | 3-ClPh | RC'—NH=F |
| iPr | 3-ClPh (N-Me) | HOCH₂CH(iPr)- |
| iPr | 3-ClPh | (HO)₂P(O)CH₂P(O)(OH)OCH₂CH(iPr)- |
| iPr | 3-ClPh | (HO)₂P(O)CH₂P(O)(OH)OCH₂CH₂CH₂- |
| iPr | 3-ClPh (N-Me) | (HO)₂P(O)CH₂P(O)(OH)OCH₂CH(iPr)- |
| iPr | 3-ClPh | HOCH₂CH₂CH₂CH₂- |
| iPr | 3-ClPh | HOCH₂CH₂CH₂CH₂CH₂- |

-continued
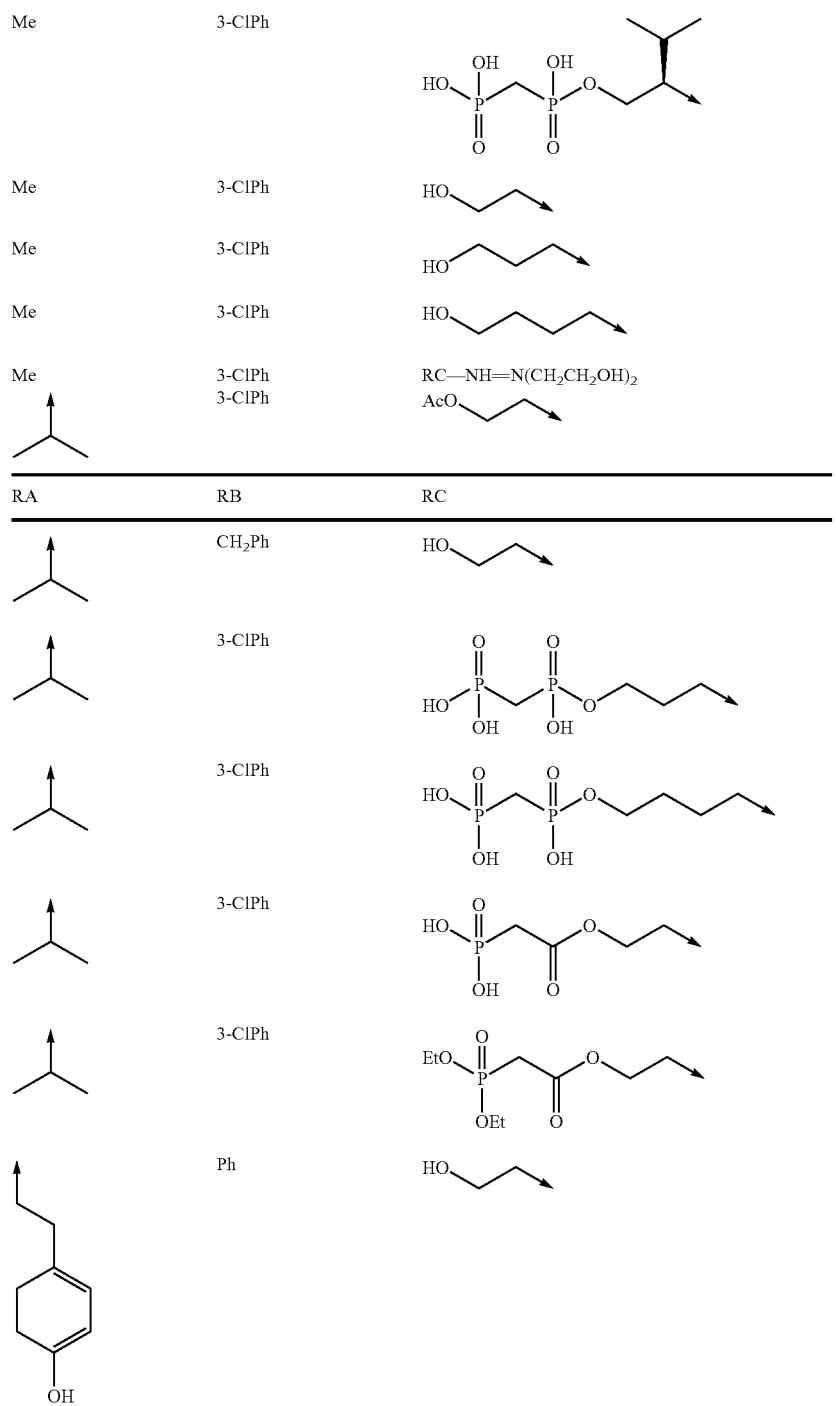

-continued
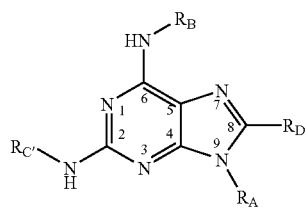
$R_D$ is hydrogen
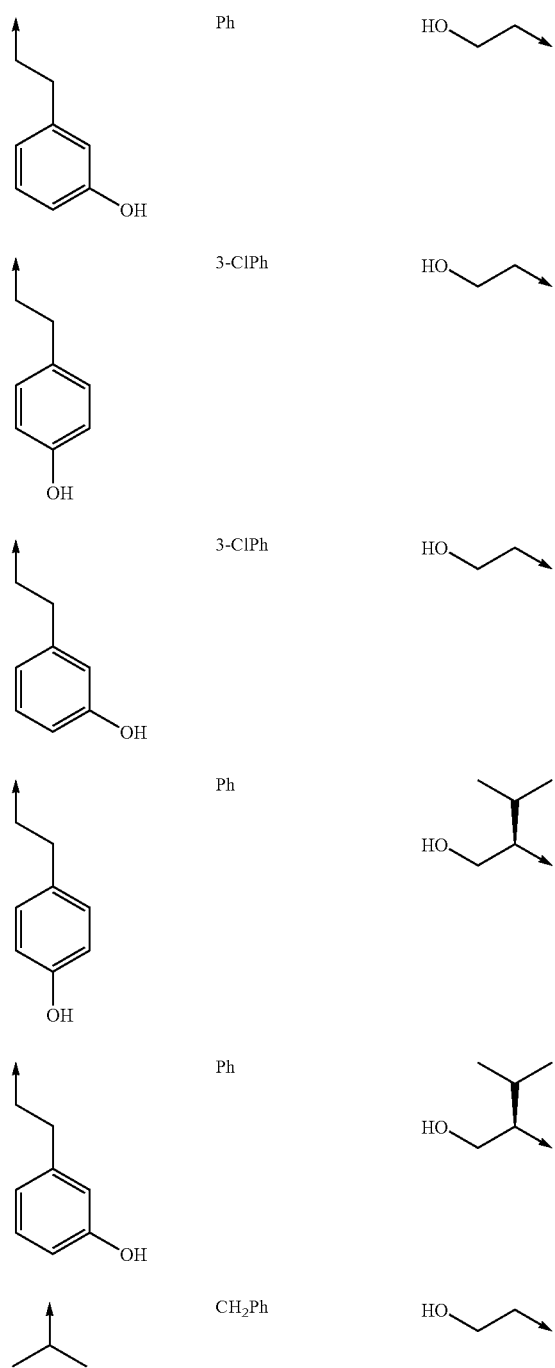

-continued
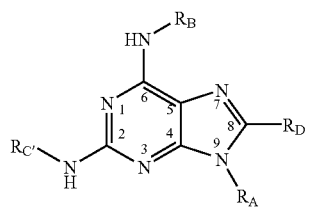
$R_D$ is hydrogen
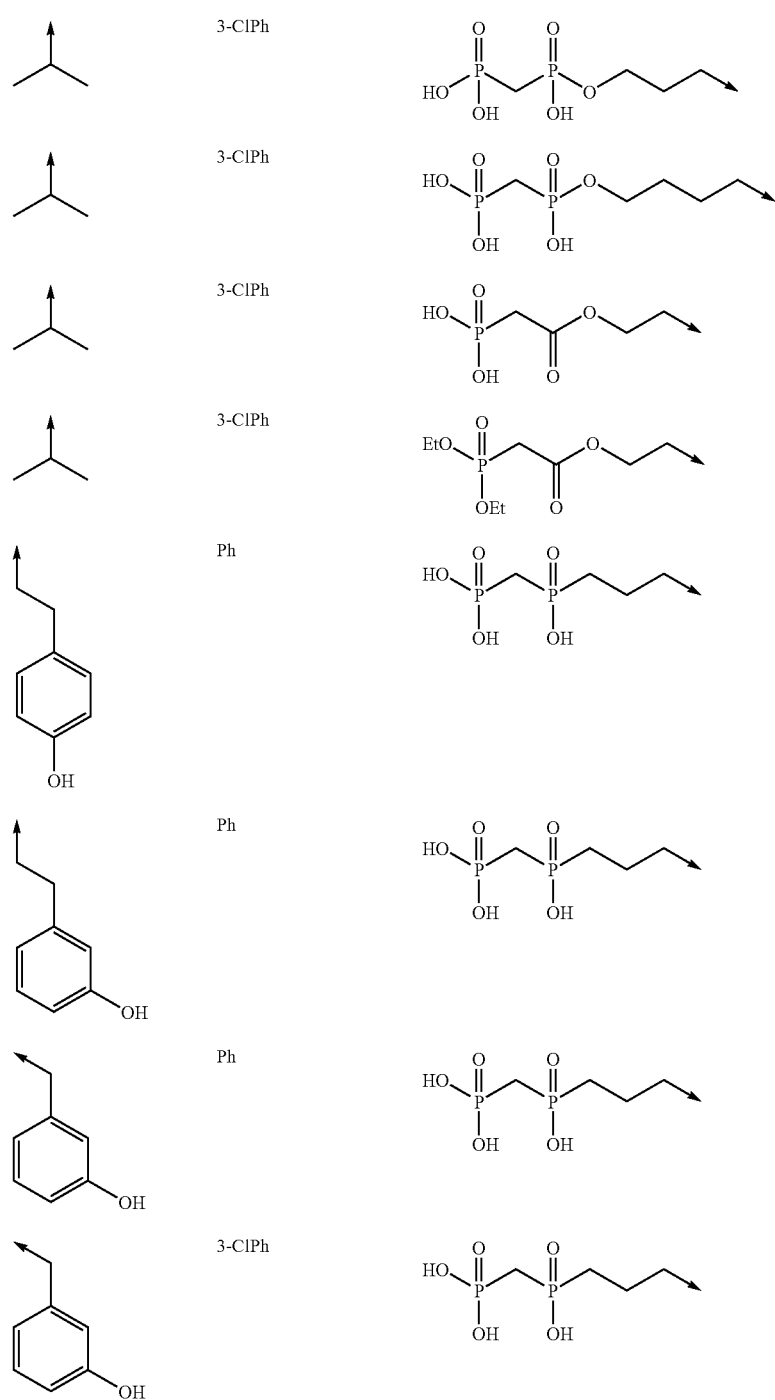

-continued
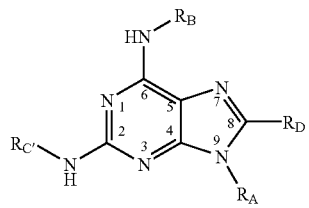
R_D is hydrogen
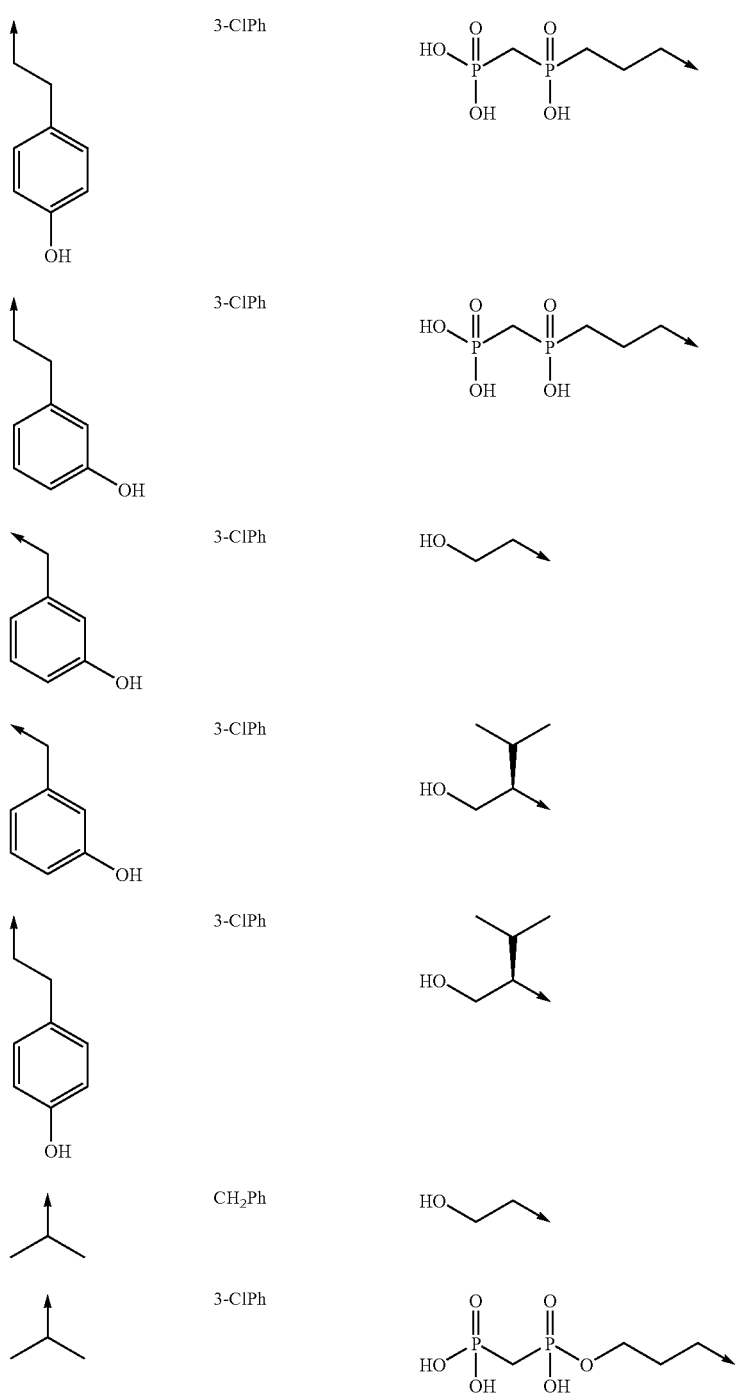

-continued
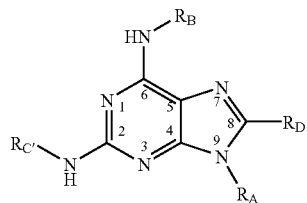
$R_D$ is hydrogen
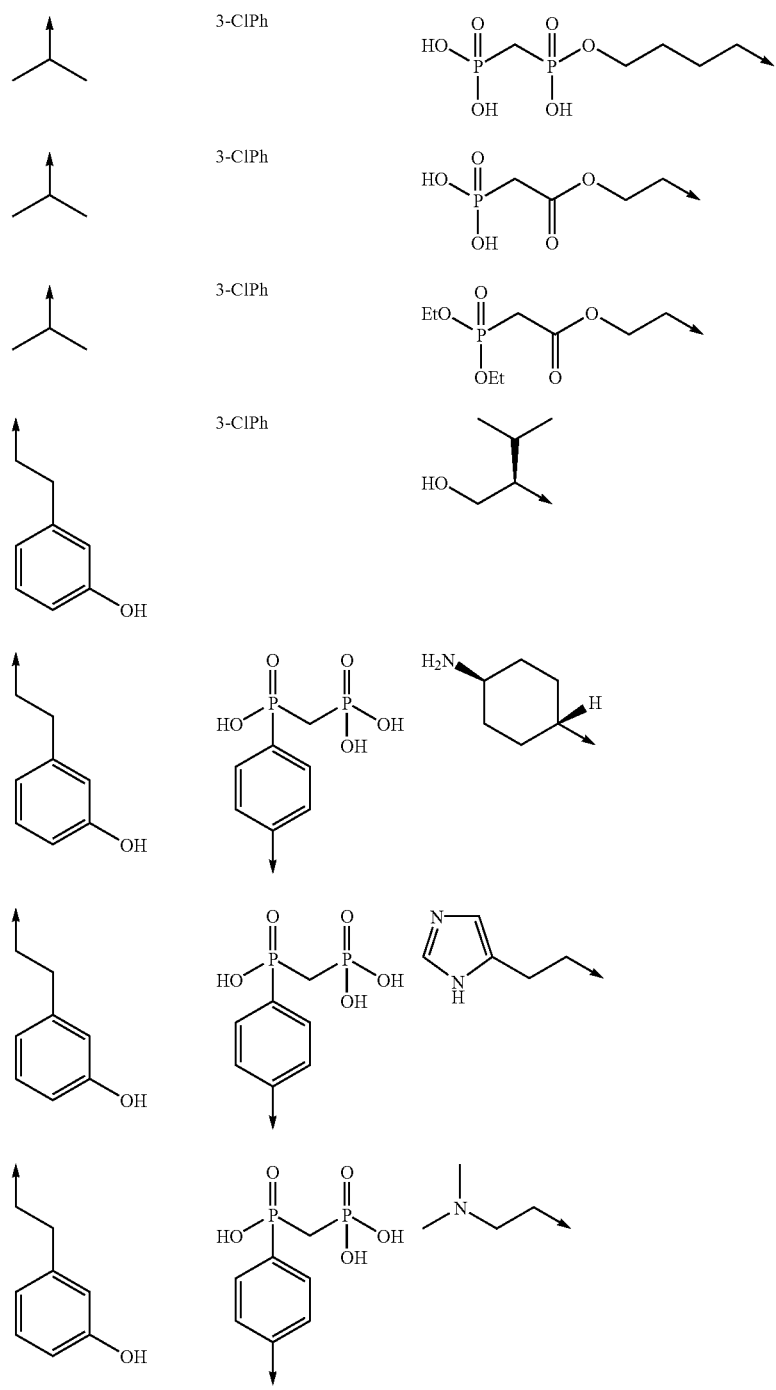

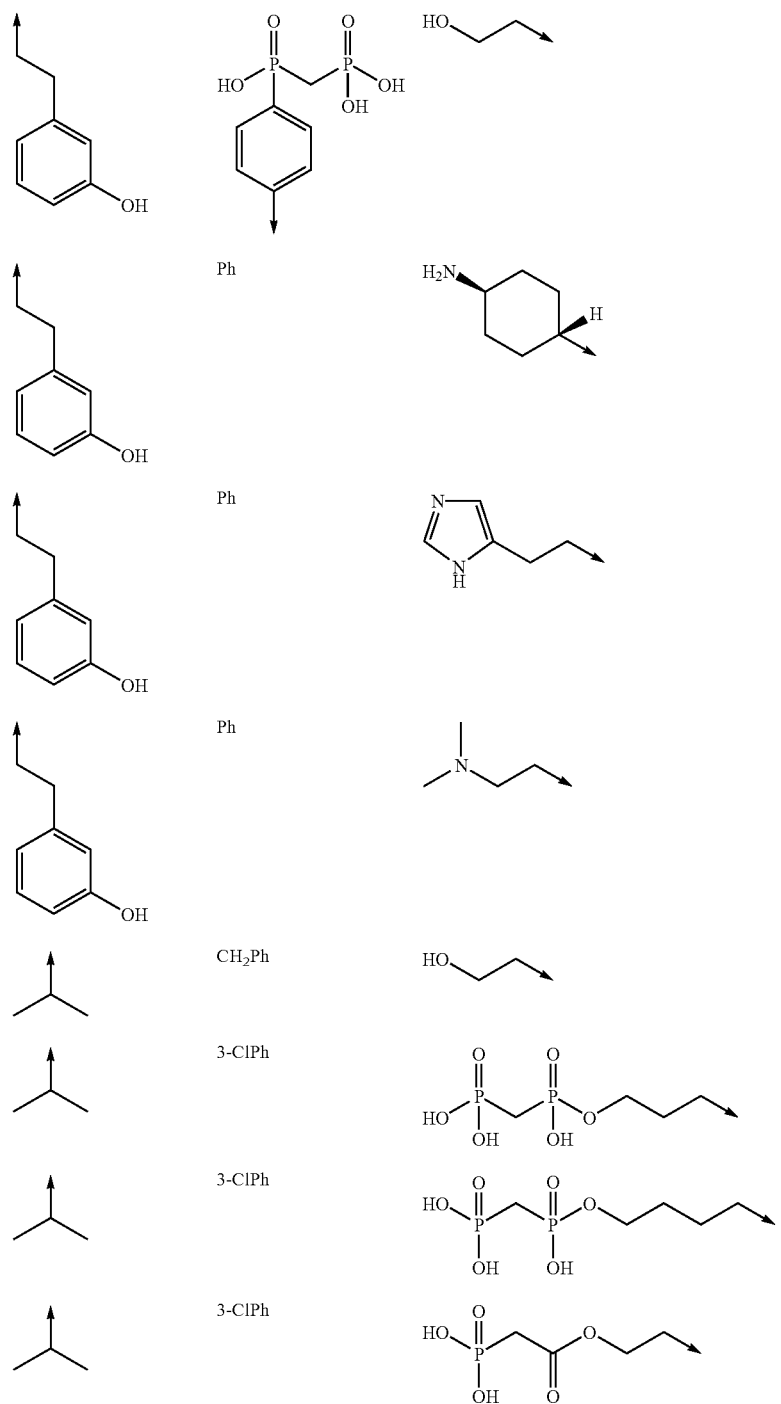

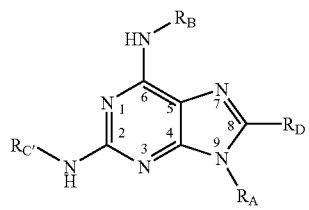
$R_D$ is hydrogen
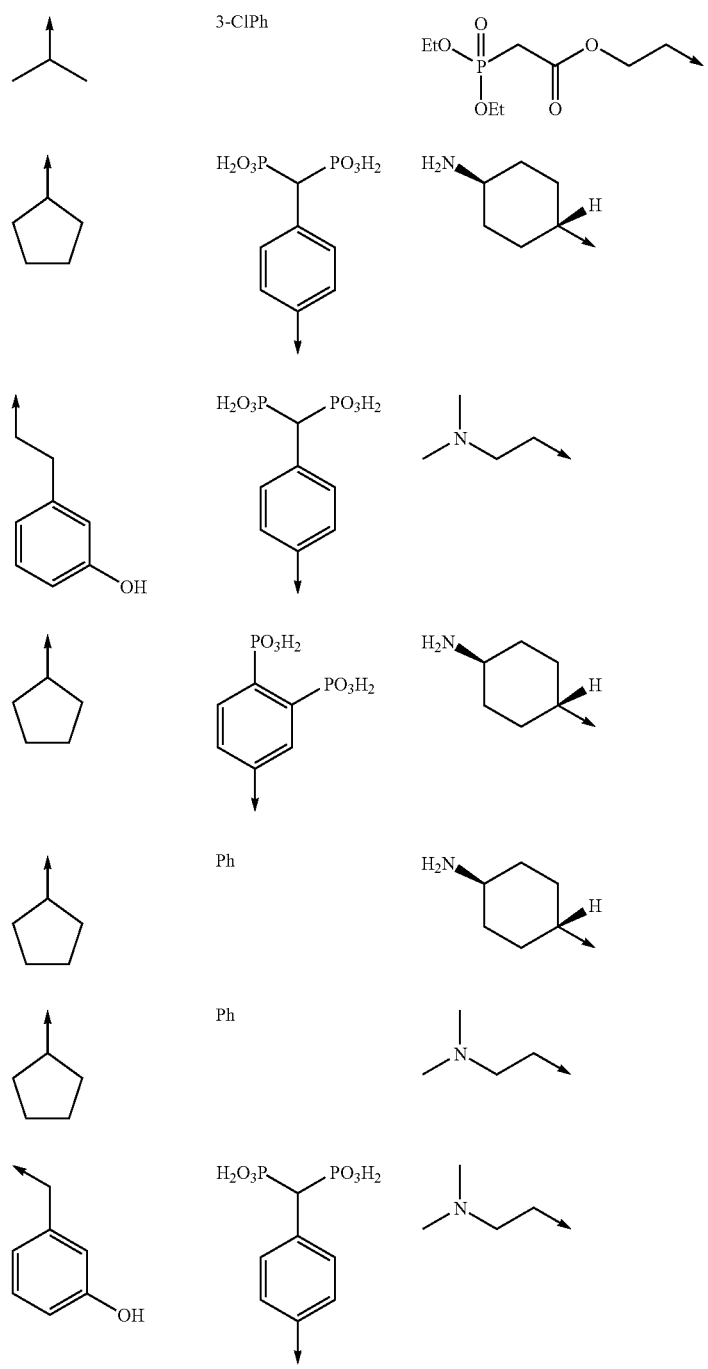

-continued
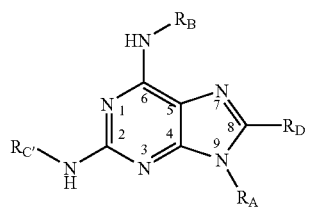
R_D is hydrogen
| | | |
|---|---|---|
| 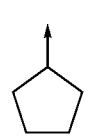 | 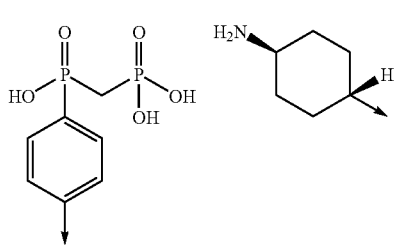 | |
| 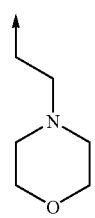 | Ph | |
| 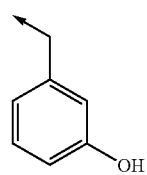 | Ph | |
|  |  CH₂Ph | 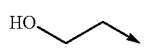 |
|  |  3-ClPh | 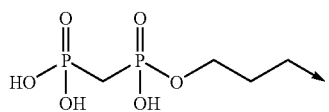 |
|  |  3-ClPh | 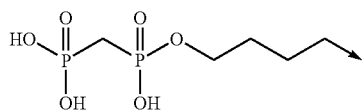 |
|  |  3-ClPh | 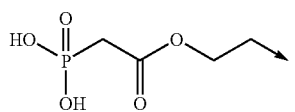 |
|  |  3-ClPh | 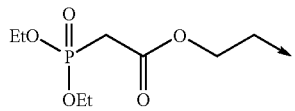 |

-continued
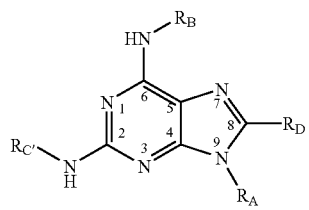
R_D is hydrogen
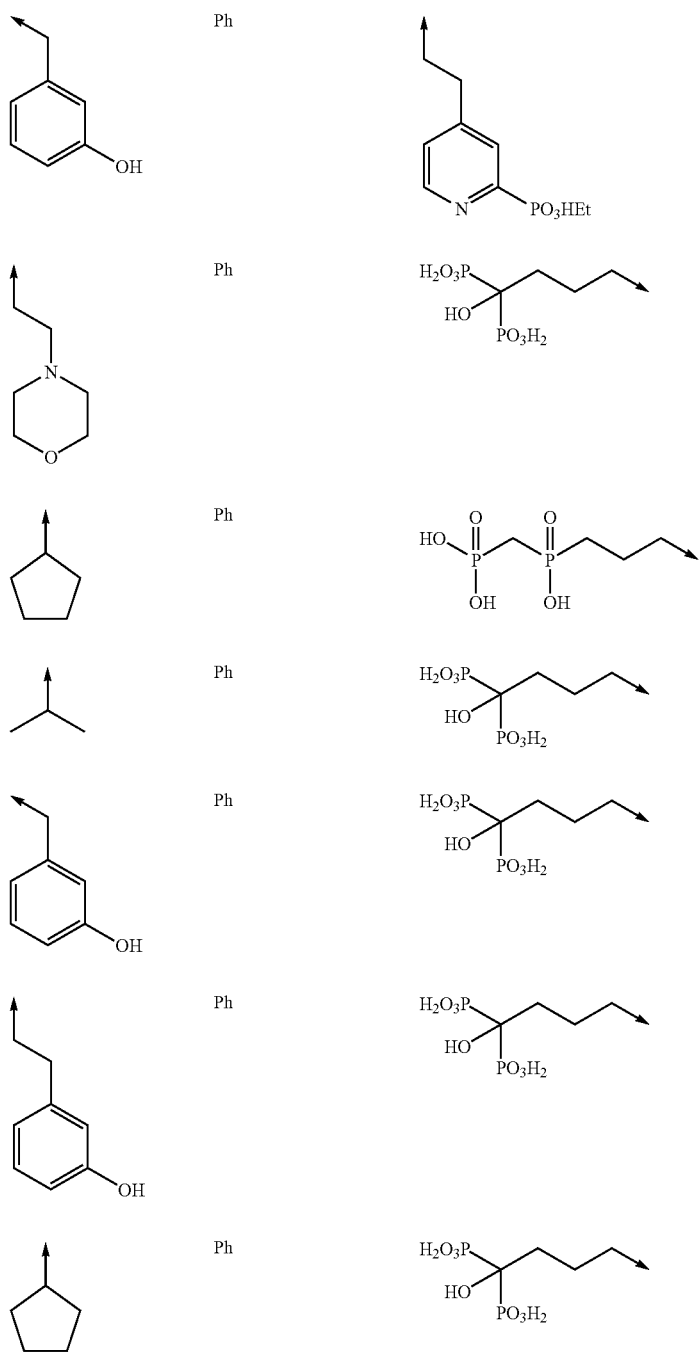

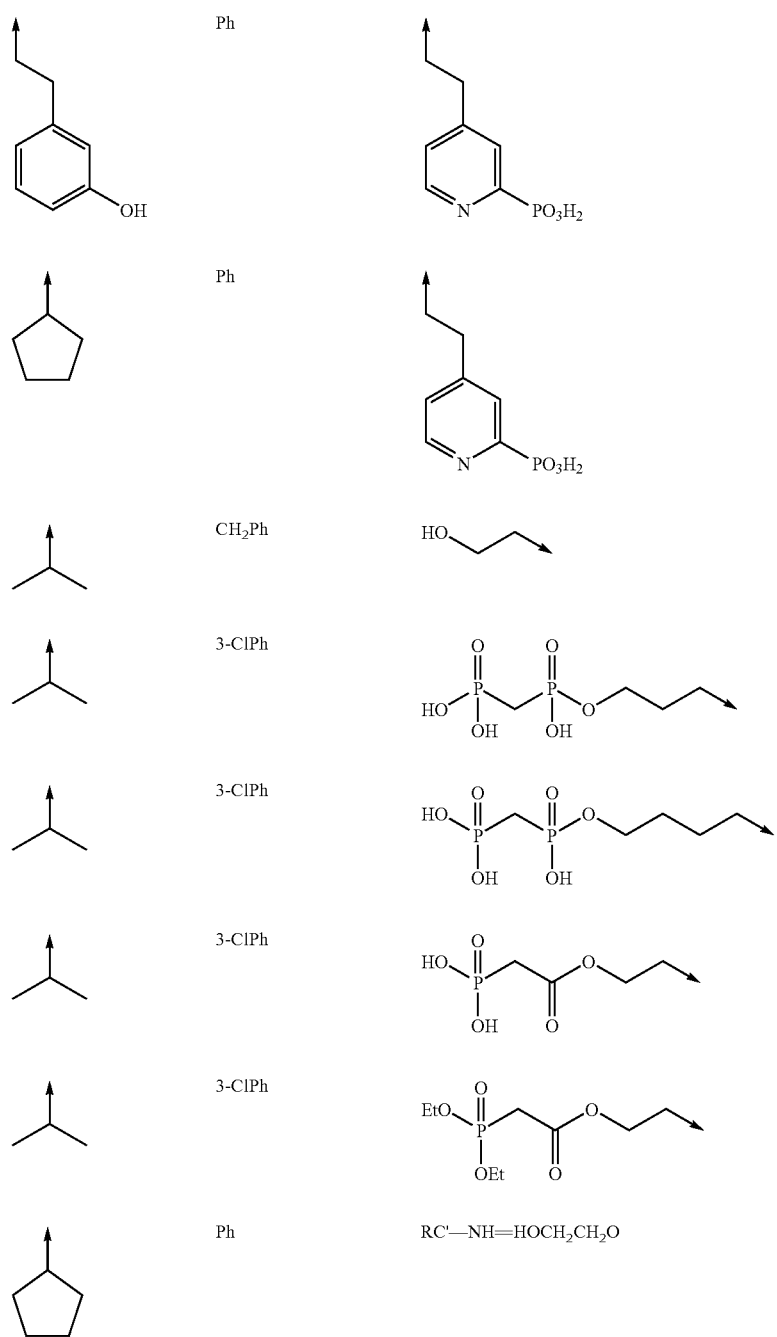

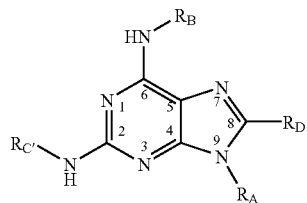
$R_D$ is hydrogen
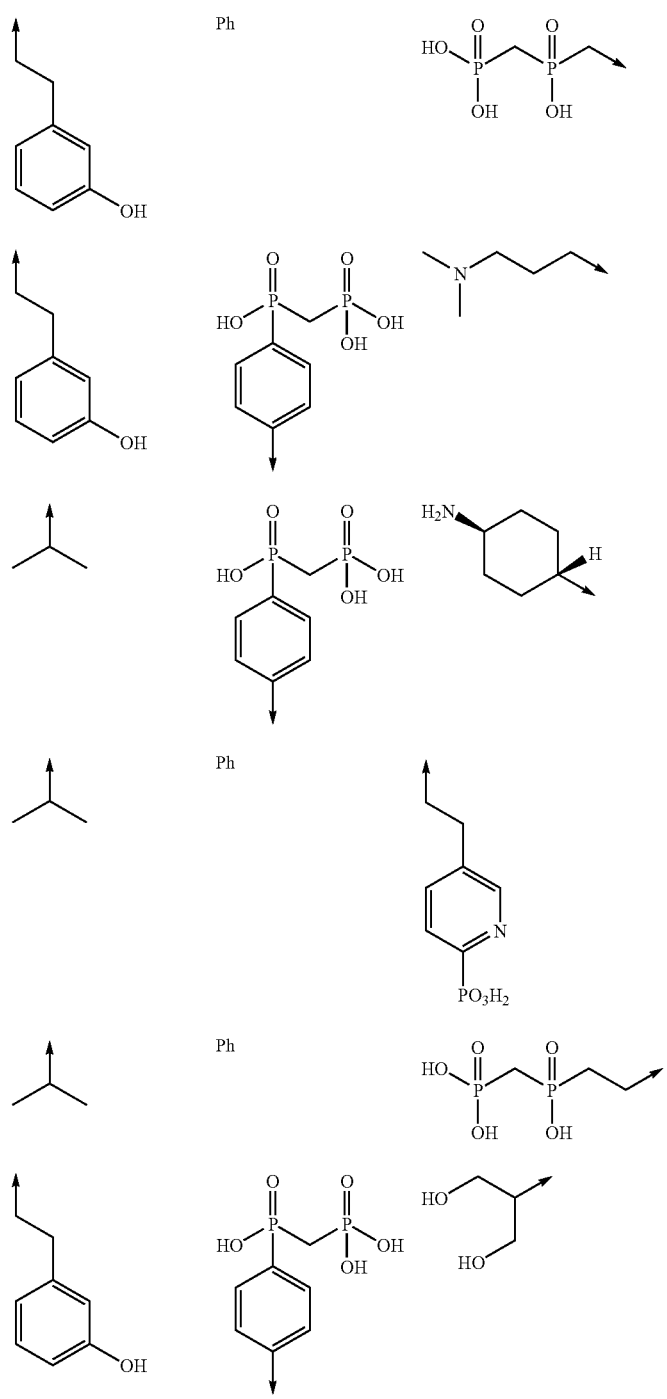

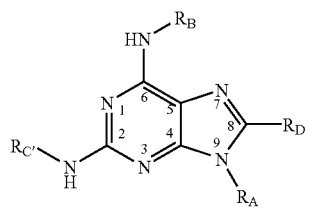
$R_D$ is hydrogen
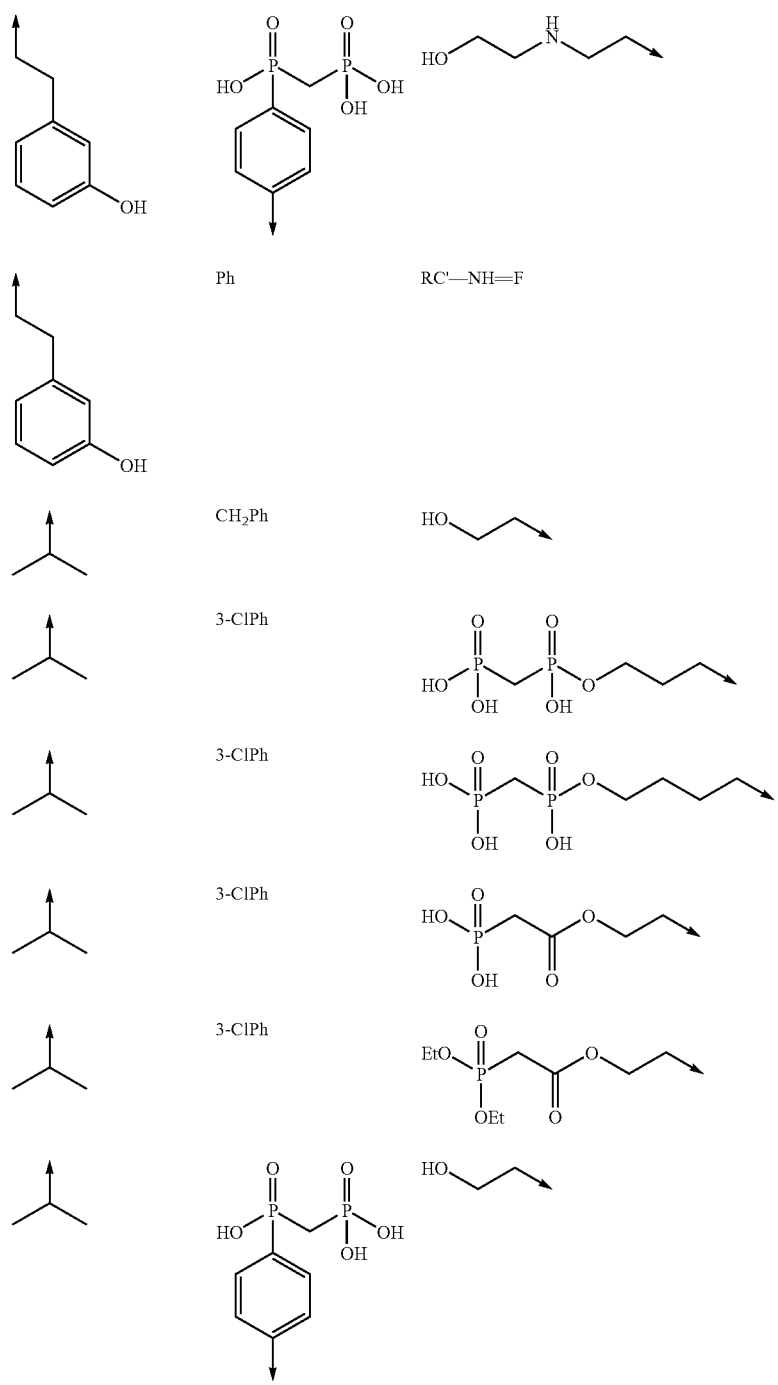

-continued
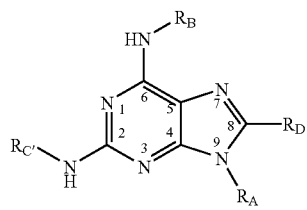
$R_D$ is hydrogen
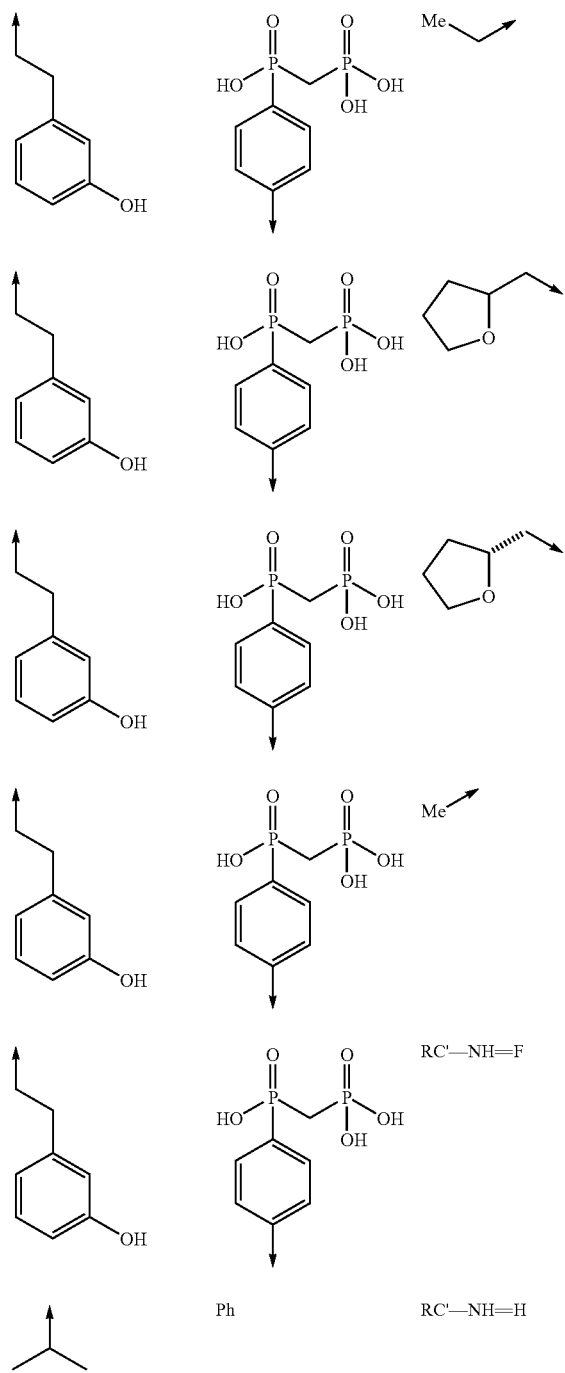

-continued
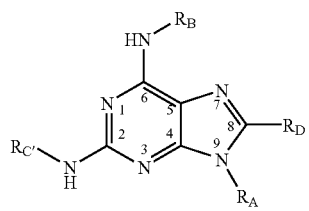
$R_D$ is hydrogen
| $R_A$ | $R_B$ | $R_{C'}$—NH |
|---|---|---|
| 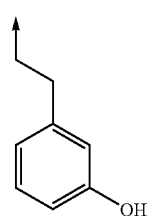 | Ph | RC'—NH=H |
|  | Ph | 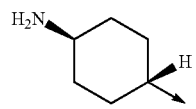 |
|  | CH₂Ph | 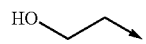 |
|  | 3-ClPh | 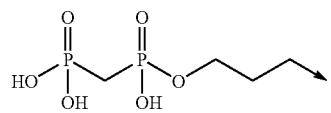 |
|  | 3-ClPh | 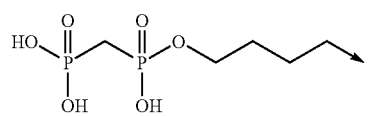 |
|  | 3-ClPh | 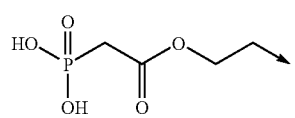 |
|  | 3-ClPh | 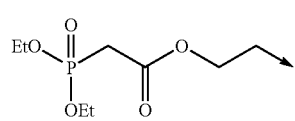 |
|  | | 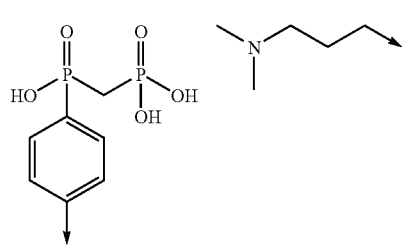 |

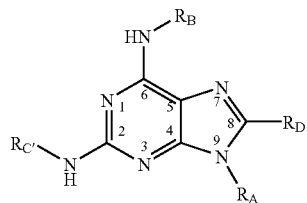
$R_D$ is hydrogen
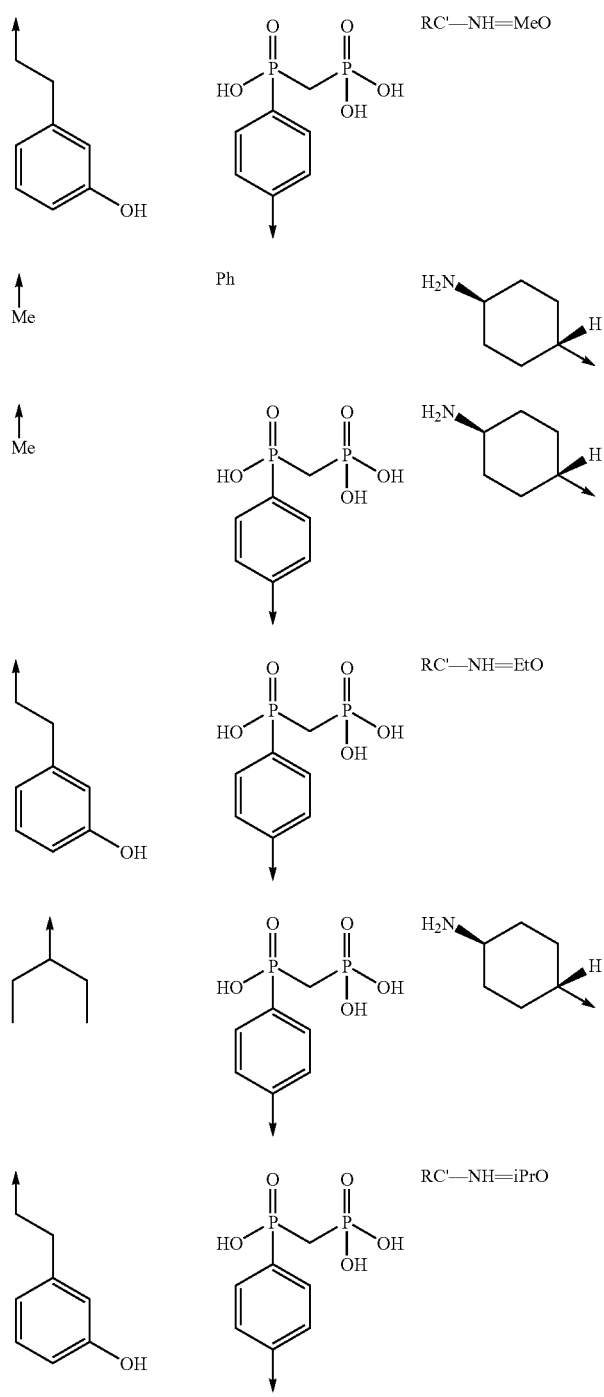

-continued
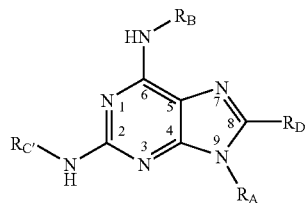
R_D is hydrogen
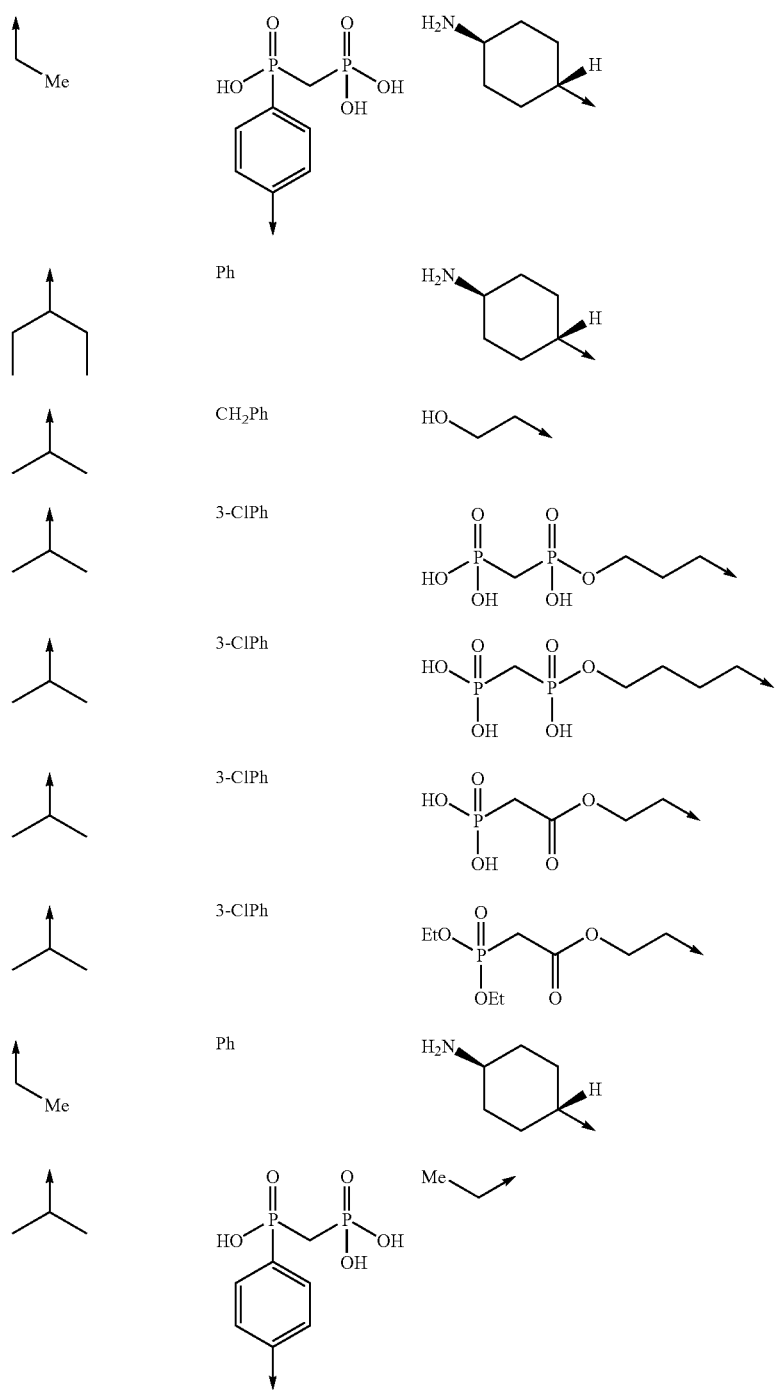

-continued
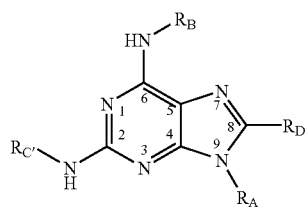
R_D is hydrogen
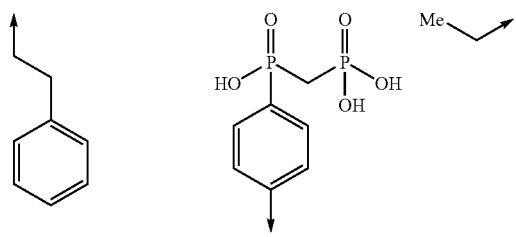
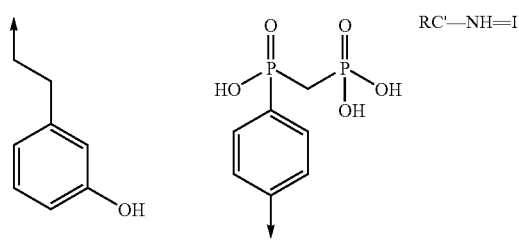
RC'—NH=I
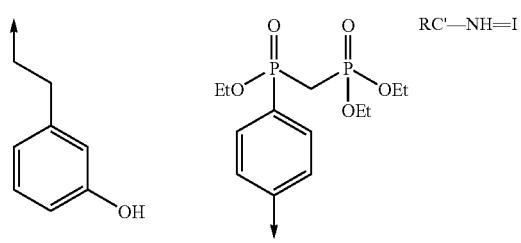
RC'—NH=I
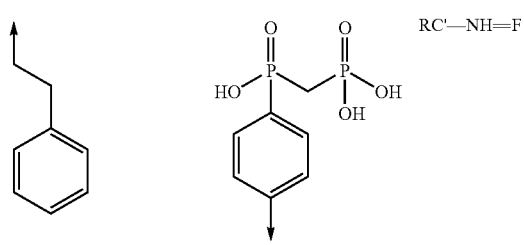
RC'—NH=F
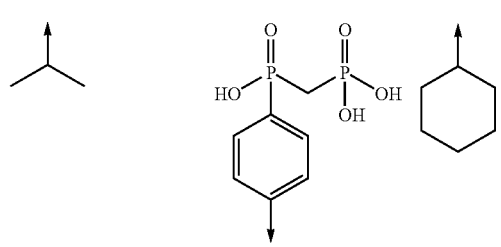

-continued
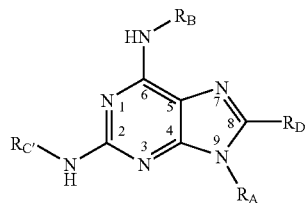
$R_D$ is hydrogen
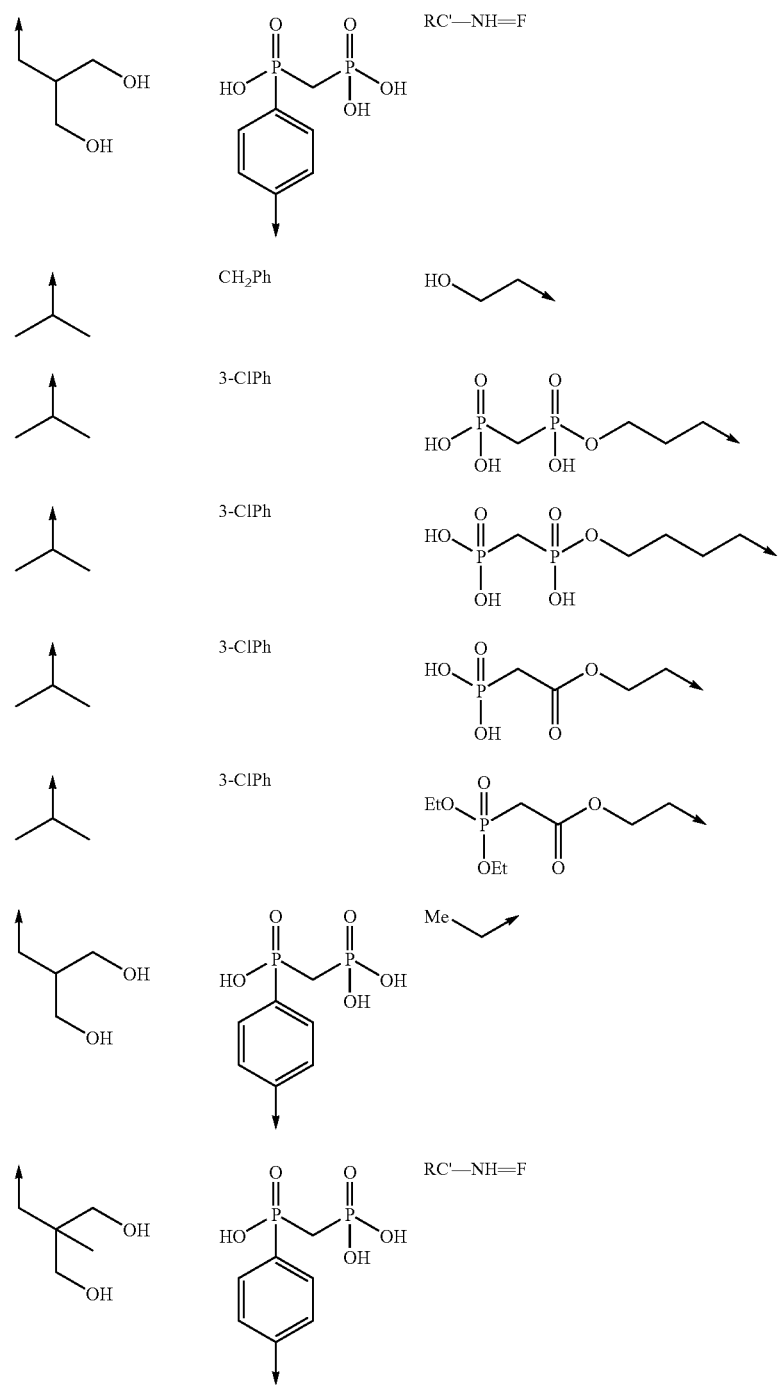

-continued
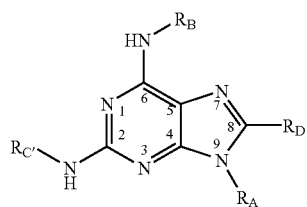
$R_D$ is hydrogen
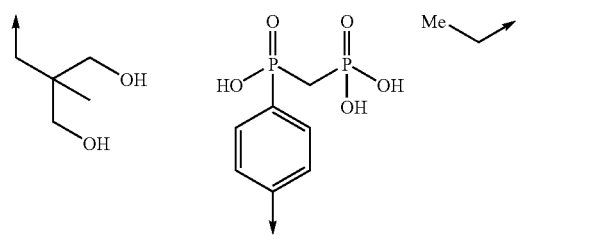
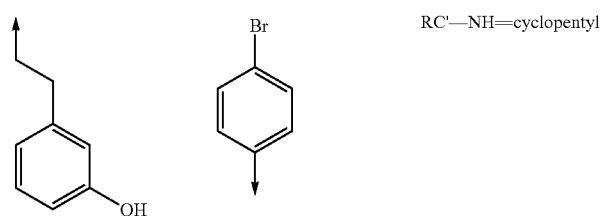    RC'—NH=cyclopentyl
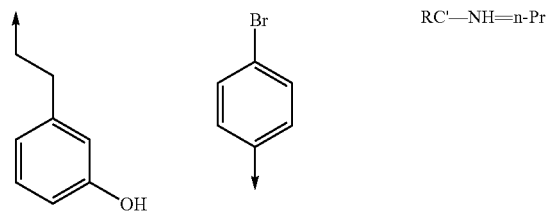    RC'—NH=n-Pr
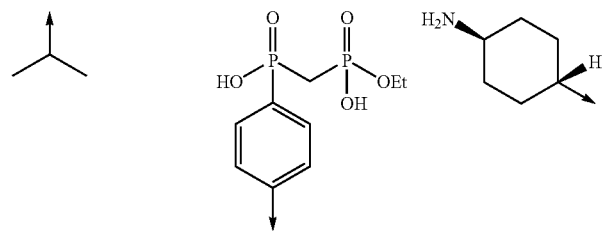
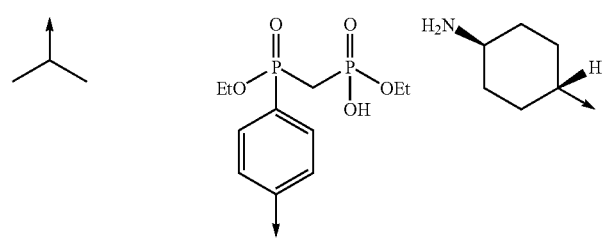

-continued
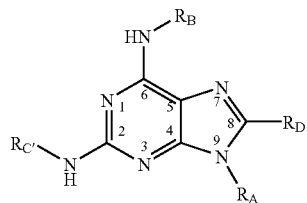
$R_D$ is hydrogen
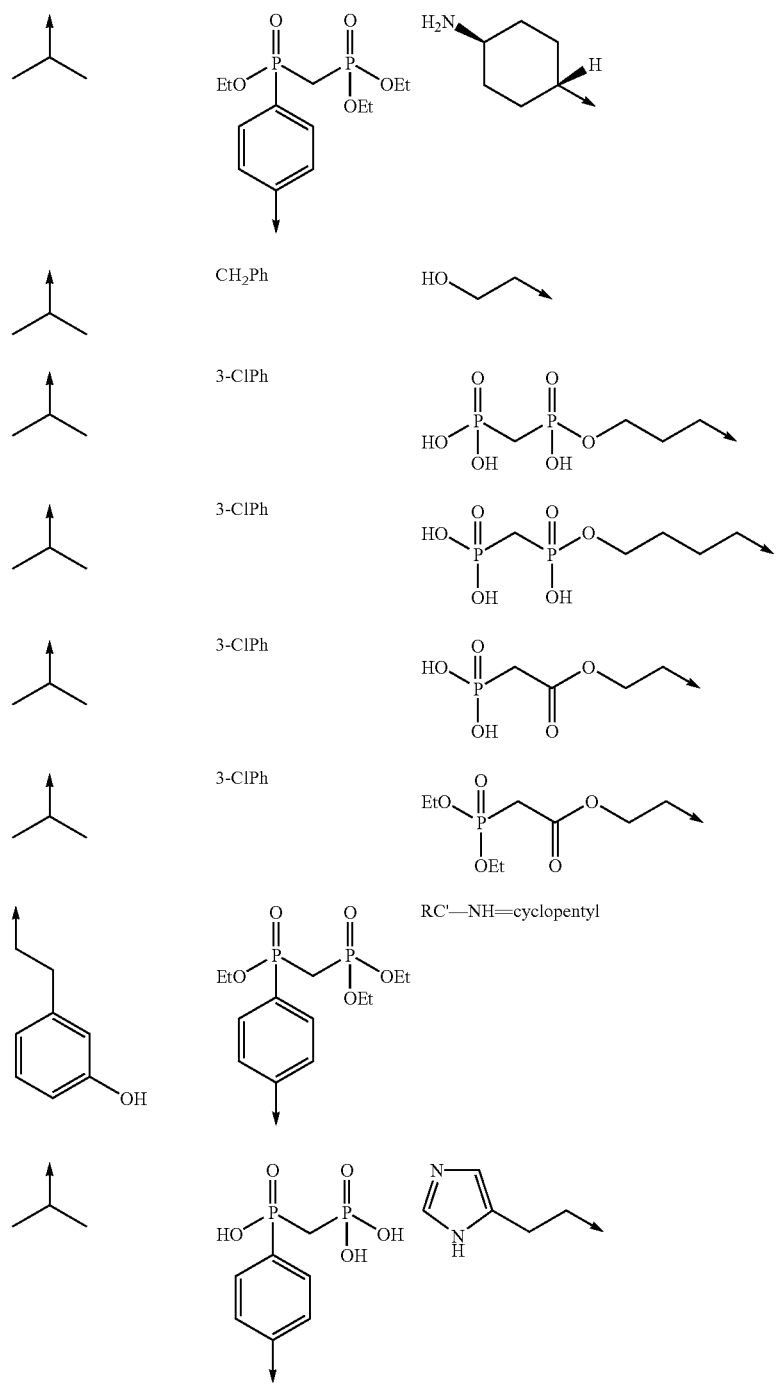

-continued
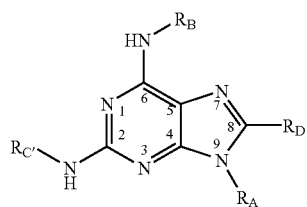
R_D is hydrogen
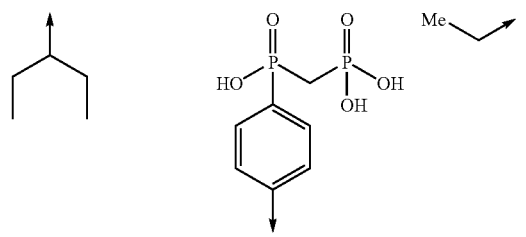
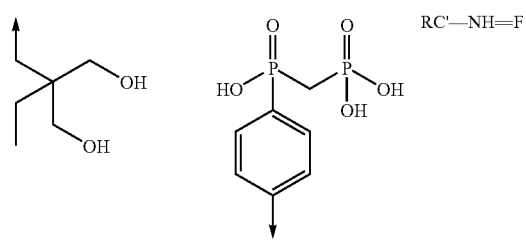 RC'—NH=F
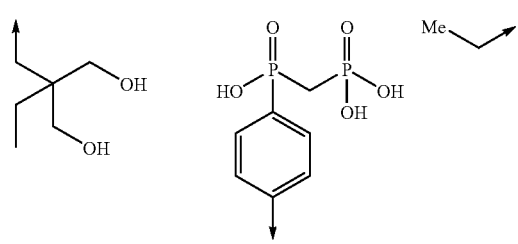
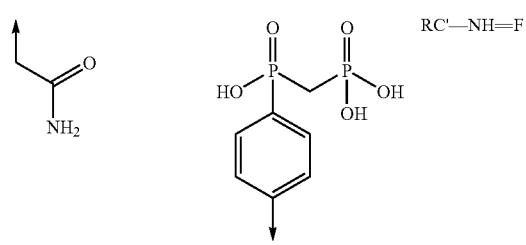 RC'—NH=F
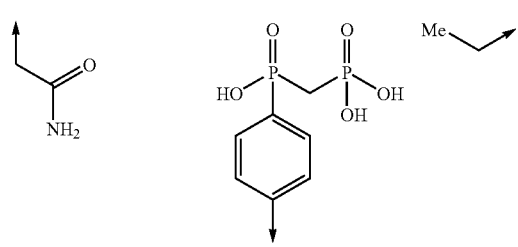

-continued
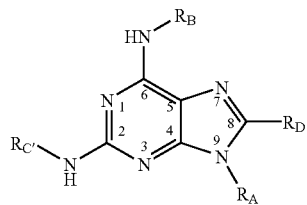
R_D is hydrogen
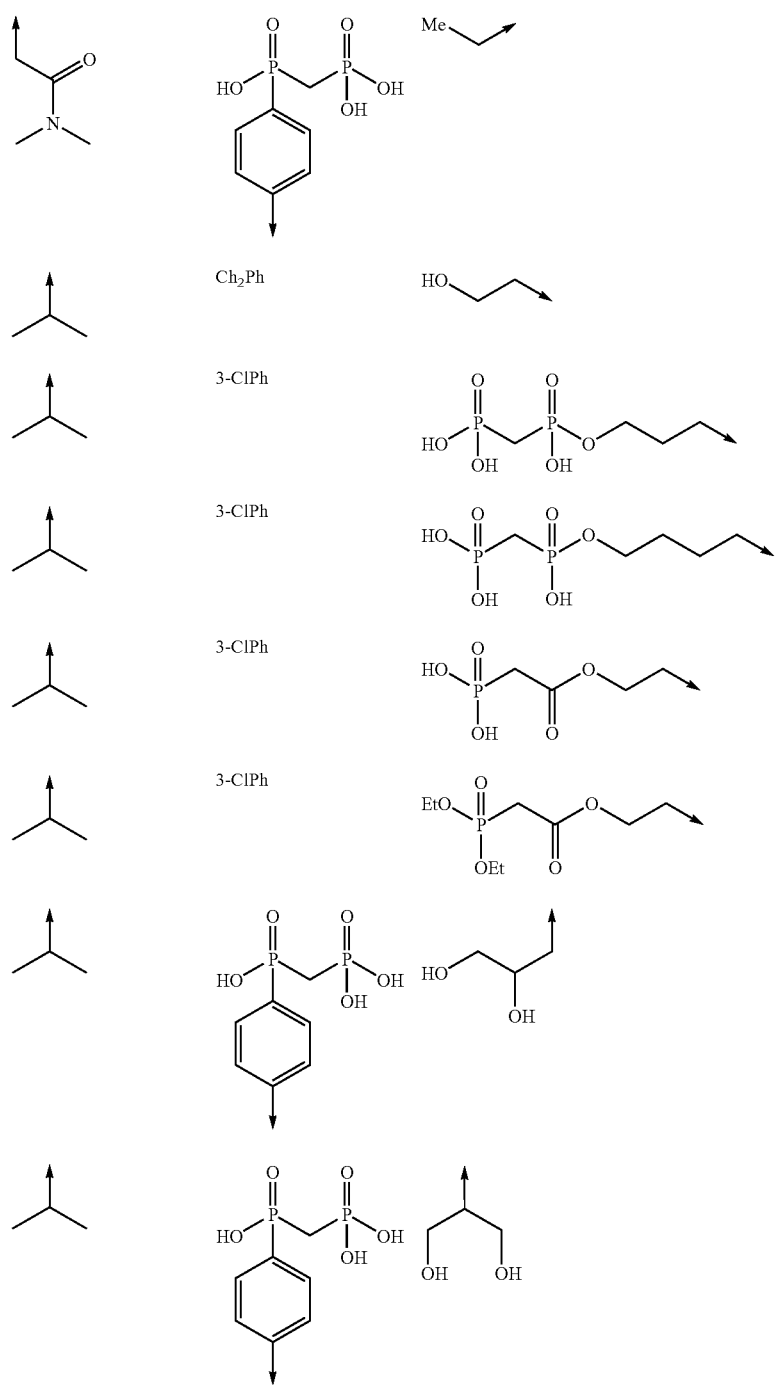

-continued
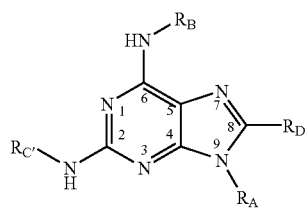
$R_D$ is hydrogen
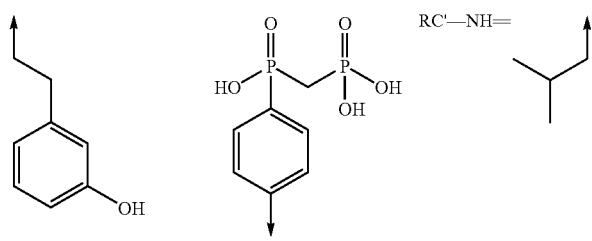
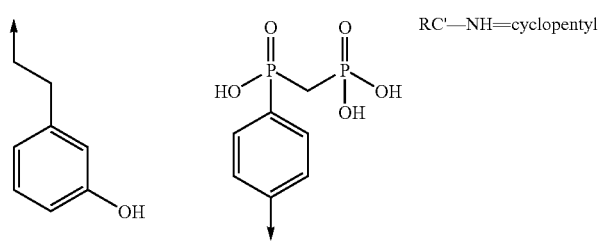 RC'—NH=cyclopentyl
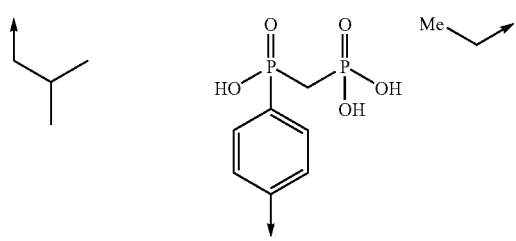
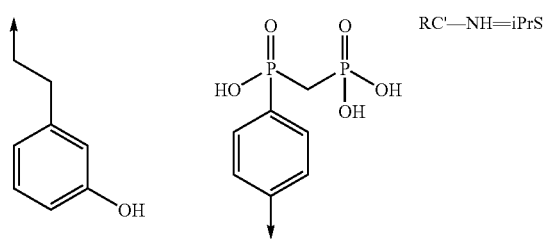 RC'—NH=iPrS
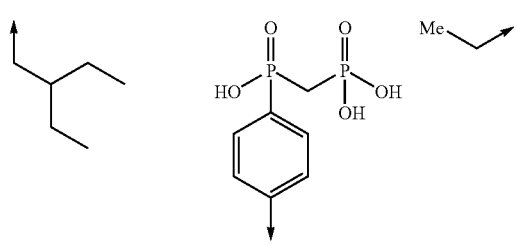

-continued
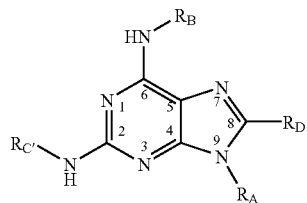
R_D is hydrogen
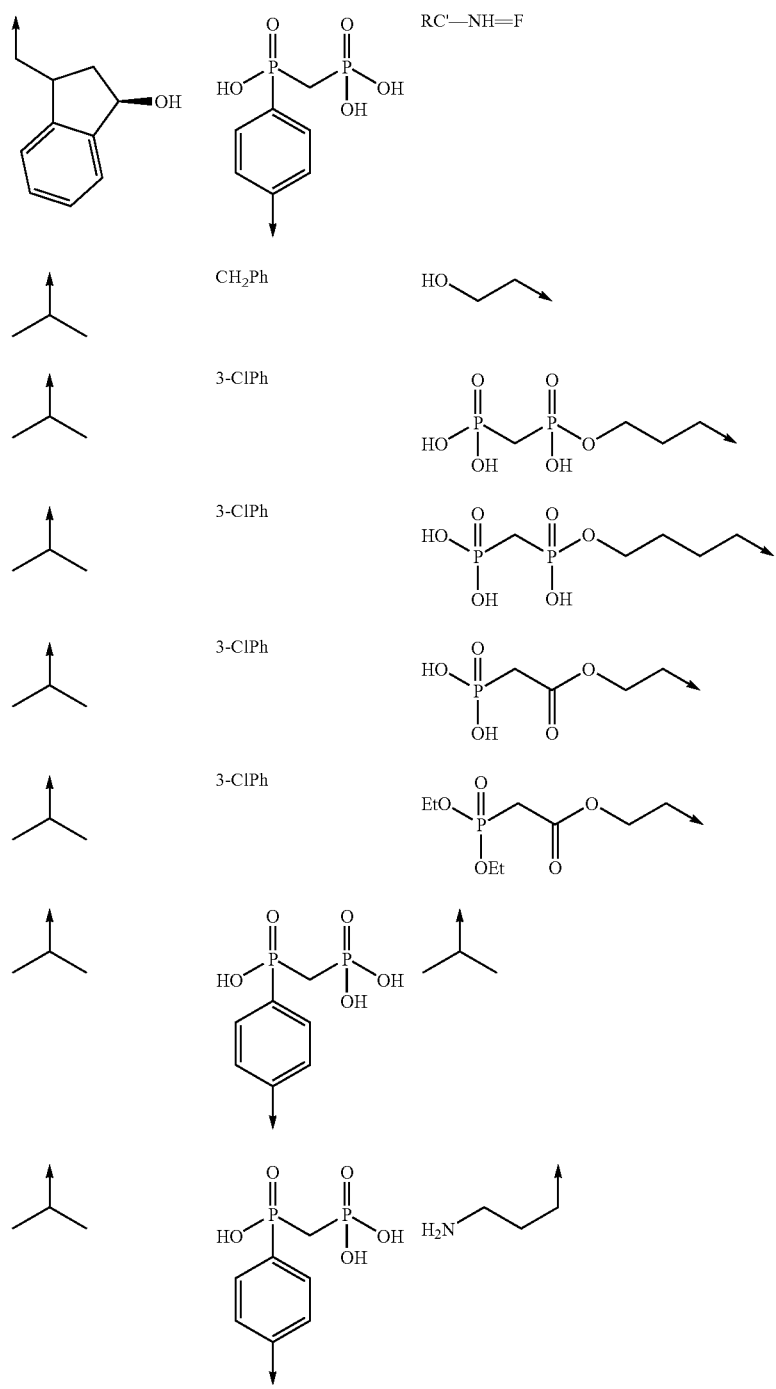

-continued
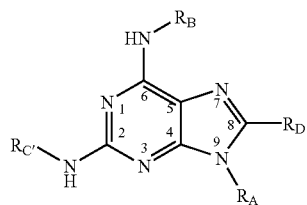
R_D is hydrogen
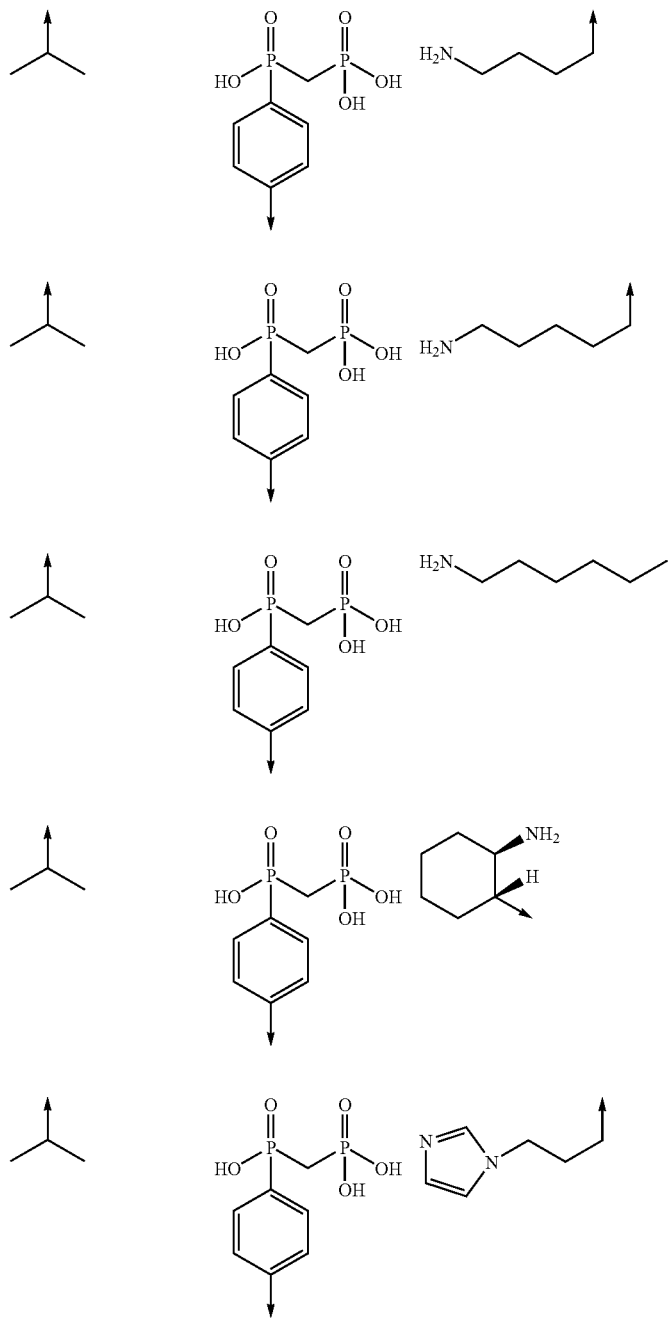

-continued
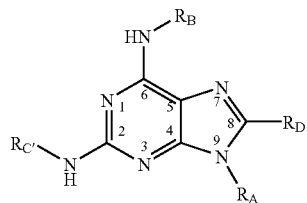
$R_D$ is hydrogen
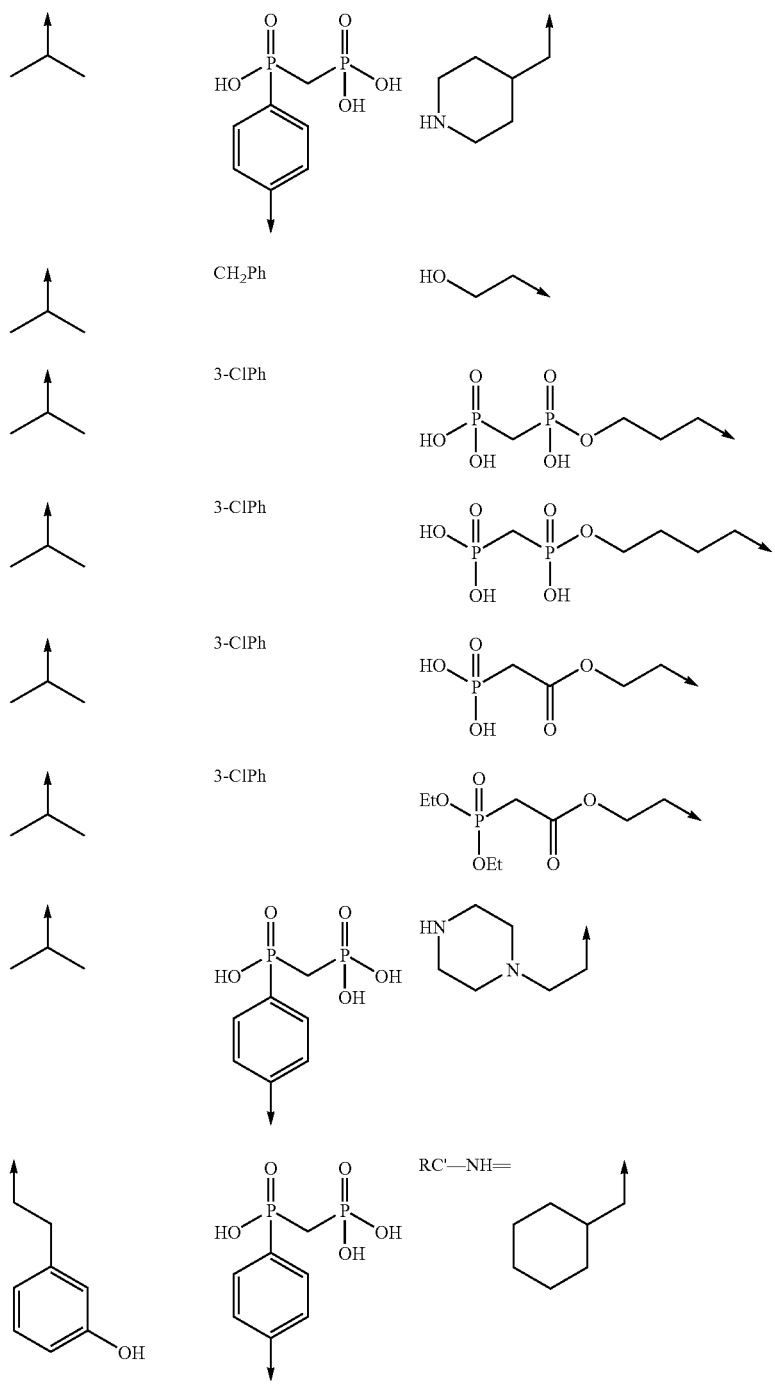

-continued
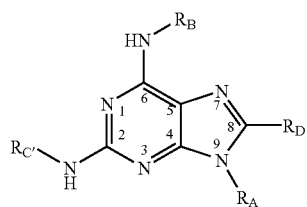
R_D is hydrogen
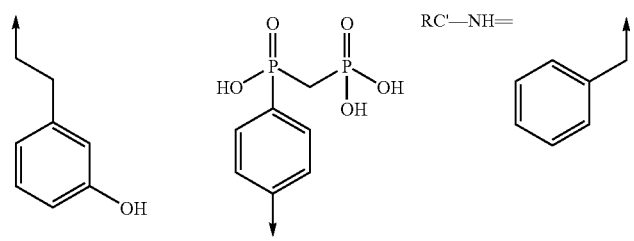
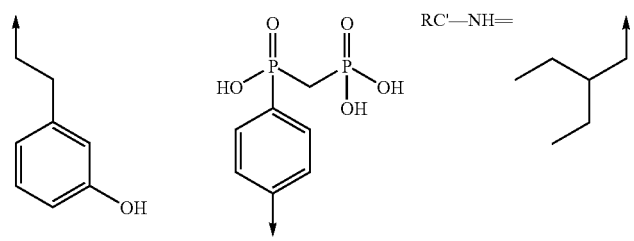
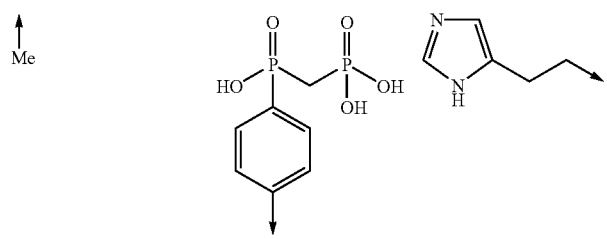
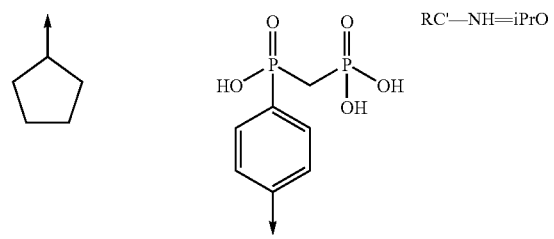
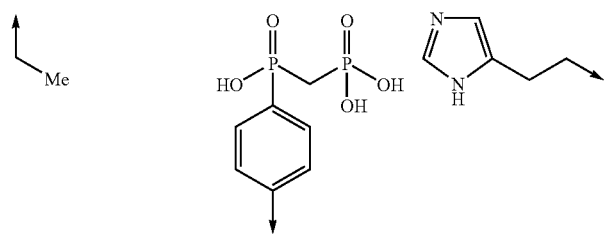

-continued
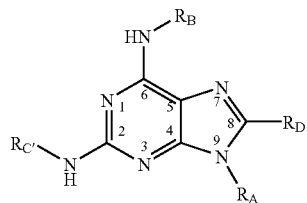
$R_D$ is hydrogen
| | | |
|---|---|---|
|  | 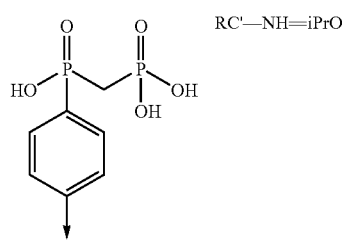 | RC'—NH=iPrO |
|  | CH$_2$PH | 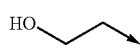 |
|  | 3-ClPh | 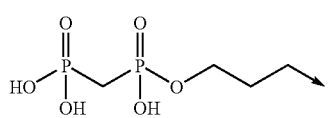 |
|  | 3-ClPh | 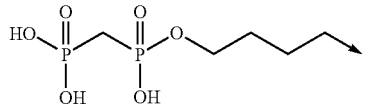 |
|  | 3-ClPh | 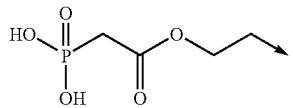 |
|  | 3-ClPh | 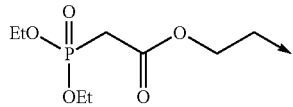 |
|  | 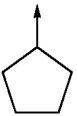 | RC'—NH= 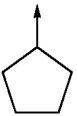 |
| | 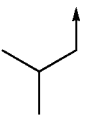 | RC'—NH= |

-continued
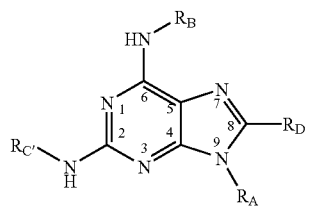
R_D is hydrogen
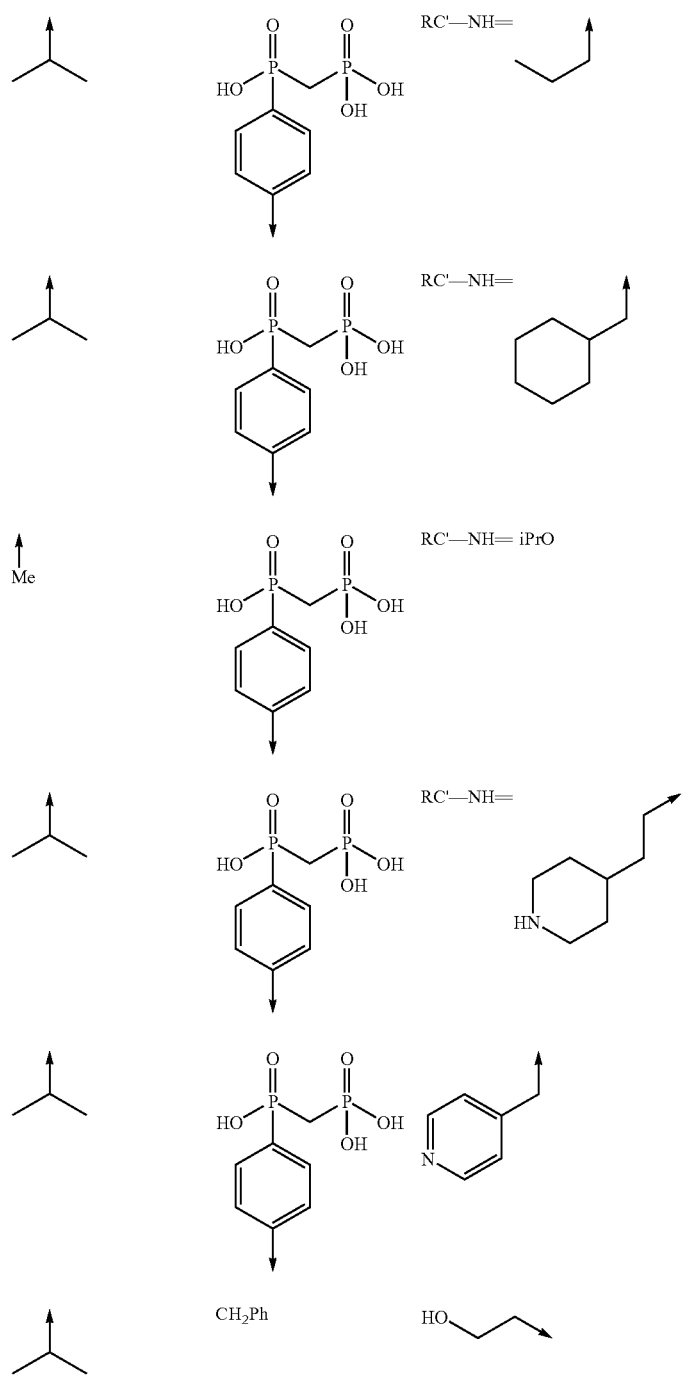

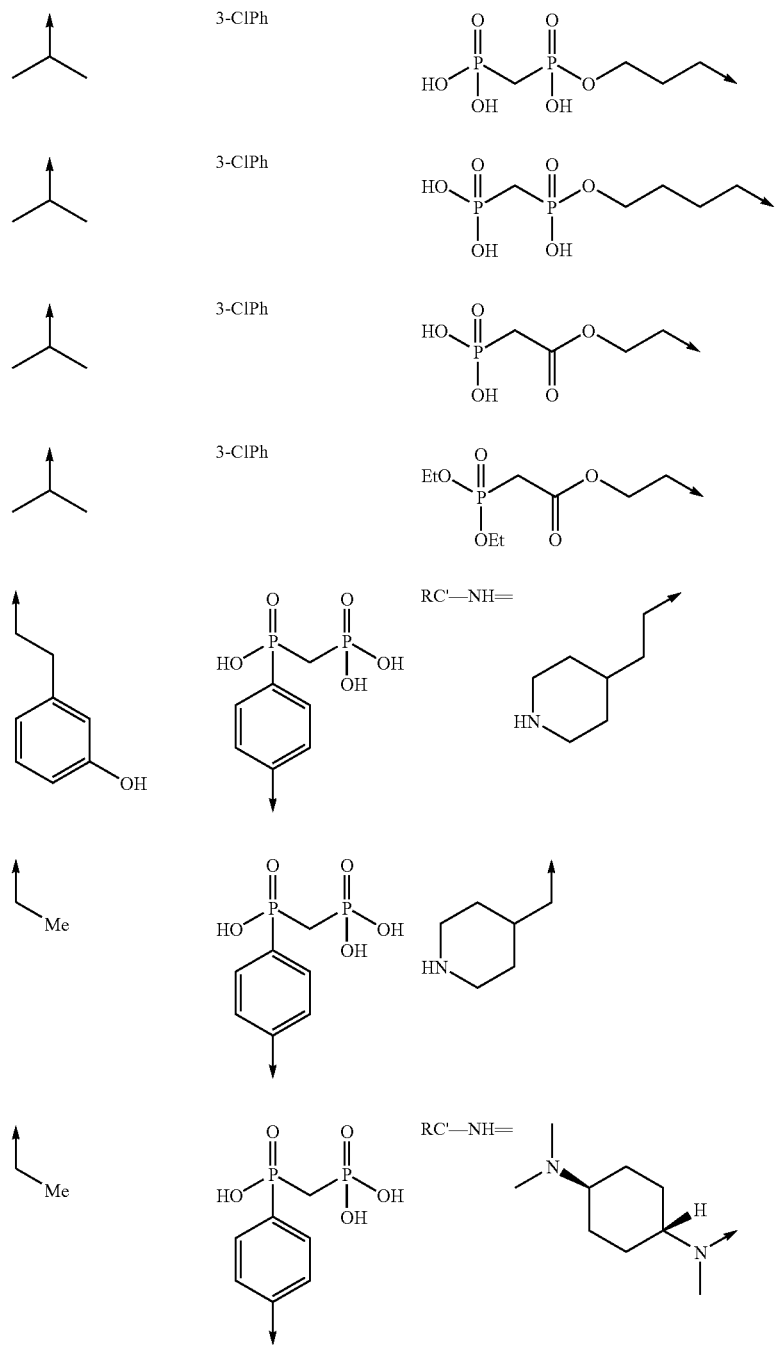

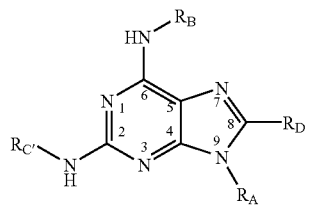
$R_D$ is hydrogen
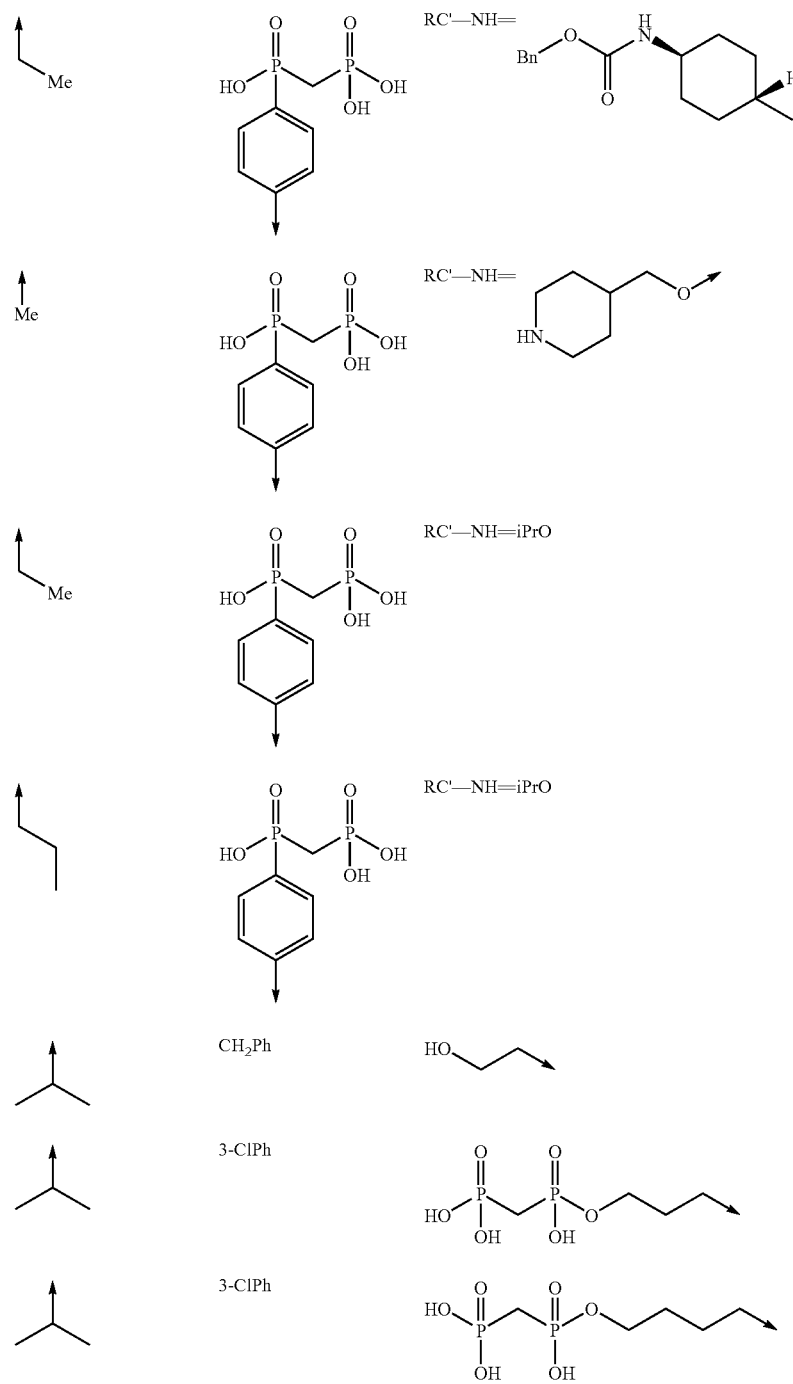

-continued
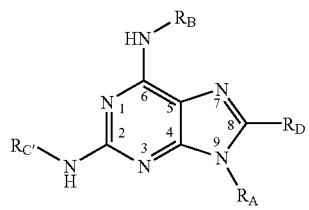
$R_D$ is hydrogen
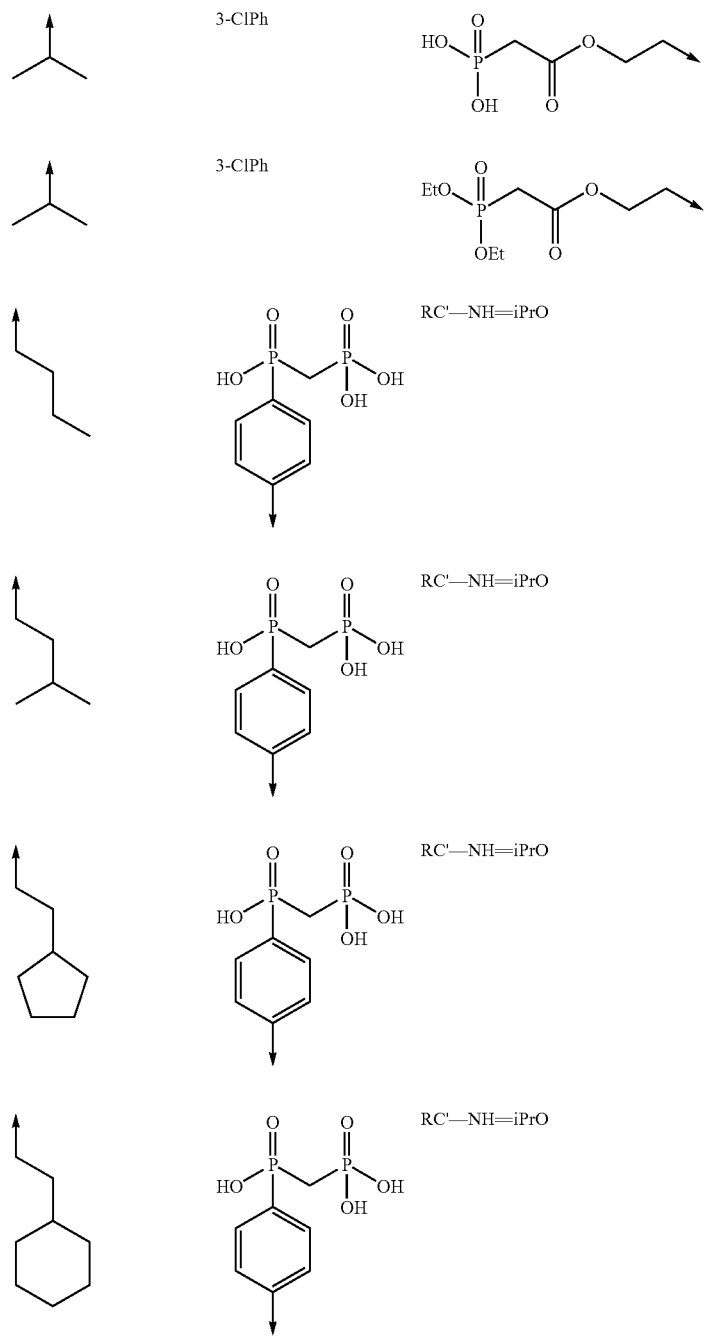

-continued
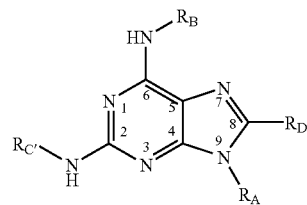
R_D is hydrogen
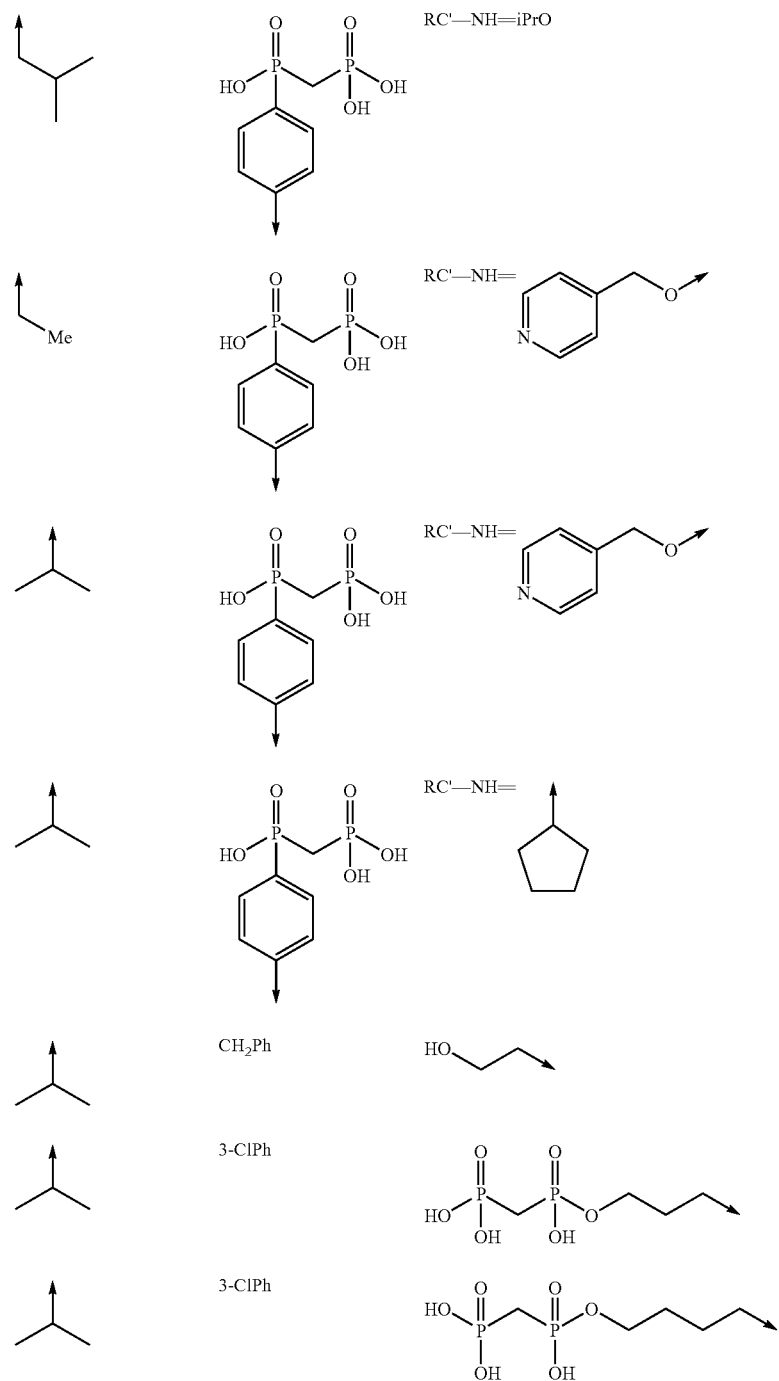

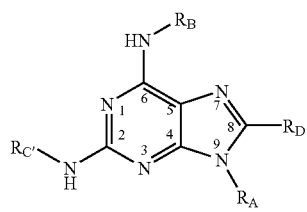
$R_D$ is hydrogen
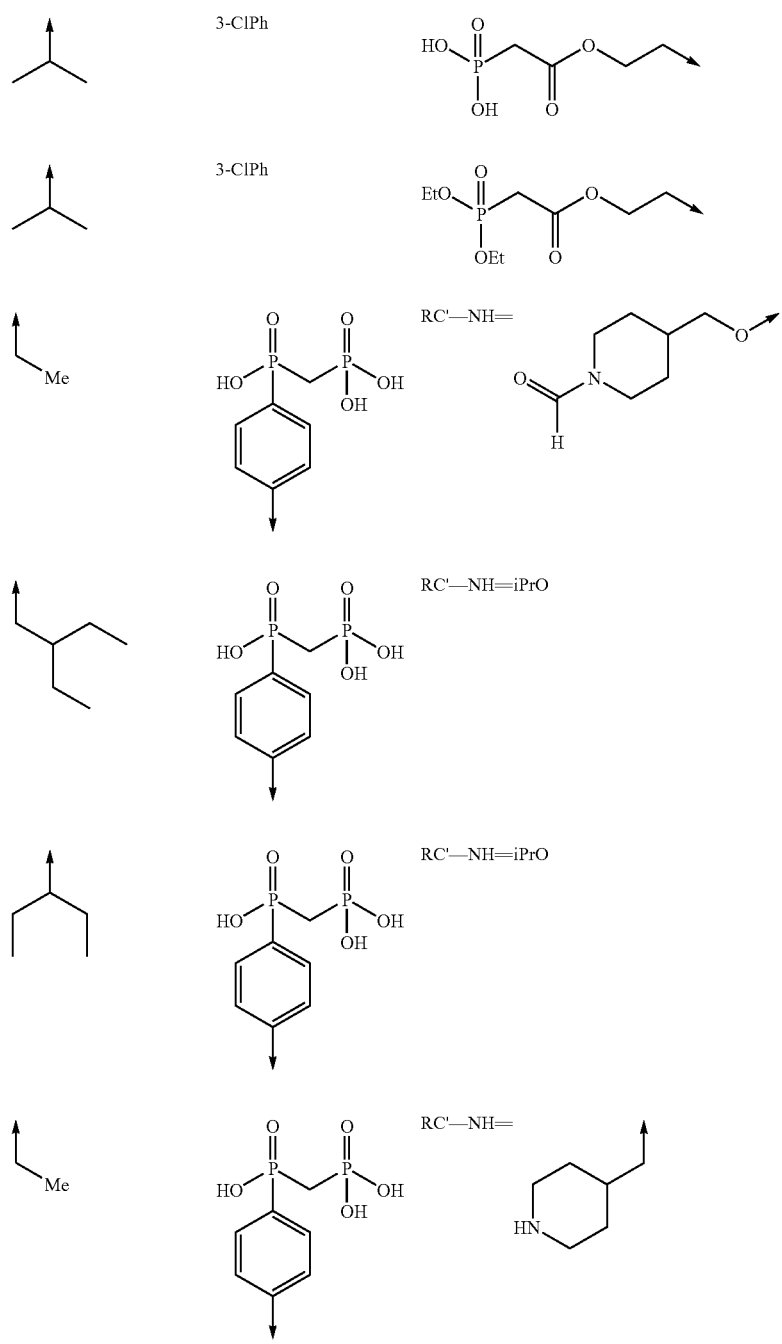

-continued
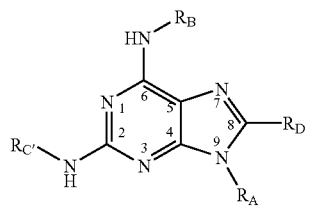
R_D is hydrogen
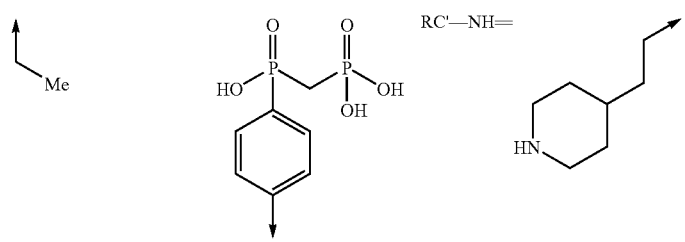
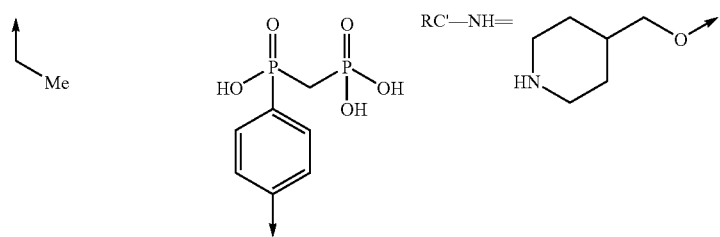
Certain other exemplary compounds as depicted below can be synthesized in a manner similar to that exemplified herein:
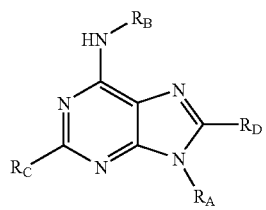
R_D is hydrogen
| R_A | R_B | R_C |
|---|---|---|
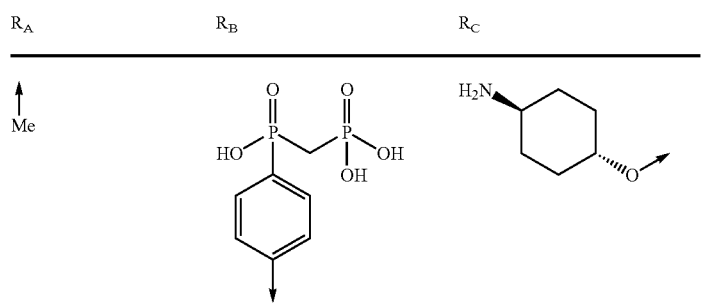

-continued
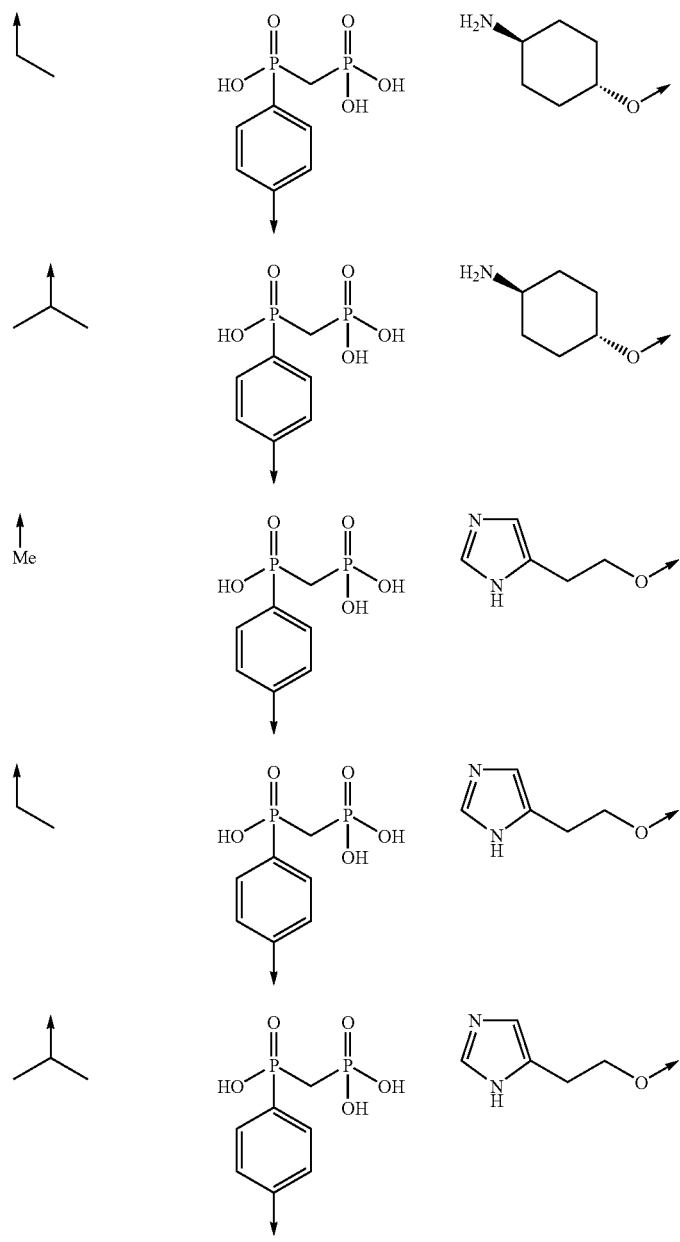
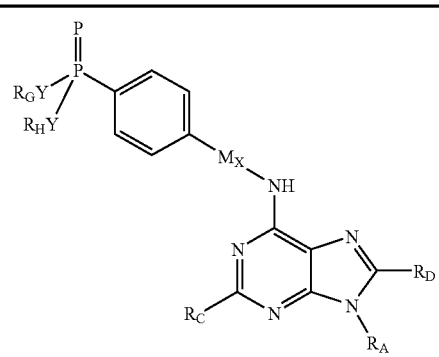
$R_D$ is hydrogen

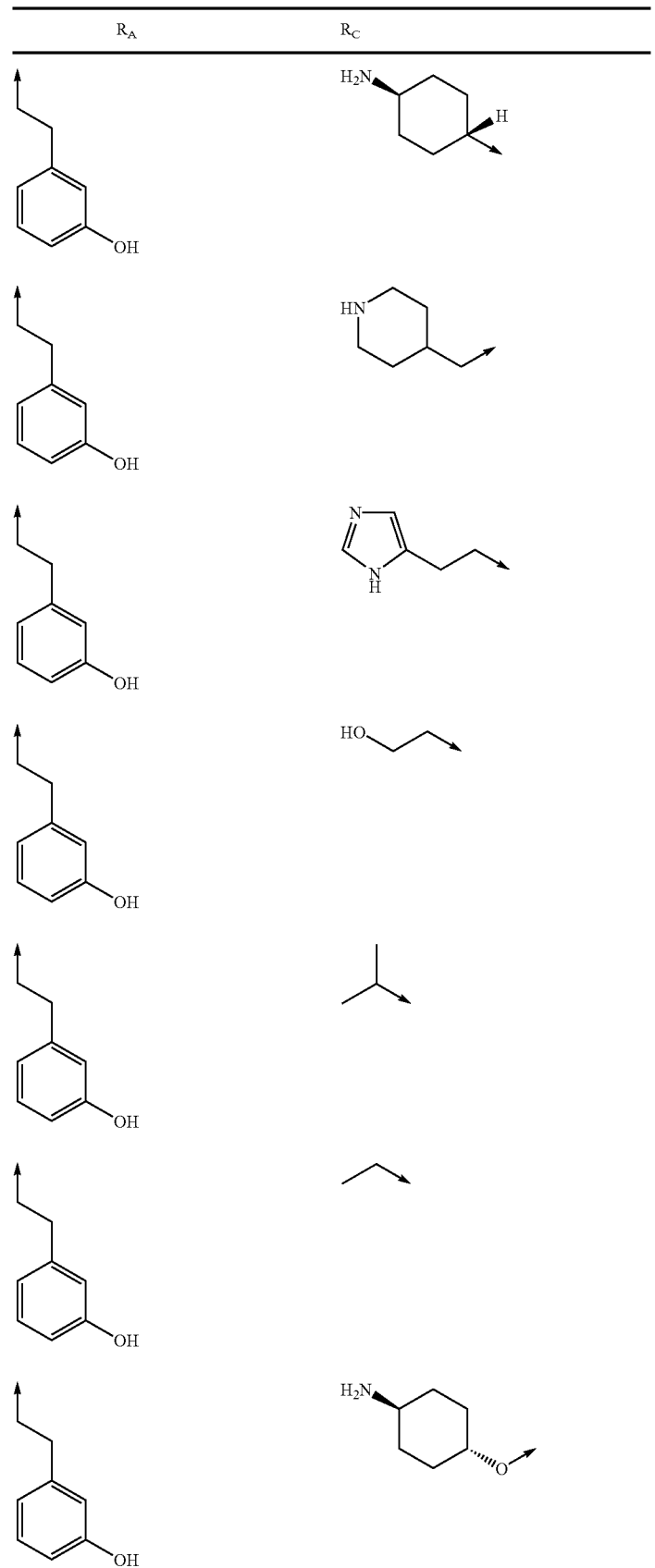

-continued
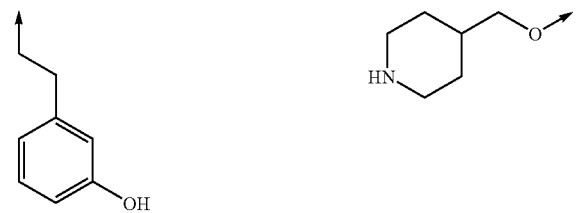
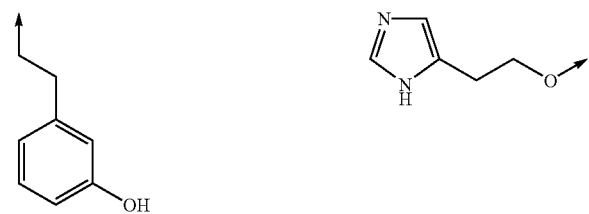
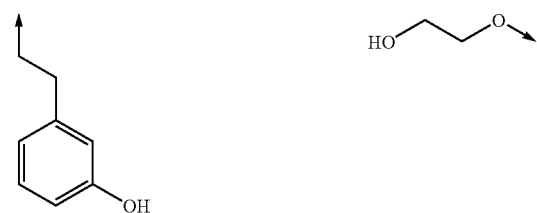
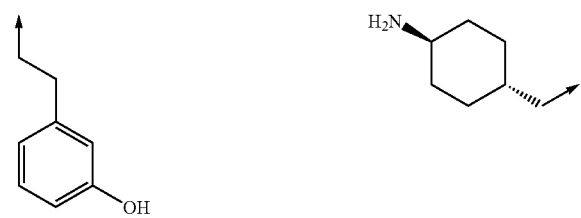

-continued

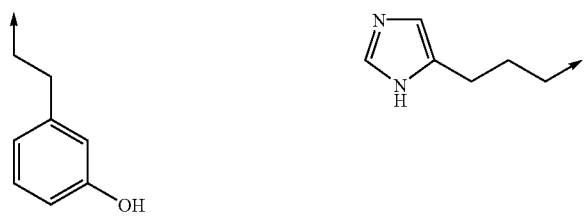

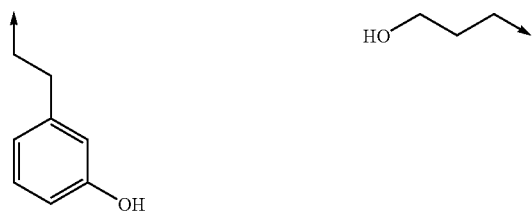

It will also be appreciated that, in addition to the compounds listed above, the present invention also encompasses those compounds in which $R_A$ is a lower alkyl or is a branched aliphatic or heteroaliphatic moiety. In certain embodiments, $R_A$ is methyl or ethyl, and in certain other embodiments, $R_A$ is isopropyl.

Example 48

In Vitro and In Vivo Assays and Exemplary Biological Data

Compounds of this invention may be evaluated in a variety of assays to determine their biological activities. For example, the compounds of the invention can be tested for their ability to inhibit Src kinase or other protein kinases, to bind to bone, to inhibit bone resorption or to otherwise improve the relative dynamics of bone homeostasis. The compounds can also be evaluated for their cytotoxic and growth inhibitory effects on tumor cells of interest.

A. Anti-Resorption Cell Assay (Rabbit Osteoclast):

Femurs, tibias, and scapulas were isolated from 3–4 day old New Zealand white rabbits (Millbrook Farms, Amherst, Mass.). Bones were chopped and minced in a-MEM (Gibco-BRL) containing 0.55 g/L NaHCO3, 10 mM HEPES (Gibco-BRL), 50 units/ml penicillin, and 0.05 mg/ml streptomycin, pH 7.1. Bone fragments were allowed to settle by gravitation, supernatant was collected and centrifuged at 400 RPM (Beckman GS-6KR) for two minutes, and the cell pellet was resuspended in the same medium supplemented with 10% HIFBS (Hyclone). For prebinding experiments, 0.75 ml of cell suspension was added to wells containing sperm whale dentine discs preincubated for 2 hours with 0.75 ml culture medium containing a 2× concentration of test compound. Alternatively, 0.75 ml of cell suspension was added to each well containing dentine slices preincubated with 0.75 ml culture medium alone and test compound was added after the adhesion phase. Sperm whale dentine was cut as 1 mm×6 mm circular discs. The adhesion phase was carried out for 30 minutes at 37° C. and 5% CO2 and then the medium and non-adherent cells and debris were removed by aspiration. Fresh culture medium containing serially diluted test compounds was added and cells were incubated on dentine for 24 hours at 37° C. and 5% CO2. After the resorption phase, dentine slices were soaked for 30 seconds in 0.5% sodium hypochlorite, wiped clean of adherent cells, and then stained for 30–45 seconds with 1% toluidine blue. Resorption was measured using reflective light microscopy and automated image analysis. The resorbed area was measured on the entire 6 mm disc. Remaining cells in the 24-well plates were stained for tartrate resistant acid phosphatase (TRAP) and also assessed visually for the presence of fibroblasts. Experiments were carried out containing triplicate samples for each concentration of compound tested with five untreated control samples per plate. IC50 values were calculated based on the % resorption in the presence of compound relative to vehicle alone treated control samples. Data were calculated from at least three independent experiments each containing triplicate samples.

Generally speaking, in this assay, IC50 values below about 10 µM are of particular interest, while scores below 500 nM are preferred, and scores below about 100 nM are particularly preferred.

Certain embodiments in which $R^C$ is a moiety —NR, where R is a lower aliphatic moiety substituted with (a) a pyridine ring bearing a —PO(OR$_1$)$_2$ substituent or (b) a —CX[PO(YR$_1$)$_2$]$_2$ substituent, where X is H, —OH, or lower alkyl; RA is a cyclic or acyclic aliphatic or heteroaliphatic moiety or is an aryl or alkylaryl moiety optionally substituted by one or more hydroxyl moieties, and RB is a substituted or unsubstituted aryl moiety, have led to IC50 values in the range of about 4 µM–about 100 µM. In certain of those embodiments, R1 is hydrogen and in certain other embodiments, at least one of R1 is an alkyl moiety.

Evaluation of Compounds of the Formula:

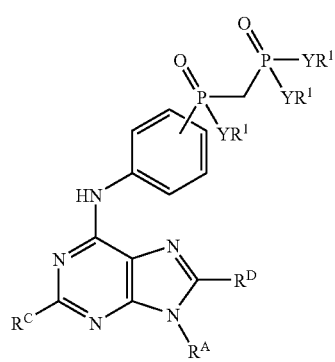

in which RA is a cyclic or acyclic aliphatic or heteroaliphatic moiety or alkylaryl moiety optionally substituted with one or more hydroxyl moieties; RC is an amino moiety substituted with a cyclic or acyclic aliphatic or heteroaliphatic moiety having one or more substituted or unsubstituted amino moieties, or is a hydroxyl, halogen, alkoxy or heterocycle moiety have have yielded IC50 values in the range of about 1 µM–about 100 µM.

Other compounds, in which $R^B$ is a phenyl ring bearing a p—CH[PO(YR$_1$)$_2$]$_2$ substituent or is an aryl moiety with a —PO(YR$_1$)$_2$ moiety in both meta and para positions; RA is a cyclic or acyclic aliphatic or an alkylaryl moiety optionally substituted with one or more hydroxyl moieties; and RC is an amino moiety substituted with a cyclic or acyclic aliphatic or heteroaliphatic moiety optionally substituted with one or more amino or substituted amino moieties have yielded IC50 values in the range of ~1 µM to about 20 µM.

B. Kinase Assays

In addition to their ability to inhibit bone resorption, the compounds of the present invention are also able to inhibit protein kinase activity.

The following Example presents a general method for determining the effect of the inventive compounds on the phosphorylation of a kinase's target.

A purified or partially purified kinase is incubated with a peptide comprising the target sequence of the kinase under conditions suitable for the kinase to phosphorylate its target sequence of amino acids (i.e., protein, peptide). The particular requirements of the kinase may be determined empirically by one of skill in the art, or the conditions that have been published for a particular kinase (for example, see Table I in Boutin "Tyrosine protein kinase assays" J. Chromatography B 684:179–199, 1996; incorporated herein by reference) may be used. The extent of phosphorylation of the target peptide is determined in the presence and absence of the inventive compound and may be determined in the presence of varying concentrations of the inventive compound. The phosphorylation rate may be determined by any means known in the art including electrophorectic assays, chromatographic assays, phosphocellulose assays, etc.

In an electrophorectic assay, a radiolabled phosphate donor such as ATP or GTP is incubated with the peptide substrate in the presence of a kinase. The phosphorylated substrate versus the phosphate donor (e.g., ATP, GTP) are separated via thin-layer electrophoresis (Hunter J. Biol. Chem. 257:4843, 1982; incorporated herein by reference). Any matrix may be used in the electrophoresis step including polyacrylamide, cellulose, etc. The extent of phosphorylation may then be determined by autoradiography or scintillation counting.

The labeled phosphate donor may be separated from the phosphorylated amino acid sequence by standard chromatography techniques. Any matrix may be used to effect the separation including ion exchange resins, PEI cellulose, silica gel, etc. Standard column chromatography methods may be used, or HPLC methods may be used for faster cleaner separations. The radio-labeled peptides are detected by scintillation counting to determine the phosphorylation rate.

Another method which is historically the most popular is the phosphocellulose paper assay, first described by Witt et al. (Witt et al. Anal. Biochem. 66:253, 1975; incorporated herein by reference). This method is well adapted to the screening of inhibitors (Traxler et al. J. Med. Chem. 34:2328, 1991, incorporated herein by reference).

Immunological methods may also be used to detect the phosphorylation of a peptide or protein substrate. For example, anti-phosphotyrosine antibodies may be used in the detection or precipitation of phosphorylated amino acid sequences. The method has the advantage of not requiring the used of radio-labeled ATP.

In comparing the rates of phosphorylation in the presence and absence of the test compound, the compound should lead to at least a 25% decrease in the rate of phosphorylation, more preferably at least 50%, and most preferably at least 75%. These decreases are preferably obtained at micromolar concentrations of the compound and more preferably nanomolar concentrations (e.g., less than 100 nM). In addition, a Quantitative Kinase Activity Assay Using a 96-Well Plate can be determined. The following Example has been adapted from the assay described by Asthagiri et al. (Anal. Biochem. 269:342–347, 1999; incorporated herein by reference). This assay allows high-throughput screening of a large number of potential kinase inhibitors.

The surface of a microtiter plate is coated with antibodies directed against the kinase to be studied. Reacti-Bind protein A-coated wells (Pierce, Rockford, Ill.) are incubated overnight at 4° C. with 50 µL of 10 µg/ml antibody in blocking buffer containing 1% BSA, 50 mM Tris (pH 7.5), 150 mM NaCl, and 0.05% Triton. Wells are then washed three times with blocking buffer. A cell lysate containing the kinase to be studied is diluted in lysis buffer to a total volume of 50 µl incubated for 3 hours at 4° C. to allow the antibody to capture the kinase. To measure background, an extra well is incubated with just lysis buffer and is handled throughout the assay in the same manner as other samples. Each well is then washed twice with 200 µl wash buffer containing 50 mM Tris (pH 7.5) and 150 mM NaCl and twice more with 200 µl kinase wash buffer containing 20 mM Tris (pH 7.5), 15 mM magnesium chloride, 5 mM β-glycerolphosphate (pH 7.3), 1 mM EGTA, 0.2 mM sodium orthovanadate, and 0.2 mM DTT. The contents of the well are then resuspended in 20 µl kinase wash buffer.

To each well is then added 20 µl of 2 mg/ml substrate containing the target amino acid sequence of the kinase. To initiate the in vitro reaction, 20 µl kinase assay buffer containing 20 mM Tris (pH 7.5), 15 mM magnesium chloride, 5 mM β-glycerophosphate (pH 7.3), 1 mM EGTA, 0.2 mM sodium orthovanadate, 0.2 mM DTT, 0.4 µM protein kinase A inhibitor peptide (Upstate Biotech, Lake Placid, N.Y.), 4 µM protein kinase C inhibitor peptide (Upstate Biotech), 4 µM calmidazolium (Upstate Biotech), 25 µM ATP, and 6 µCi [$^{32}$P]-ATP is added to two wells. To one of the wells is added the test compound at a concentration ranging from 1 mM to 1 nM. Reactions contents are maintained under agitation at 37° C. with the Jitterbug (Boekel, Feasterville, Pa.). After 10 minutes, the reactions are quenched with 60 µl of 75 mM phosphoric acid.

[$^{32}$P]-labeled substrate is separated from unreacted [$^{32}$P]-ATP by filtering 40 µl of the quenched reaction contents through a phosphocellulose filter using the Millipore Multiscreen system (Millipore, Bedford, Mass.). Each filter is washed five times with 200 µl 75 mM phosphoric acid and three times with 200 µl 70% ethanol. The filters are allowed to dry before punching out the filters into scintillation vials. $^{32}$P amounts on the filter paper are quantified using CytoScint (ICN Biomedicals, Costa Mesa, Calif.) scintillation fluid and a RackBeta (Wallac, Gaithersburg, Md.) scintillation counter. $^{32}$P measurements are adjusted by subtracting the radioactivity associated with the background sample, and measurements observed in presence and absence of the test compound are compared.

If desired, one may use an involving immunoprecipitation of the kinase. The following such assay was adapted from the method by Bondzi et al. (Oncogene 19:5030–5033, 2000; incorporated herein by reference).

Cells expressing the kinase of interested are washed once in PBS and lysed in buffer containing 20 mM Tris (pH 7.9), 137 mM NaCl, 5 mM EDTA, 1 mM EGTA, 10 mM NaF, 1 mM sodium pyrophosphate, 100 µM β-glycerophosphate, 10 µg/ml aprotinin, 1 mM PMSF, 10% glycerol, and 1% v/v Triton X-100. The lysate is cleared by centrifugation at 10,000×g for 10 minutes at 4° C. Protein concentrations are determined using the BCA method (Pierce, Rockford, Ill., USA). Five hundred µg of the lysate protein is then added to 2 µg monoclonal anti-kinase antibody directed against a portion of the protein. Antibodies are prebound to 100 µl of protein A+G-agarose beads (Santa Cruz Biotechnology, Santa Cruz, Calif., USA) by incubation for one hour at 4° C. on a slow rotator. Increasing amounts of lysate protein (0, 50, 100, 200, 400, 800, and 1600 µg) or increasing amounts of anti-kinase antibody (0, 0.5, 1.0, 2.0, and 4.0 µg) are used in the immunoprecipitation step. The immunocomplex is washed three times in ice-cold lysis buffer, once in ice-cold washing buffer containing 10 mM HEPES (pH 7.4), 100 mM NaCl, 20 µg/ml aprotinin, and 0.5% NP-40, and once in ice-cold reaction buffer containing 20 mM Tris (pH 7.4), 20 mM NaCl, 1 mM DTT, 10 mM MgCl2, and 1 mM MnCl2. The kinase reaction is performed in the presence of 20 µM ATP and 500 ng of the peptide substrate in a total volume of 40 µl of reaction buffer at 30° C. for 30 minutes with gentle agitation. The kinase reaction may be performed using increasing incubation intervals (0, 5, 10, 15, 20, 25, and 30 minutes), increasing amounts of the substrate (0, 100, 200, 400, and 500 ng), and increasing concentrations of the test compound (0, 1, 10, 100, 1000, 10000, and 100000 ng). The kinase reaction is terminated by the addition of 40 µl 2×SDS sample buffer followed by boiling for 10 minutes. The samples are resolved by SDS-PAGE, transferred to Immobilon-P membrane (Millipore Corp., Bedford, Mass., USA), and probed with a polyclonal phospho-substrate antibody. The blot is stripped and reprobed sequentially for kinase and substrate with anti-kinase antibody and anti-substrate antibody, respectively. Dectection is accomplished using the ECL-Plus chemiluminescent system (Amersham, Arlington Heights, Ill., USA) and visualized using a Fuji cooled CCD camera and the Aida 2.0 software package (Raytest Inc., New Castle, Del., USA).

To illustrate this, a Src kinase inhibition assay is utilized as detailed below:

Compounds were tested for their ability to inhibit Src kinase using the scintillation proximity assay (SPA) technology as developed by Amersham. Reagents include: Streptavidin SPA beads from Amersham, 2-[N-morpholino]ethanesulfonic acid from Sigma, ATP from Boerhinger Mannheim, [33P]ATP: from NEN (NEG 602H), the substrate—biotinylated peptide substrate 1 (PKS1) (cdc2 peptide) from Pierce which is prepared at 12.5 µM (5× solution) in kinase buffer, and the enzyme, human recombinant c-Src at 135 µg/ml (stock solution) which is diluted 1/40 in kinase buffer (3.38 µg/ml) before use. Buffers include: (a) Kinase buffer which contains MES 30 mM pH 6.8, MgCl2 10 mM, Orthovanadate 0.25 mM, PMSF 0.1 mM, and DTT 1 mM; (b) ATP buffer which contains ATP 5 mM in MgCl2 50 mM buffer (stock solution). Note that before each use dilute in MES to 100 µM (5× solution) add 100 µCi/mL [33P]ATP; and (c) PBS Stop buffer which contains ATP 0.1 mM, EDTA 40 mM, Triton 0.1%. Streptavidin beads are suspended at 3.3 mg/ml in stop buffer and mixed by shaking. The Kinase reaction proceeds by stepwise addition to wells on the 96 well-plate of the following: (a) 10 µL kinase buffer+10% DMSO or compound to be tested at different concentration in MES+10% DMSO, (b) 10 µL kinase buffer, (c) 10 µL substrate 12.5 µM, (d) 10 µL enzyme 3.38 µg/ml, and (e) 10 µL ATP 100 µM containing 0.2 µCi [33P]ATP. Incubation for 2 hours at 30 degrees C. is followed by addition of 150 µL Stop buffer containing 500 µg streptavidin beads. Incubation proceeds for 30 min at room temperature, followed by centrifugation for 5 min at 2000 rpm, and reading on a Wallac Microbeta Scintillation counter.

Exemplary in vitro Data For Src Kinase Inhibition Assay:

1) Many compounds of this invention, including those of the general structure:

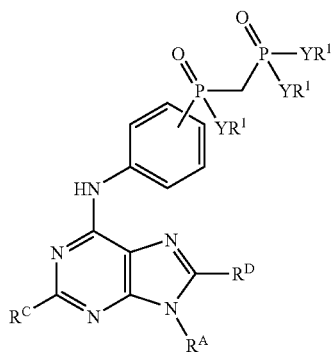

with various substituents as described herein have been found to inhibit the kinase activity of Src with an IC50 value from about 1 nM to about 1 µM. Those compounds include embodiments in which $R^B$ is either of the following structures:

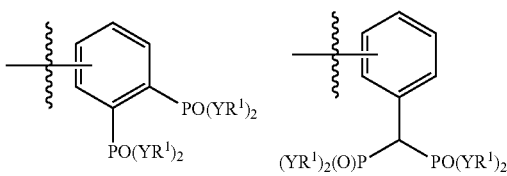

Other compounds with kinase inhibitory activity in that range include those in which $R^C$ is of the general structure:

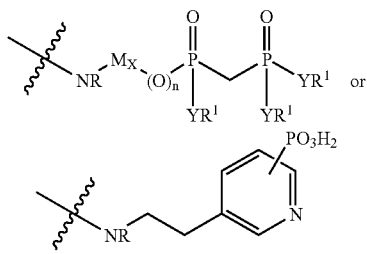

in which Mx in this case is a bond or a linear or branched aliphatic moiety and n is 0 or 1 in which $R^A$ is a cyclic or acyclic aliphatic moiety and wherein RC is an amino moiety substituted with a cycloaliphatic or cycloheteroaliphatic moiety optionally substituted with one or more amino moieties. Activity around the level of 15 µM was seen with such compounds.

C. Hydroxyapatite Assay:

Hydroxyapatite is the principal mineral component of bone. Hydroxyapatite adsorption chromatography is used as an assay to evaluate the bone-targeting potential of both individual bone-targeting moieties ("monomers") and of pharmaceuticals incorporating bone-targeting groups.

Method: The rentention time of a test compound is measured using a linear gradient from 10 mM sodium phosphate, 0.15 N NaCl, pH=6.8 to 500 mM sodium phosphate, 0.15 N NaCl, pH=–6.8 on a TSK-Gel HA 1000 high pressure liquid chromatography column (7.5 mm×75 mm). The rentention time of the compound is expressed in terms of K=(retention time–void time)/void. This K value is corrected using two reference compounds to correct from inter-column and inter-system variation to obtain a K' value.

Reference Compounds: K' values were determined for known bone targeted compounds, the bisphosphonate, alendronate and tetracycline. Alendronate gave a K' value of 3.7 and tetracycline gave a K' value of 2.0.

D. In Vivo Anti-Resorptive Testing in Hypercalcemic Mouse:

A mouse hypercalcemia model for determining the efficacy of Src kinase inhibitors was developed. This model exploits the intrinsic effects of PTH (1–34) to stimulate the resorptive activity of osteoclasts in vivo. Briefly, compounds are each injected into mice subcutaneously, once or twice per day for five consecutive days. On the third day of compound treatments, PTH administration begins. PTH (20 µg/kg) is given four times per day, subcutaneously, until the end of the study. Control animals receive PTH but do not receive test compounds. Blood samples are collected from the animals to obtain baseline (pre-PTH treatment), 48 hour and 72 hour (after initiation of PTH treatment) serum samples. The serum samples are analyzed for calcium concentration using the quantitative colorimetric assay reagent Arsenazo III (Sigma). Calcium serum levels for treated groups are compared to calcium serum levels of control groups and a percentage of inhibition of hypercalcemia is calculated for each time point. When a compound is effective in inhibiting the activity of osteoclasts, observed serum calcium concentrations are lower than in animals that receive only PTH in the absence of test compound.

Exemplary in Vivo Data for Mouse Hyper-calcemia:

A number of compounds of this invention, when evaluated in the mouse model as described above, in which compounds were administered BID at levels of 10 mg/kg and 3 mg/kg and serum calcium levels checked on day 3 of the study, have yielded inhibitory effects of around 30%–95% and around 10% to 60% (of the PTH-induced increase in serum calcium in control animals), at the higher and lower doses, respectively, indicating biological activity in the animals.

E. Cytoxicity and Inhibition of Tumor Growth:

Certain compounds of this invention have also been demonstrated cytotoxic or growth inhibitory effects on tumor and other cancer cell lines and thus may be useful in the treatment of cancer and other cell proliferative diseases. Compounds are assayed for anti-tumor activity using in vivo and in vitro assays which are well known to those skilled in the art. Generally, initial screens of compounds to identify candidates for anti-cancer drugs are performed in cellular in vitro assays. Compounds identified as having anti-cell proliferative activity can then be subsequently assayed in whole organisms for anti-tumor activity and toxicity. The initial screens are preferably cellular assays which can be performed rapidly and cost-effectively relative to assays that use whole organisms. For purposes of the present invention, the term "anti-proliferative compound" is used to mean compounds having the ability to impede or stop cells from progressing through the cell cycle and dividing. For purposes of the present invention, the terms "anti-tumor" and "anti-cancer" activity are used interchangeably.

Methods for determining cell proliferation are well known and can be used to identify compounds with anti-proliferative activity. In general, cell proliferation and cell viability assays are designed to provide a detectable signal when cells are metabolically active. Compounds are tested for anti-cell proliferation activity by assaying for a decrease in metabolic activity. Commonly used methods for determining cell viability depend upon, for example, membrane integrity (e.g. trypan blue exclusion) or incorporation of nucleotides during cell proliferation (e.g. BrdU or 3H-thymidine).

Preferred methods of assaying cell proliferation utilize compounds that are converted into a detectable compound during cell proliferation. Particularly preferred compounds are tetrazolium salts and include without limitation MTT (3-(4, 5-dimethylthiazol-2-yl)-2,5-diphenyltetrazolium bromide; Sigma-Aldrich, St. Louis, Mo.), MTS (3-(4,5-dimethylthiazol-2-yl)-5-(3-carboxymethoxyphenyl)-2-(4-sulfophenyl)-2H-tetrazolium), XTT (2,3-bis(2-Methoxy-4-nitro-5-sulfophenyl)-2H-tetrazolium-5-carboxanilide), INT, NBT, and NTV (Bernas et al. Biochim Biophys Acta 1451(1): 73–81, 1999). Preferred assays utilizing tetrazolium salts detect cell proliferation by detecting the product of the enzymatic conversion of the tetrazolium salts into blue formazan derivatives, which are readily detected by spectroscopic methods (Mosman. J. Immunol. Methods. 65:55–63, 1983).

Generally, preferred methods for assaying cell proliferation involve incubating cells in a desired growth medium with and without the compounds to be tested. Growth conditions for various prokaryotic and eukaryotic cells are well-known to those of ordinary skill in the art (Ausubel et al. Current Protocols in Molecular Biology. Wiley and Sons. 1999; Bonifacino et al. Current Protocols in Cell Biology. Wiley and Sons. 1999 both incorporated herein by reference). To detect cell proliferation, the tetrazolium salts are added to the incubated cultured cells to allow enzymatic conversion to the detectable product by active cells. Cells are processed, and the optical density of the cells is determined to measure the amount of formazan derivatives. Furthermore, commercially available kits, including reagents and protocols, are available for examples, from Promega Corporation (Madison, Wis.), Sigma-Aldrich (St. Louis, Mo.), and Trevigen (Gaithersburg, Md.).

Any cultured cell line may be used to screen compounds for antiproliferative activity. In certain embodiments of the invention cell lines utilized include, but are not limited to, Exemplary cell lines utilized for the determination of the ability of inventive compounds to inhibit cellular proliferation include, but are not limited to COLO 205 (colon cancer), DLD-1 (colon cancer), HCT-15 (colon cancer), HT29 (colon cancer), HEP G2 (Hepatoma), K-562 (Leukemia), A549 (Lung), NCI-H249 (Lung), MCF7 (Mammary), MDA-MB-231 (Mammary), SAOS-2 (Osteosarcoma), OVCAR-3 (Ovarian), PANC-1 (Pancreas), DU-145 (Prostate), PC-3 (Prostate), ACHN (Renal), CAKI-1 (Renal), MG-63 (Sarcoma).

Preferably, the cell line is a mammalian, but is not limited to mammalian cells since lower order eukaryotic cells such as yeast may also be used to screen compounds. Preferred mammalian cell lines are derived from humans, rats, mice, rabbits, monkeys, hamsters, and guinea pigs since cells lines from these organisms are well-studied and characterized. However, the present invention does not limit the use of mammalians cells lines to only the ones listed.

Suitable mammalian cell lines are often derived from tumors. For example, the following tumor cell-types may be sources of cells for culturing cells: melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Non-limiting examples of mammalian cells lines that have been widely used by researchers include HeLa, NIH/3T3, HT1080, CHO, COS-1, 293T, WI-38 and CV1 /EBNA-1.

Other in vitro cellular assays may be used which rely upon a reporter gene to detect metabolically active cells. Non-limiting examples of reporter gene expression systems include green fluorescent protein (GFP), and luciferase. As an example of the use of GFP to screen for potential antitumor drugs, Sandman et al. (Chem Biol. 6:541–51; incorporated herein by reference) used HeLa cells containing an inducible variant of GFP to detect compounds that inhibited expression of the GFP, and thus inhibited cell proliferation.

Compounds identified by in vitro cellular assays as having anti-cell proliferation activity are then tested for anti-tumor activity in whole organisms. Preferably, the organisms are mammalian. Well-characterized mammalians systems for studying cancer include rodents such as rats and mice. Typically, a tumor of interest is transplanted into a mouse having a reduced ability to mount an immune response to the tumor to reduce the likelihood of rejection. Such mice include for example, nude mice (athymic) and SCID (severe combined immunodeficiency) mice. Other transgenic mice such as oncogene containing mice may be used in the present assays (see for example U.S. Pat. Nos. 4,736,866 and 5,175,383). For a review and discussion on the use of rodent models for antitumor drug testing see Kerbel (Cancer Metastasis Rev. 17:301–304, 1998–99).

In general, the tumors of interest are implanted in a test organism preferably subcutaneously. The organism containing the tumor is treated with doses of candidate anti-tumor compounds. The size of the tumor is periodically measured to determine the effects of the test compound on the tumor. Some tumor types are implanted at sites other than subcutaneous sites (e.g. intraperitoneal sites) and survival is measured as the endpoint. Parameters to be assayed with routine screening include different tumor models, various tumor and drug routes, and dose amounts and schedule. For a review of the use of mice in detecting antitumor compounds see Corbett et al. (Invest New Drugs. 15:207–218, 1997; incorporated herein by reference).

The invention claimed is:

1. A compound of formula (Ia) (or a salt or ester, or salt of an ester, thereof):

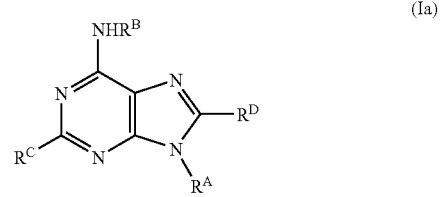

wherein
$R^A$ is Mx-aryl or Mx-heterocycle where M is a substituted or unsubstituted methylene, x is an integer from 1 to 6, the aryl moiety may bear one or more substituents, and the heterocycle is a substituted or unsubstituted, aromatic or nonaromatic heterocyclic moiety comprising a 5- to 7-membered ring bearing one or more heteroatoms;

$R^B$ comprises an aryl, or heteroaryl moiety bearing at least one a substituent of Series IIb:

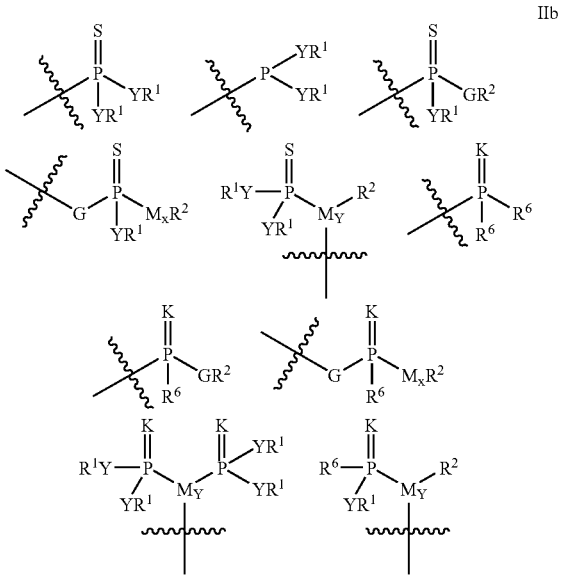

$R^C$ is hydrogen, halogen, an aliphatic, heteroaliphatic, aryl, or heteroaryl moiety, or —ZR, wherein Z is —O—, —S—, or NR, wherein each occurrence of R without a further alphanumeric superscript is independently hydrogen, or a substituted or unsubstituted aliphatic, heteroaliphatic, aryl, or heteroaryl moiety;

each occurrence of K is independently —O— or —S—;

each occurrence of Y is independently —O—, —S—, —NR— or a chemical bond;

each occurrence of R (without a further alphanumeric superscript) is independently hydrogen, or a substituted or unsubstituted aliphatic, heteroaliphatic, aryl, or heteroaryl moiety;

each occurrence of $R^1$ is independently a substituted or unsubstituted aliphatic, heteroaliphatic, aryl, or heteroaryl moiety, or, except in $YR^1$ moieties in which Y is a covalent bond, $R^1$ may also be H;

each occurrence of $R^2$ is independently $R^1$, —PK($YR^1$)($YR^1$), —$SO_2$($YR^1$) or —C(O)($YR^1$);

each occurrence of $R^6$ independently represents an aliphatic, heteroaliphatic, aryl, or heteroaryl moiety;

each occurrence of G is independently —O—, —S—, —NR— or $M_x$; and, each occurrence of $M_Y$ is independently a methine group or a lower alkyl moiety which contains a methine group and optionally may be further substituted, wherein in each of the foregoing groups each aliphatic or heteroaliphatic moiety may be branched or unbranched, cyclic or acyclic and substituted or unsubstituted, and each aryl and heteroaryl moiety may be substituted or unsubstituted.

2. The compound of claim 1 wherein $M_x$ is methylene, ethylene or propylene, and the aryl moiety is o-, m-, or p-hydroxy-, 2,3-dihydroxy-, 2,4-dihydroxy-, 2,5-dihydroxy-, 3,4-dihydroxy-, or 3,5-dihydroxyphenyl.

3. The compound of claim 1, wherein $R^C$ is —OR, where R is H, aliphatic, heteroaliphatic, aryl, or heteroaryl.

4. The compound of claim 1, wherein $R^C$ is —R, —NRR or —OR in which each R is C1–C8 aliphatic, which may be branched or unbranched, cyclic or noncyclic, and which may be substituted with one or more hydroxy, alkoxy, aralkoxy, carbamyl, amino, substituted amino, cyano, halogen, nitro or sulfo groups, and/or with one or more alkyl, alkenyl, alkynyl, cycloalkyl, aryl, heterocyclic, aryloxy or aralkyl moieties which may themselves be substituted with one or more hydroxy, alkoxy, aralkoxy, carbamyl, amino, substituted amino, cyano, halogen, nitro or sulfo groups.

5. The compound of claim 4, wherein each said R comprises a C1–C8 aliphatic moiety substituted with one or more groups selected from the following: a substituted or unsubstituted amine or 5- to 7-membered heterocyclic moiety, which may itself be optionally substituted.

6. A compound of formula (Ib) (or a salt or ester, or salt of an ester, thereof):

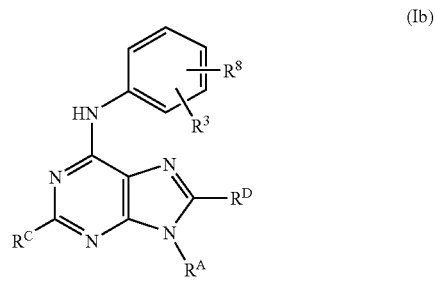

wherein $R^A$ is hydrogen, or an aliphatic, heteroaliphatic, aryl, or heteroaryl moiety;

$R^C$ is an aliphatic, heteroaliphatic, aryl, or heteroaryl moiety;

$R^D$ is hydrogen, halogen, an aliphatic, heteroaliphatic, aryl, or heteroaryl moiety, or —ZR; wherein Z is —O—, —S—, or NR, wherein each occurrence of R without a further alphanumeric superscript is independently hydrogen, or a substituted or unsubstituted aliphatic, heteroaliphatic, aryl, or heteroaryl moiety;

$R^8$ is selected from the moieties of Series II:

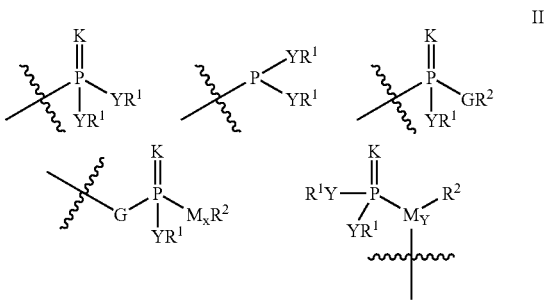

or 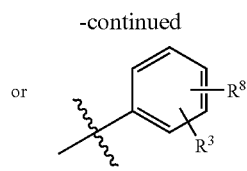

is selected from the moieties of Series III:

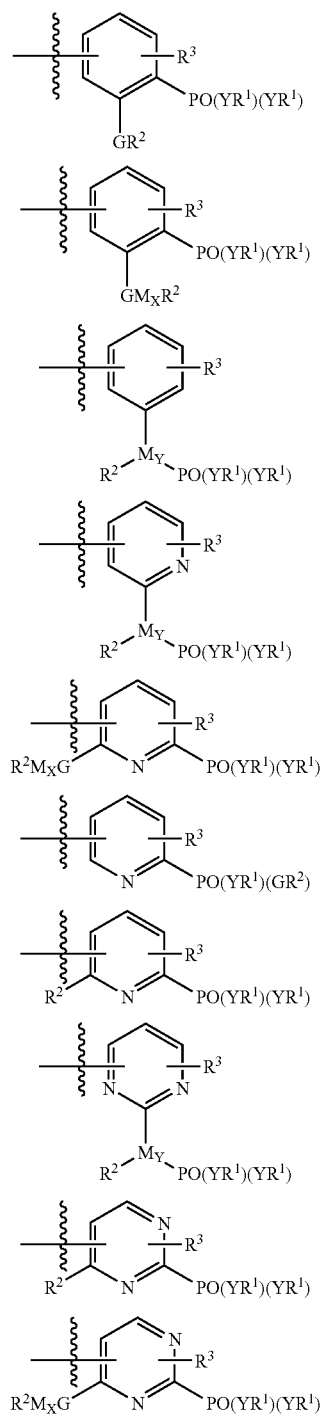

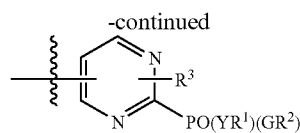

$R^3$ represents from 0–3 substituents independently selected from the group consisting of halogen, R, —GR, —CO(YR), amido, amidino, cyano, nitro, azido, sulfamoyl, sulfonamido, and substituents of Series II;

M is a substituted or unsubstituted methylene; x is an integer from 1 to 6;

each occurrence of K is independently —O— or —S—;

each occurrence of Y is independently —O—, —S—, —NR— or a chemical bond;

each occurrence of $R^1$ is independently a substituted or unsubstituted aliphatic, heteroaliphatic, aryl, or heteroaryl moiety, or, except in $YR^1$ moieties in which Y is a covalent bond, $R^1$ may also be H;

each occurrence of $R^2$ is independently $R^1$, —PK($YR^1$)($YR^1$), —SO$_2$($YR^1$) or —C(O)($YR^1$);

each occurrence of G is independently —O—, —S—, —NR— or $M_x$; and, each occurrence of $M_Y$ is independently a methine group or a lower alkyl moiety which contains a methine group and optionally may be further substituted;

wherein in each of the foregoing groups each aliphatic or heteroaliphatic moiety may be branched or unbranched, cyclic or acyclic and substituted or unsubstituted, and each aryl and heteroaryl moiety may be substituted or unsubstituted;

with the following provisos:

(1) $R^D$ is a moiety other than one comprising a substituted or unsubstituted arylene moiety (in which up to two methine carbons may be replaced by nitrogen atoms), a C3–7 cycloalkylene moiety (which may contain nitrogen atoms in place of up to two ring carbons), an indanylene moiety, or a 1,2,3,4-tetrahydronaphthylene moiety;

(2) $R^D$ is a moiety other than one bearing a cyano group or an N-substituted or unsubstituted amino, amidino, guanidino or guanidinoalkyl group;

$R^C$ is covalently attached through a C—C bond to the carbon atom at ring position 2 of the purine ring system.

7. The compound (or a salt or ester, or salt of an ester, thereof) of the formula:

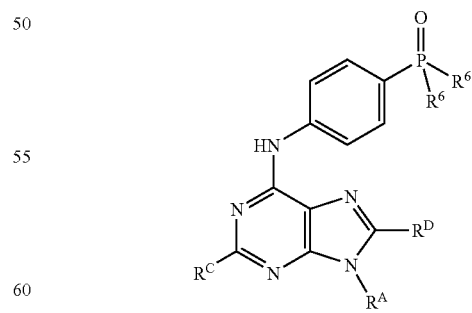

wherein $R^A$ is hydrogen, or an aliphatic, heteroaliphatic, aryl, or heteroaryl moiety;

$R^C$ is hydrogen, halogen, an aliphatic, heteroaliphatic, aryl, or heteroaryl moiety, or —ZR, wherein Z is —O—, —S—, or NR, wherein each occurrence of R without a further alphanumeric superscript is independently hydrogen, or a substituted or unsubstituted aliphatic, heteroaliphatic, aryl, or heteroaryl moiety;

$R^D$ is hydrogen, halogen, an aliphatic, heteroaliphatic, aryl, or heteroaryl moiety, or —ZR, with the proviso that $R^D$ does not bear a cyano group or an N-substituted or unsubstituted amino, amidino, guanidino or guanidinoalkyl group;

each $R^6$ is independently aliphatic, heteroaliphatic, aryl, or heteroaryl and wherein in each of the foregoing groups each aliphatic or heteroaliphatic moiety may be branched or unbranched, cyclic or acyclic and substituted or unsubstituted, and each aryl and heteroaryl moiety may be substituted or unsubstituted.

8. The compound of claim 2, wherein $R^C$ is —R, —NRR or —OR in which each R is C1–C8 aliphatic, which may be branched or unbranched, cyclic or noncyclic, and which may be substituted with one or more hydroxy, alkoxy, aralkoxy, carbamyl, amino, substituted amino, cyano, halogen, nitro or sulfo groups, and/or with one or more alkyl, alkenyl, alkynyl, cycloalkyl, aryl, heterocyclic, aryloxy or aralkyl moieties which may themselves be substituted with one or more hydroxy, alkoxy, aralkoxy, carbamyl, amino, substituted amino, cyano, halogen, nitro or sulfo groups.

9. The compound of claim 8, wherein each said R comprises a C1–C8 aliphatic moiety substituted with one or more groups selected from the following: a substituted or unsubstituted amine or 5- to 7-membered heterocyclic moiety, which may itself be optionally substituted.

10. The compound of claim 7 in which $R^D$ is H or halo.

11. The compound of claim 7 wherein $R^C$ is an aliphatic, heteroaliphatic, aryl, or heteroaryl moiety which is covalently attached through a carbon-carbon bond to the carbon atom at ring position 2 of the purine ring system.

12. The compound of claim 11 in which $R^D$ is H.

13. The compound of claim 12 in which $R^D$ is F.

14. The compound of any of claims 1, 2, 3, 4, 5, 8 or 9 in which $R^B$ comprises

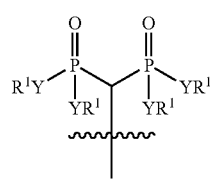

wherein each $R^1$ is independently H, alkyl, arylalkyl, or aryl.

15. The compound of any of claims 1, 2, 3, 4, 5, 8 or 9 in which $R^B$ comprises

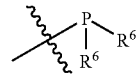

wherein each $R^6$ is independently alkyl, arylalkyl, or aryl.

16. The compound of any of claims 1, 2, 3, 4, 5, 8 or 9 in which $R^B$ comprises

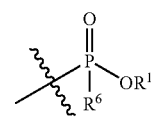

wherein $R^1$ is H, alkyl, or arylalkyl and $R^6$ is aliphatic, heteroaliphatic, aryl, or heteroaryl.

17. The compound of any of claims 1, 2, 3, 4, 5, 8 or 9 in which $R^B$ comprises

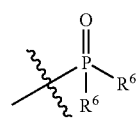

wherein each $R^6$ is independently aliphatic, heteroaliphatic, aryl, or heteroaryl.

18. The compound of any of claims 1, 2, 3, 4, 5, 8 or 9 in which $R^B$ comprises

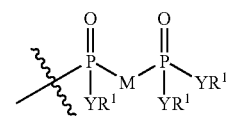

wherein each $R^1$ is H, alkyl, or arylalkyl.

19. The compound of any of claims 1, 2, 3, 4, 5, 8 or 9 in which $R^B$ comprises

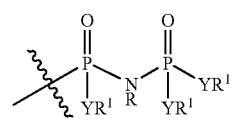

wherein each $R^1$ is independently H, H, alkyl, arylalkyl, or aryl and R is aliphatic, heteroaliphatic, aryl, or heteroaryl.

20. A composition containing a compound of any of claims 1, 2, 3, 4, 5, 14, 15, 16, 17, 18, 19, 6, 7, 8, 9, 10, 11 or 12, and one or more pharmaceutically acceptable excipients or additives.

* * * * *